US007608421B2

(12) United States Patent
Lang et al.

(10) Patent No.: US 7,608,421 B2
(45) Date of Patent: Oct. 27, 2009

(54) METHOD FOR THE PRODUCTION OF 7-DEHYDROCHOLESTEROL AND/OR THE BIOSYNTHETIC INTERMEDIATE OR SUBSEQUENT PRODUCTS THEREOF IN TRANSGENIC ORGANISMS

(75) Inventors: Christine Lang, Berlin (DE); Markus Veen, Berlin (DE)

(73) Assignee: Organobalance GmbH, Berlin (DE)

( * ) Notice: Subject to any disclaimer, the term of this patent is extended or adjusted under 35 U.S.C. 154(b) by 290 days.

(21) Appl. No.: 10/503,044

(22) PCT Filed: Jan. 22, 2003

(86) PCT No.: PCT/EP03/00592

§ 371 (c)(1),
(2), (4) Date: Jul. 29, 2004

(87) PCT Pub. No.: WO03/064650

PCT Pub. Date: Aug. 7, 2003

(65) Prior Publication Data
US 2006/0240508 A1 Oct. 26, 2006

(30) Foreign Application Priority Data
Jan. 29, 2002 (DE) .................. 102 03 352

(51) Int. Cl.
C12P 33/00 (2006.01)
C12N 9/02 (2006.01)
(52) U.S. Cl. .................. 435/52; 435/189
(58) Field of Classification Search ............... None
See application file for complete search history.

(56) References Cited

U.S. PATENT DOCUMENTS 5,480,805 A * 1/1996 Wolf et al. ............. 435/320.1

FOREIGN PATENT DOCUMENTS

| EP | 486290 B1 | 5/1992 |
| WO | WO-98/45457 A1 | 10/1998 |
| WO | WO-99/16886 A1 | 4/1999 |
| WO | WO-02/061072 A2 | 8/2002 |

OTHER PUBLICATIONS

Arthington, et al. "Cloning, disruption and sequence of the gene encoding yeast C-5 sterol desaturase." *Gene*. Jun. 15, 1991; 102(1):39-44.
Ashman, et al. "Cloning and disruption of the yeast C-8 sterol isomerase gene." *Lipids*. Aug. 1991; 26(8):628-32.
Avruch, et al. "The induced biosynthesis of 7-dehydrocholesterols in yeast: potential sources of new provitamin $D_3$ analogs." *Can J Biochem*. Jul. 1976; 54(7):657-65.

Basson, et al. "Structural and functional conservation between yeast and human 3-hydroxy-3-methylglutaryl coenzyme A reductases, the rate-limiting enzyme of sterol biosynthesis." *Mol Cell Biol*. Sep. 1988; 8(9):3797-808.
Braverman, et al. "Mutations in the gene encoding 3 β-hydroxysteroid-$\Delta^8$, $\Delta^7$-isomerase cause X-linked dominant Conradi-Hunermann syndrome." *Nat Genet*. Jul. 1999; 22(3):291-4.
Chang, et al. "Molecular cloning and functional expression of human acyl-coenzyme A:cholesterol acyltransferase cDNA in mutant Chinese hamster ovary cells." *J Biol Chem*. Oct. 5, 1993; 268(28):20747-55.
Hardwick, et al. "*SED6* is identical to *ERG6*, and encodes a putative methyltransferase required for ergosterol synthesis." *Yeast*. Feb. 1994; 10(2):265-9.
Husselstein, et al. "$\Delta^7$-sterol-C5-desaturase: molecular characterization and functional expression of wild-type and mutant alleles." *Plant Mol Biol*. Mar. 1999; 39(5):891-906.
Jandrositz, et al. "The gene encoding squalene epoxidase from *Saccharomyces cerevisiae*: cloning and characterization." *Gene*. Oct. 30, 1991: 107(1):155-60.
Jennings, et al. "Molecular cloning and characterization of the yeast gene for squalene synthetase." *Proc Natl Acad Sci USA*. Jul. 15, 1991; 88(14):6038-42.
Kalb, et al. "Isolation of a cytochrome P-450 structural gene from *Saccharomyces cerevisiae*." *Gene*. 1986; 45(3):237-45.
Lai, et al. "The identification of a gene family in the *Saccharomyces cerevisiae* ergosterol biosynthesis pathway." *Gene*. Mar. 11, 1994; 140(1):41-9.
Lees, et al. "Cloning of the late genes in the ergosterol biosynthetic pathway of *Saccharomyces cerevisiae*—a review." *Lipids*. Mar. 1995; 30(3):221-6.
Nishi, et al. "cDNA cloning of the mammalian sterol C5-desaturase and the expression in yeast mutant." *Biochim Biophys Acta*. Jan. 31, 2000; 1490(1-2):106-8.
Polakowski, et al. "Overexpression of a cytosolic hydroxymethylglutaryl-CoA reductase leads to squalene accumulation in yeast." *Appl Microbiol Biotechnol*. Jan. 1998; 49(1):66-71.
Silve, et al. "Emopamil-binding protein, a mammalian protein that binds a series of structurally diverse neuroprotective agents, exhibits $\Delta^8$-$\Delta^7$ sterol isomerase activity in yeast." *J Biol Chem*. Sep. 13, 1996; 271(37):22434-40.
Skaggs, et al. "Cloning and characterization of the *Saccharomyces cerevisiae* C-22 sterol desaturase gene, encoding a second cytochrome P-450 involved in ergosterol biosynthesis." *Gene*. Feb. 22, 1996; 169(1):105-9.

(Continued)

*Primary Examiner*—Andrew Wang
*Assistant Examiner*—Md. Younus Meah
(74) *Attorney, Agent, or Firm*—Mayer & Williams PC; Ann A. Wieczorek, Esq.

(57) ABSTRACT

The present invention relates to a method for preparing 7-dehydrocholesterol and/or the biosynthetic intermediates and/or secondary products thereof by culturing organisms, in particular yeasts. Furthermore, the invention relates to the preparation of the nucleic acid constructs required for preparing the genetically modified organisms and to said genetically modified organisms, in particular yeasts, themselves.

14 Claims, 10 Drawing Sheets

OTHER PUBLICATIONS

Figure 1:
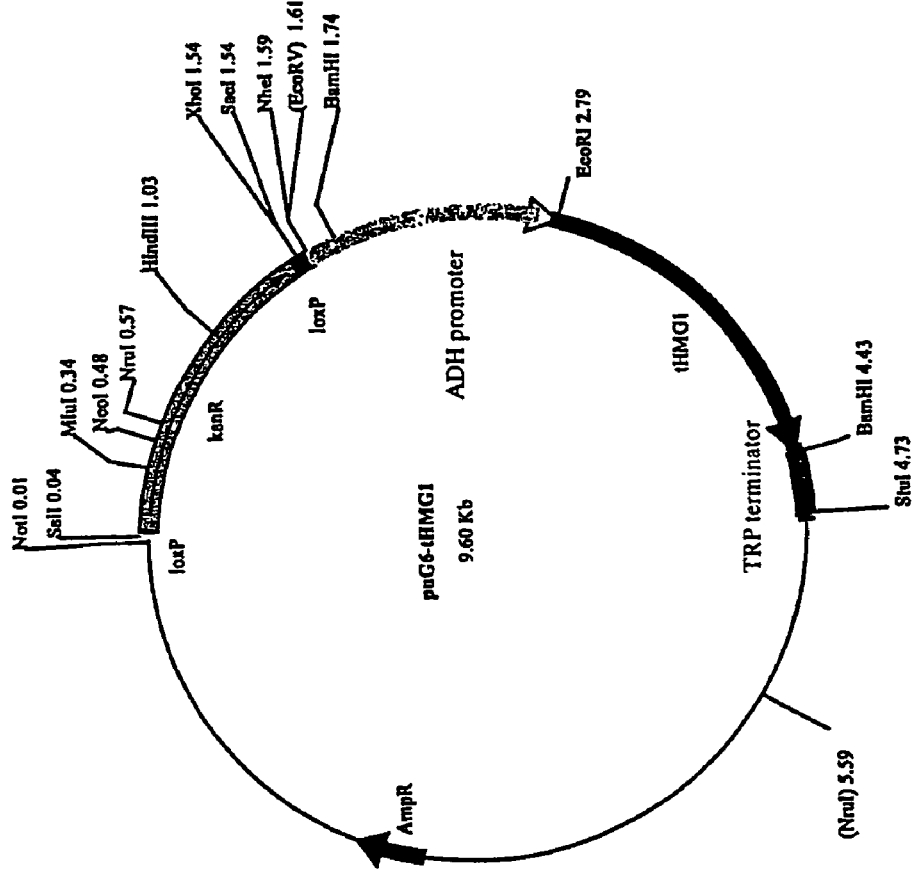

Tainaka, et al. "Effects of elevated expression of the *CYP51* ($P450_{14DM}$) gene on the sterol contents of *Saccharomyces cerevisiae*." *Journal of Fermentation and Bioengineering* 1995; 79(1):64-6.

Uelmen, et al. "Tissue-specific expression and cholesterol regulation of acylcoenzyme A:cholesterol acyltransferase (ACAT) in mice. Molecular cloning of mouse ACAT cDNA, chromosomal localization, and regulation of ACAT in vivo and in vitro." *J Biol Chem*. Nov. 3, 1995: 270(44):26192-201.

Waterham, et al. "Mutations in the 3β-hydroxysterol $\Delta^{24}$-reductase gene cause desmosterolosis, an autosomal recessive disorder of cholesterol biosynthesis." *Am J Hum Genet*. Oct. 2001; 69(4):685-94.

Xu, et al. "Biosynthesis of cholesterol in the yeast mutant erg6." *Biochem Biophys Res Commun*. Aug. 30, 1988; 155(1):509-17.

Yang, et al. "Sterol esterification in yeast: a two-gene process." *Science*. May 31, 1996; 272(5266): 1353-6.

Yu, et al., "Molecular Cloning and Characterization of Two Isoforms of *Saccharomyces cerevisiae* Acyl-CoA:Sterol-Acyltransferase." *J. Biol. Chem*. Sep. 27, 1996; 271(39): 24157-63.

T. Polakowski, Molekularbiologische Beeinflussung des Ergosterolstoffwechsels der Hefe *Saccharomyces cerevisiae*, Shaker Verlag Aachen, 1999, Seite 59 bis 66.

International Search Report for PCT/EP 03/00592 (4 pages).

Pena-Diaz, J. et al., "A soluble 3-hydroxy-3-methylglutaryl-CoA reductase in the protozoan *Trypanosoma cruzi*", Biochem. J., (1997), vol. 324, pp. 619-626.

Basson, M.E. et al., "Structural and Functional Conservation between Yeast and Human 3-Hydroxy-3-Methylglutaryl Coenzyme A Reductases, the Rate-Limiting Enzyme of Sterol Biosynthesis", Molecular and Cellular Biology, Sep. 1988, vol. 8, No. 9, pp. 3797-3808.

Bischoff, K.M. et al., "3-Hydroxy-3-Methylglutaryl-Coenzyme A Reductase from *Haloferax volcanii*: Purification, Characterization, and Expression in *Escherichia coli*", Journal of Bacteriology, Jan. 1996, vol. 178., No. 1, pp. 19-23.

Bochar, D.A. et al., "3-Hydroxy-3-Methylglutaryl Coenzyme A Reductase of Sulfolobus solfataricus: DNA Sequence, Phylogeny, Expression in *Escherichia coli* of the hmgA Gene, and Purification and Kinetic Characterization of the Gene Product", Journal of Bacteriology, Jun. 1997, vol. 179, No. 11, pp. 3632-3638.

\* cited by examiner

METHOD FOR THE PRODUCTION OF 7-DEHYDROCHOLESTEROL AND/OR THE BIOSYNTHETIC INTERMEDIATE OR SUBSEQUENT PRODUCTS THEREOF IN TRANSGENIC ORGANISMS

The present invention relates to a method for preparing 7-dehydrocholesterol and/or the biosynthetic intermediates and/or secondary products thereof by culturing organisms, in particular yeasts. Furthermore, the invention relates to the preparation of the nucleic acid constructs required for preparing the genetically modified organisms and to said genetically modified organisms, in particular yeasts, themselves.

7-Dehydrocholesterol, also referred to as cholesta-5,7-dienol or provitamin D3, its biosynthetic intermediates of the sterol metabolism, such as, for example, zymosterol, farnesol, geraniol, squalene, lanosterol, cholesta-5,7,24-trienol and cholesta-5,7,22,24-tetraenol and its biosynthetic secondary products of the sterol metabolism, such as vitamin $D_3$ and cholesterol, are compounds of high economic value.

7-Dehydrocholesterol is economically important especially for obtaining vitamin $D_3$ from 7-dehydrocholesterol via UV irradiation.

Squalene is used as building block for the synthesis of terpenes. It is used in hydrogenated form as squalane in dermatology and cosmetics and also in various derivatives as an ingredient of skin and haircare products.

Furthermore, sterols such as zymosterol and lanosterol can be utilized economically, lanosterol being pivotal as crude and synthesis material for the chemical synthesis of saponins and steroid hormones. Due to its good skin penetration and spreading properties, lanosterol serves as emulsifier and active substance in skin creams.

An economic method for preparing 7-dehydrocholesterol and/or the biosynthetic intermediates and/or secondary products thereof is therefore of great importance.

Particularly economic methods are biotechnological methods utilizing organisms which have been optimized by genetic modification and which produce 7-dehydrocholesterol and/or the biosynthetic intermediates and/or secondary products thereof.

While the sterol metabolism in bacteria, fungi, yeasts and some insects essentially goes from zymosterol via fecosterol, episterol, ergosta-5,7-dienol and ergosta-5,7,22,24-tetraen-3β-ol to ergosterol (provitamin $D_2$), the sterol metabolism in mammals essentially goes from zymosterol via cholesta-7,24-dienol, lathosterol to 7-dehydrocholesterol (provitamin $D_3$).

7-Dehydrocholesterol (provitamin $D_3$) is converted to cholesterol by 7-dehydrocholesterol reductase and cholesterol is converted to steroid hormones, corticoids and bile acids, such as progesterone, testosterone, estradiol, aldosterone, cortisone and cholate.

Some genes of the 7-dehydrocholesterol metabolism in mammals are known and have been cloned, such as, for example, nucleic acids encoding a human Δ8-Δ7-isomerase (also referred to as emopamil-binding protein (EBP)), ACCESSION NM_006579, and a murine Δ8-Δ7-isomerase (Braverman, N. et al., (1999): Mutations in the gene encoding 3beta-hydroxysteroid-delta8,delta7-isomerase cause X-linked dominant Conradi-Hunermann syndrome. Nat. Genet. 22(3),291-294), nucleic acids encoding a human Δ5-desaturase (also referred to as sterol C5-desaturase), ACCESSION AB016247 and a murine Δ5-desaturase (Nishi, S. et al., (2000): cDNA cloning of the mammalian sterol C5-desaturase and the expression in yeast mutant. Biochim. Biophys. Acta 1490(1-2), 106-108), nucleic acids encoding a human Δ24-reductase (also referred to as 24-dehydrocholesterol reductase (DHCR24)), ACCESSION NM_014762 and a murine Δ24-reductase (Waterham, H. R. et al. (2001): Mutations in the 3beta-hydroxysterol Delta24-reductase gene cause desmosterolosis, an autosomal recessive disorder of cholesterol biosynthesis. Am. J. Hum. Genet. 69(4),685-694) and nucleic acids encoding a human sterol acyltransferase (Chang, C. C. et al., Molecular cloning and functional expression of human acyl-coenzyme A:cholesterol acyltransferase cDNA in mutant Chinese hamster ovary cells, J. Biol. Chem. 1993, Oct. 5; 268(28):20747-55) and a murine sterol acyltransferase (Uelmen, P. J.: Tissue-specific expression and cholesterol regulation of acylcoenzyme A:cholesterol acyltransferase (ACAT) in mice. Molecular cloning of mouse ACAT cDNA, chromosomal localization, and regulation of ACAT in vivo and in vitro, J. Biol. Chem. 1995 Nov. 3; 270(44):26192-201).

The genes of the ergosterol metabolism in yeast are essentially known and have been cloned, such as, for example, nucleic acids encoding a Δ8-Δ7-isomerase (ERG2) (Ashman, W. H. et al. (1991): Cloning and disruption of the yeast C-8 sterol isomerase gene. Lipids. August; 26(8):628-32.), nucleic acids encoding a Δ5-desaturase (ERG3) (Arthington, B. A. et al. (1991): Cloning, disruption and sequence of the gene encoding yeast C-5 sterol desaturase. Gene. June 15; 102(1):39-44.), nucleic acids encoding a Δ24-reductase (ERG 4) (Lai, M. H. et al., (1994): The identification of a gene family in the *Saccharomyces cerevisiae* ergosterol biosynthesis pathway. Gene. March 11; 140(1):41-9.), nucleic acids encoding an HMG-CoA reductase (HMG)(Bason M. E. et al, (1988) Structural and functional conservation between yeast and human 3-hydroxy-3-methylglutaryl coenzyme A reductases, the rate-limiting enzyme of sterol biosynthesis. Mol Cell Biol 8:3797-3808, nucleic acids encoding a truncated HMG-CoA reductase (t-HMG) (Polakowski T, Stahl U, Lang C. (1998) Overexpression of a cytosolic hydroxymethylglutaryl-CoA reductase leads to squalene accumulation in yeast. Appl Microbiol Biotechnol. January; 49(1):66-71, nucleic acids encoding a lanosterol C14-demethylase (ERG11) (Kalb V F, Loper J C, Dey C R, Woods C W, Sutter T R (1986) Isolation of a cytochrome P-450 structural gene from *Saccharomyces cerevisiae*. Gene 45(3): 237-45, nucleic acids encoding a squalene synthetase (ERG9) (Jennings, S. M., (1991): Molecular cloning and characterization of the yeast gene for squalene synthetase. Proc Natl Acad Sci USA. July 15; 88(14):6038-42), nucleic acids encoding a sterol acyltransferase (SAT1) and (SAT2) (Yang, H.: Sterol esterification in yeast: a two-gene process. Science. 1996 May 31; 272(5266):1353-6.) and a further sterol acyltransferase (J. Biol. Chem. 1996, Sep. 27; 271(39):24157-63), nucleic acids encoding a squalene epoxidase (ERG1) (Jandrositz, A., et al (1991) The gene encoding squalene epoxidase from *Saccharomyces cerevisiae*: cloning and characterization. Gene 107:155-160), nucleic acids encoding a C24-methyltransferase (ERG6) (Hardwick, K. G. et al.: SED6 is identical to ERG6, and encodes a putative methyltransferase required for ergosterol synthesis. Yeast. February; 10(2):265-9) and nucleic acids encoding a Delta22-desaturase (ERG5) (Skaggs, B. A. et al,: Cloning and characterization of the *Saccharomyces cerevisiae* C-22 sterol desaturase gene, encoding a second cytochrome P-450 involved in ergosterol biosynthesis, Gene. 1996 Feb. 22; 169(1):105-9.).

Furthermore, methods are known whose aim is an increase in the content of specific intermediates and final products of the sterol metabolism in yeasts and fungi.

EP 486 290 discloses that the content of squalene and other specific sterols such as, for example, zymosterol, in yeasts can be increased by increasing the rate of expression of HMG-CoA reductase and simultaneously interrupting the metabolic pathway of zymosterol C24-methyltransferase (ERG6) and ergosta-5,7,24(28)-trienol 22-dehydrogenase (ERG5).

From T. Polakowski, Molekularbiologische Beeinflussung des Ergosterolstoffwechsels der Hefe *Saccharomyces cerevisiae* [Influencing the ergosterol metabolism of the yeast *Saccharomyces cerevisiae* by molecular biological means], Shaker Verlag Aachen, 1999, pages 59 to 66, it is known that increasing the rate of expression of HMG-CoA reductase alone, without interrupting the downstream metabolic flow as in EP 486 290, merely leads to a slight increase in the content of early sterols and of squalene, while the content of later sterols such as ergosterol does not change substantially and, in the case of ergosterol, even tendentially decreases.

WO 99/16886 describes a method for preparing ergosterol in yeasts which overexpress a combination of genes tHMG, ERG9, SAT1 and ERG1.

Tainaka et al., J, Ferment. Bioeng. 1995, 79, 64-66, further describe that overexpression of ERG11 (lanosterol C14-demethylase) leads to accumulation of 4,4-dimethylzymosterol but not of ergosterol. Compared to the wild type, the transformant showed an increase in the zymosterol content by a factor of from 1.1 to 1.47, depending on fermentation conditions.

Avruch et al, Can. J. Biochem 1976, 54(7), 657-665 and Xu et al, Biochem. Biophys. Res. Commun. 1988, 155(1), 509-517 describe that it is possible to detect, apart from zymosterol, also traces of cholesterol by specifically inhibiting C24-methyltransferase and also by a mutation in the gene locus erg6 in *S. cerevisiae*.

It is an object of the present invention to provide a method for preparing 7-dehydrocholesterol and/or the biosynthetic intermediates and/or secondary products thereof, which method has advantageous properties such as a higher product yield.

We have found that this object is achieved by a method for preparing 7-dehydrocholesterol and/or the biosynthetic intermediates and/or secondary products thereof, in which organisms are cultured which have, compared to the wild type, an increased activity of at least one of the activities selected from the group consisting of $\Delta 8$-$\Delta 7$-isomerase activity, $\Delta 5$-desaturase activity and $\Delta 24$-reductase activity.

An increased activity compared to the wild type means, in the case of the starting organism not having said activity, that said activity is caused. In the case of the starting organism already having said activity, an increased activity compared to the wild type means an activity increased by a percentage.

$\Delta 8$-$\Delta 7$-Isomerase activity means the enzyme activity of a $\Delta 8$-$\Delta 7$-isomerase, also referred to as $\Delta 8$-$\Delta 7$-sterol isomerase.

A $\Delta 8$-$\Delta 7$-isomerase means a protein which has the enzymic activity of converting zymosterol to cholesta-7,24-dienol.

Accordingly, $\Delta 8$-$\Delta 7$-isomerase activity means the amount of zymosterol converted or the amount of cholesta-7,24-dienol formed by the protein $\Delta 8$-$\Delta 7$-isomerase in a particular time.

In the case of an increased $\Delta 8$-$\Delta 7$-isomerase activity compared to the wild type, thus the amount of zymosterol converted or the amount of cholesta-7,24-dienol formed by the protein $\Delta 8$-$\Delta 7$-isomerase in a particular time is increased in comparison with the wild type.

This increase in $\Delta 8$-$\Delta 7$-isomerase activity is preferably at least 5%, further preferably at least 20%, further preferably at least 50%, further preferably at least 100%, more preferably at least 300%, still more preferably at least 500%, in particular at least 600%, of the $\Delta 8$-$\Delta 7$-isomerase activity of the wild type.

$\Delta 5$-Desaturase activity means the enzyme activity of a $\Delta 5$-desaturase, also referred to as lathosterol 5-desaturase or sterol C5-desaturase.

A $\Delta 5$-desaturase means a protein which has the enzymic activity of converting cholesta-7,24-dienol to cholesta-5,7,24-trienol.

Accordingly, $\Delta 5$-desaturase activity means the amount of cholesta-7,24-dienol converted or the amount of cholesta-5,7,24-trienol formed by the protein $\Delta 5$-desaturase in a particular time.

In the case of an increased $\Delta 5$-desaturase activity compared to the wild type, thus the amount of cholesta-7,24-dienol converted or the amount of cholesta-5,7,24-trienol formed by the protein $\Delta 5$-desaturase in a particular time is increased in comparison with the wild type.

This increase in $\Delta 5$-desaturase activity is preferably at least 5%, further preferably at least 20%, further preferably at least 50%, further preferably at least 100%, more preferably at least 300%, still more preferably at least 500%, in particular at least 600%, of the $\Delta 5$-desaturase activity of the wild type.

$\Delta 24$-Reductase activity means the enzyme activity of a $\Delta 24$-reductase, also referred to as 24-dehydrocholesterol reductase.

A $\Delta 24$-reductase means a protein which has the enzymic activity of converting the double bond between C24 and C25 of cholesterol compounds to a single bond, for example converting cholesta-5,7,24-trienol to 7-dehydrocholesterol or zymosterol to lathosterol or cholesta-7,24-dienol to cholesta-7-enol.

Accordingly, $\Delta 24$-reductase activity means preferably the amount of cholesta-5,7,24-trienol converted or the amount of 7-dehydrocholesterol formed by the protein $\Delta 24$-reductase in a particular time.

In the case of an increased $\Delta 24$-reductase activity compared to the wild type, thus the amount of cholesta-5,7,24-trienol converted or the amount of 7-dehydrocholesterol formed by the protein $\Delta 24$-reductase in a particular time is increased in comparison with the wild type.

This increase in $\Delta 24$-reductase activity is preferably at least 5%, further preferably at least 20%, further preferably at least 50%, further preferably at least 100%, more preferably at least 300%, still more preferably at least 500%, in particular at least 600%, of the $\Delta 24$-reductase activity of the wild type.

A wild type means the corresponding not genetically modified starting organism. Preferably and, in particular in those cases in which the organism or the wild type cannot be classified unambiguously, wild type means a reference organism for increasing the $\Delta 8$-$\Delta 7$-isomerase activity, increasing the $\Delta 5$-desaturase activity, increasing the $\Delta 24$-reductase activity, reducing the C24-methyltransferase activity described below, reducing the $\Delta 22$-desaturase activity described below, increasing the HMG-CoA-reductase activity described below, increasing the lanosterol C14-demethylase activity described below, increasing the squalene-epoxidase activity described below, increasing the squalene-synthetase activity described below and increasing the sterol-acyltransferase activity described below and also for increasing the content of 7-dehydrocholesterol and/or of the biosynthetic intermediates and/or secondary products thereof. This reference organism is preferably the yeast strain *Saccharomyces cerevisiae* AH22.

In the method of the invention, organisms are cultured which, compared to the wild type, have an increased activity of at least one of the activities selected from the group consisting of Δ8-Δ7-isomerase activity, Δ5-desaturase activity and Δ24-reductase activity.

In a preferred embodiment, organisms are cultured which, compared to the wild type, have an increased Δ8-Δ7-isomerase activity, Δ5-desaturase activity or Δ24-reductase activity.

In a particularly preferred embodiment of the method of the invention, the organisms have, compared to the wild type, an increased activity of at least two of the activities selected from the group consisting of Δ8-Δ7-isomerase activity, Δ5-desaturase activity and Δ24-reductase activity.

Particularly preferred combinations are Δ8-Δ7-isomerase activity and Δ5-desaturase activity, increased in comparison to the wild type, Δ8-Δ7-isomerase activity and Δ24-reductase activity, increased in comparison to the wild type, and Δ5-desaturase activity and Δ24-reductase activity, increased in comparison with the wild type.

In a very particularly preferred embodiment of the method of the invention, the organisms have, compared to the wild type, an increased Δ8-Δ7-isomerase activity, Δ5-desaturase activity and Δ24-reductase activity.

The Δ8-Δ7-isomerase activity, Δ5-desaturase activity and Δ24-reductase activity and also the HMG-CoA-reductase activity, lanosterol C14-demethylase activity, squalene-epoxidase activity, squalene-synthetase activity and sterol-acyltransferase activity, which are described below, may be increased independently of one another in various ways, for example by eliminating inhibiting regulatory mechanisms at the expression and protein level or by increasing, compared to the wild type, gene expression of the corresponding nucleic acids, i.e. nucleic acids encoding a Δ8-Δ7-isomerase, Δ5-desaturase, Δ24-reductase, HMG-CoA reductase, lanosterol C14-demethylase, squalene epoxidase, squalene synthetase or sterol acyltransferase.

Likewise, gene expression of the corresponding nucleic acid may be increased compared to the wild type in various ways, for example by inducing the appropriate genes by activators, i.e. by inducing the Δ8-Δ7-isomerase gene, the Δ5-desaturase gene, the Δ24-reductase gene, the HMG-CoA-reductase gene, the lanosterol C14-demethylase gene, the squalene-epoxidase gene, the squalene-synthetase gene or the sterol-acyltransferase gene by activators, or by introducing one or more gene copies of the appropriate nucleic acids, i.e. by introducing one or more nucleic acids encoding a Δ8-Δ7-isomerase, Δ5-desaturase, Δ24-reductase, HMG-CoA reductase, lanosterol C14-demethylase, squalene epoxidase, squalene synthetase or sterol acyltransferase into the organism.

Increasing the gene expression of a nucleic acid encoding a Δ8-Δ7-isomerase, Δ5-desaturase, Δ24-reductase, HMG-CoA reductase, lanosterol C14-demethylase, squalene epoxidase, squalene synthetase or sterol acyltransferase means according to the invention also manipulation of the expression of endogenous Δ8-Δ7-isomerases, Δ5-desaturases, Δ24-reductases, HMG-CoA reductases, lanosterol C14-demethylases, squalene epoxidases, squalene synthetases or sterol acyltransferases, which are intrinsic to the organism, in particular to the yeasts.

This may be achieved, for example, by modifying the promoter DNA sequence of genes coding for Δ8-Δ7-isomerase, Δ5-desaturase, Δ24-reductase, HMG-CoA reductase, lanosterol C14-demethylase, squalene epoxidase, squalene synthetase or sterol acyltransferase. Such a modification which causes an increased rate of expression of the relevant gene may be carried out, for example, by deleting or inserting DNA sequences.

As described above, it is possible to modify expression of the endogenous Δ8-Δ7-isomerase, Δ5-desaturase, Δ24-reductase, HMG-CoA reductase, lanosterol C14-demethylase, squalene epoxidase, squalene synthetase or sterol acyltransferase by applying exogenous stimuli. This may be carried out using particular physiological conditions, i.e. by applying foreign substances.

Furthermore, a modified or increased expression of endogenous Δ8-Δ7-isomerase, Δ5-desaturase, Δ24-reductase, HMG-CoA reductase, lanosterol C14-demethylase, squalene epoxidase, squalene synthetase or sterol acyltransferase genes may be achieved by interaction of a regulatory protein which is not present in the untransformed organism with the promoter of said genes.

A regulator of this type may be a chimeric protein which consists of a DNA-binding domain and a transcriptional activator domain, as described, for example, in WO 96/06166.

In a preferred embodiment, the Δ8-Δ7-isomerase activity is increased compared to the wild type by increasing the gene expression of a nucleic acid encoding a Δ8-Δ7-isomerase.

In a further preferred embodiment, gene expression of a nucleic acid encoding a Δ8-Δ7-isomerase is increased by introducing into the organism one or more nucleic acids encoding a Δ8-Δ7-isomerase.

For this purpose, it is possible to use in principle any Δ8-Δ7-isomerase gene, i.e. any nucleic acid encoding a Δ8-Δ7-isomerase.

In the case of genomic Δ8-Δ7-isomerase nucleic acid sequences from eukaryotic sources, which contain introns, preferably already processed nucleic acid sequences such as the corresponding cDNAs are to be used, if the host organism is unable to or cannot be enabled to express the appropriate Δ8-Δ7-isomerase.

Examples of Δ8-Δ7-isomerase genes are nucleic acids encoding a murine Δ8-Δ7-isomerase (nucleic acid: Seq. ID. No. 1, protein: Seq. ID. No. 2) or a human Δ8-Δ7-isomerase (nucleic acid: Seq. ID. No. 3, protein: Seq. ID. No. 4) (Braverman, N. et al., (1999): Mutations in the gene encoding 3beta-hydroxysteroid-delta8,delta7-isomerase cause X-linked dominant Conradi-Hunermann syndrome, Nat. Genet. 22(3), 291-294), or else nucleic acids encoding proteins which have the activity of a Δ8-Δ7-isomerase, for example due to a broad substrate specificity, such as, for example, nucleic acids encoding a C8-isomerase *Saccharomyces cerevisiae* (ERG2) (Nucleic acid: Seq. ID. No. 5, protein: Seq. ID. No. 6) (Ashman, W. H. et al. (1991): Cloning and disruption of the yeast C-8 sterol isomerase gene. Lipids. August; 26(8):628-32).

In this preferred embodiment, thus at least one further Δ8-Δ7-isomerase gene is present in the transgenic organisms of the invention, compared to the wild type.

The number of Δ8-Δ7-isomerase genes in the transgenic organisms of the invention is at least two, preferably more than two, particularly preferably more than three and very particularly preferably more than five.

All of the nucleic acids mentioned in the description may be, for example, an RNA sequence, DNA sequence or cDNA sequence.

Preferred Δ8-Δ7-isomerase genes are nucleic acids encoding proteins which have a high substrate specificity for zymosterol. Therefore, preference is given in particular to Δ8-Δ7-isomerase genes and to the corresponding Δ8-Δ7-isomerases of mammals and to the functional equivalents thereof.

Accordingly, preference is given to using in the above-described method nucleic acids which encode proteins comprising the amino acid sequence SEQ. ID. NO. 2 or a sequence derived from this sequence by substitution, insertion or deletion of amino acids, which is at least 30%, preferably at least 50%, more preferably at least 70%, still more preferably at least 90%, most preferably at least 95%, identical at the amino acid level with the sequence SEQ. ID. NO. 2, and having the enzymic property of a Δ8-Δ7-isomerase.

The sequence SEQ. ID. NO. 2 represents the amino acid sequence of *Mus musculus* Δ8-Δ7-isomerase.

Further examples of Δ8-Δ7-isomerases and Δ8-Δ7-isomerase genes can readily be found, for example, for various organisms whose genomic sequence is known by comparing the homology of the amino acid sequences or the corresponding backtranslated nucleic acid sequences from databases with the SeQ ID. NO. 2.

The *Homo sapiens* Δ8-Δ7-isomerase (Seq. ID. No. 4), for example, is 74% identical to the *Mus musculus* Δ8-Δ7-isomerase (Seq. ID. No. 2).

Further examples of Δ8-Δ7-isomerases and Δ8-Δ7-isomerase genes can furthermore readily be found for various organisms whose genomic sequence is unknown, for example starting from the sequence SEQ. ID. No. 1, by hybridization techniques and PCR techniques in a manner known per se.

The term "substitution" means in the description the replacement of one or more amino acids by one or more amino acids. Preference is given to carrying out "conservative" replacements in which the replacing amino acid has a similar property to that of the original amino acid, for example replacement of Glu by Asp, Gln by Asn, Val by Ile, Leu by Ile, Ser by Thr.

A deletion is the replacement of an amino acid by a direct bond. Preferred positions for deletions are the polypeptide termini and the linkages between the individual protein domains.

Insertions are introductions of amino acids into the polypeptide chain, with a direct bond formally being replaced by one or more amino acids.

Identity between two proteins means identity of the amino acids over the in each case entire length of the protein, in particular the identity which is calculated by comparison with the aid of the Lasergene software from DNASTAR Inc., Madison, Wis. (USA), using the Clustal method (Higgins D G, Sharp P M. Fast and sensitive multiple sequence alignments on a microcomputer. Comput Appl. Biosci. 1989 April; 5(2):151-1) and setting the following parameters:

| Multiple alignment parameter: | |
|---|---|
| Gap penalty | 10 |
| Gap length penalty | 10 |
| Pairwise alignment parameter: | |
| K-tuple | 1 |
| Gap penalty | 3 |
| Window | 5 |
| Diagonals saved | 5 |

Accordingly, a protein which is at least 30% identical at the amino acid level with the sequence SEQ. ID. NO. 2 means a protein which is at least 30% identical when comparing its sequence with the sequence SEQ. ID. NO. 2, in particular according to the above program algorithm with the above set of parameters.

In a further, particularly preferred embodiment, the Δ8-Δ7-isomerase activity is increased by introducing into organisms nucleic acids which encode proteins comprising the amino acid sequence of *Mus musculus* Δ8-Δ7-isomerase (SEQ. ID. NO. 2).

Suitable nucleic acid sequences can be obtained, for example, by backtranslating the polypeptide sequence according to the genetic code.

Preference is given to using for this those codons which are frequently used according to the organism-specific codon usage. Said codon usage can readily be determined on the basis of computer analyses of other known genes of the organisms in question.

If the protein is to be expressed in yeast, for example, it is often advantageous to use the codon usage of yeast for backtranslation.

In a particularly preferred embodiment, a nucleic acid comprising the sequence SEQ. ID. NO. 1 is introduced into the organism.

The sequence SEQ. ID. NO. 1 represents the *Mus musculus* cDNA which encodes the Δ8-Δ7-isomerase of the sequence SEQ ID NO. 2.

Furthermore, all of the Δ8-Δ7-isomerase genes mentioned above can be prepared in a manner known per se by chemical synthesis from the nucleotide building blocks, for example by fragment condensation of individual overlapping complementary nucleic acid building blocks of the double helix. The chemical synthesis of oligonucleotides may be carried out, for example, in a known manner according to the phosphoramidite method (Voet, Voet, 2nd edition, Wiley Press New York, pages 896-897). Annealing of synthetic oligonucleotides and filling-in of gaps with the aid of the Klenow fragment of DNA polymerase and the ligation reactions and also general cloning methods are described in Sambrook et al. (1989), Molecular cloning: A laboratory manual, Cold Spring Harbor Laboratory Press.

In a preferred embodiment, the Δ5-desaturase activity is increased compared to the wild type by increasing the gene expression of a nucleic acid encoding a Δ5-desaturase.

In a further preferred embodiment, gene expression of a nucleic acid encoding a Δ5-desaturase is increased by introducing into the organism one or more nucleic acids encoding a Δ5-desaturase.

For this purpose, it is possible to use in principle any Δ5-desaturase gene, i.e. any nucleic acid encoding a Δ5-desaturase.

In the case of genomic Δ5-desaturase nucleic acid sequences from eukaryotic sources, which contain introns, preferably already processed nucleic acid sequences such as the corresponding cDNAs are to be used, if the host organism is unable to or cannot be enabled to express the appropriate Δ5-desaturase.

Examples of Δ5-desaturase genes are nucleic acids encoding a murine Δ5-desaturase (nucleic acid: Seq. ID. No. 7, protein: Seq. ID. No. 8) or a human Δ5-desaturase (nucleic acid: Seq. ID. No. 9, protein: Seq. ID. No. 10) (Nishi, S. et al., (2000): cDNA cloning of the mammalian sterol C5-desaturase and the expression in yeast mutant. Biochim. Biophys. Acta, 1490, (1-2), 106-108), or else nucleic acids encoding proteins which have the activity of a Δ5-desaturase, for example due to a broad substrate specificity, such as, for example, nucleic acids encoding a *Saccharomyces cerevisiae* C5-desaturase (ERG3) (nucleic acid: Seq. ID. No. 11, protein: Seq. ID. No. 12), (Arthington, B. A. et al. (1991): Cloning, disruption and sequence of the gene encoding yeast C-5 sterol desaturase. Gene. June 15; 102(1):39-44.).

In this preferred embodiment, thus at least one further Δ5-desaturase gene is present in the transgenic organisms of the invention, compared to the wild type.

The number of Δ5-desaturase genes in the transgenic organisms of the invention is at least two, preferably more than two, particularly preferably more than three and very particularly preferably more than five.

Preferred Δ5-desaturase genes are nucleic acids encoding proteins which have a high substrate specificity for cholesta-7,24-dienol. Therefore, preference is given in particular to Δ5-desaturase genes and to the corresponding Δ5-desaturases of mammals and to the functional equivalents thereof.

Accordingly, preference is given to using in the above-described method nucleic acids which encode proteins comprising the amino acid sequence SEQ. ID. NO. 8 or a sequence derived from this sequence by substitution, insertion or deletion of amino acids, which is at least 30%, preferably at least 50%, more preferably at least 70%, still more preferably at least 90%, most preferably at least 95%, identical at the amino acid level with the sequence SEQ. ID. NO. 8, and having the enzymic property of a Δ5-desaturase.

The sequence SEQ. ID. NO. 8 represents the amino acid sequence of *Mus musculus* Δ5-desaturase.

Further examples of Δ5-desaturase and Δ5-desaturase genes can readily be found, for example, for various organisms whose genomic sequence is known by comparing the homology of the amino acid sequences or the corresponding backtranslated nucleic acid sequences from databases with the SeQ ID. NO. 2.

The *Homo sapiens* Δ5-desaturase (Seq. ID. No. 10), for example, is 84% identical to *Mus musculus* Δ5-desaturase (Seq. ID. No. 8).

Further examples of Δ5-desaturases and Δ5-desaturase genes can furthermore readily be found for various organisms whose genomic sequence is unknown, for example starting from the sequence SEQ. ID. No. 7, by hybridization techniques and PCR techniques in a manner known per se.

Accordingly, a protein which is at least 30% identical at the amino acid level with the sequence SEQ. ID. NO. 8 means a protein which is at least 30% identical when comparing its sequence with the sequence SEQ. ID. NO. 8, in particular according to the above program algorithm with the above set of parameters.

In a further, particularly preferred embodiment, the Δ5-desaturase activity is increased by introducing into organisms nucleic acids which encode proteins comprising the amino acid sequence of *Mus musculus* Δ5-desaturase (SEQ. ID. NO. 8).

Suitable nucleic acid sequences can be obtained, for example, by backtranslating the polypeptide sequence according to the genetic code.

Preference is given to using for this those codons which are frequently used according to the organism-specific codon usage. Said codon usage can readily be determined on the basis of computer analyses of other known genes of the organisms in question.

If the protein is to be expressed in yeast, for example, it is often advantageous to use the codon usage of yeast for backtranslation.

In a particularly preferred embodiment, a nucleic acid comprising the sequence SEQ. ID. NO. 7 is introduced into the organism.

The sequence SEQ. ID. NO. 7 represents the *Mus musculus* cDNA which encodes the Δ5-desaturase of the sequence SEQ ID NO. 8.

Furthermore, all of the Δ5-desaturase genes mentioned above can be prepared in a manner known per se by chemical synthesis from the nucleotide building blocks, for example by fragment condensation of individual overlapping complementary nucleic acid building blocks of the double helix. The chemical synthesis of oligonucleotides may be carried out, for example, in a known manner according to the phosphoramidite method (Voet, Voet, 2nd edition, Wiley Press New York, pages 896-897). Annealing of synthetic oligonucleotides and filling-in of gaps with the aid of the Klenow fragment of DNA polymerase and the ligation reactions and also general cloning methods are described in Sambrook et al. (1989), Molecular cloning: A laboratory manual, Cold Spring Harbor Laboratory Press.

In a preferred embodiment, the Δ24-reductase activity is increased compared to the wild type by increasing the gene expression of a nucleic acid encoding a Δ24-reductase.

In a further preferred embodiment, gene expression of a nucleic acid encoding a Δ24-reductase is increased by introducing into the organism one or more nucleic acids encoding a Δ24-reductase.

For this purpose, it is possible to use in principle any Δ24-reductase gene, i.e. any nucleic acid encoding a Δ24-reductase.

In the case of genomic Δ24-reductase nucleic acid sequences from eukaryotic sources, which contain introns, preferably already processed nucleic acid sequences such as the corresponding cDNAs are to be used, if the host organism is unable to or cannot be enabled to express the appropriate Δ24-reductase.

Examples of Δ24-reductase genes are nucleic acids encoding a murine Δ24-reductase (nucleic acid: Seq. ID. No. 13, protein: Seq. ID. No. 14) or a human Δ24-reductase (nucleic acid: Seq. ID. No. 15, protein: Seq. ID. No. 16) (Waterham, H. R. et al.: Mutations in the 3beta-Hydroxysterol Delta24-Reductase Gene Cause Desmosterolosis, an Autosomal Recessive Disorder of Cholesterol Biosynthesis, Am. J. Hum. Genet. 69 (4), 685-694 (2001)), or else nucleic acids encoding proteins which have the activity of a Δ24-reductase, for example due to a broad substrate specificity, such as, for example, nucleic acids encoding a *Saccharomyces cerevisiae* Δ24-reductase (ERG4) (nucleic acid: Seq. ID. No. 17, protein: Seq. ID. No. 18) (Lai, M. H. et al., (1994): The identification of a gene family in the *Saccharomyces cerevisiae* ergosterol biosynthesis pathway. Gene. March 11; 140(1):41-9).

In this preferred embodiment, thus at least one further Δ24-reductase gene is present in the transgenic organisms of the invention, compared to the wild type.

The number of Δ24-reductase genes in the transgenic organisms of the invention is at least two, preferably more than two, particularly preferably more than three and very particularly preferably more than five.

Preferred Δ24-reductase genes are nucleic acids encoding proteins which have a high substrate specificity for cholesta-5,7,24-trienol. Therefore, preference is given in particular to Δ24-reductase genes and to the corresponding Δ24-reductase of mammals and to the functional equivalents thereof.

Accordingly, preference is given to using in the above-described method nucleic acids which encode proteins comprising the amino acid sequence SEQ. ID. NO. 14 or a sequence derived from this sequence by substitution, insertion or deletion of amino acids, which is at least 30%, preferably at least 50%, more preferably at least 70%, still more preferably at least 90%, most preferably at least 95%, identical at the amino acid level with the sequence SEQ. ID. NO. 14, and having the enzymic property of a Δ24-reductase.

The sequence SEQ. ID. NO. 14 represents the amino acid sequence of *Mus musculus* Δ24-reductase.

Further examples of Δ24-reductases and Δ24-reductase genes can readily be found, for example, for various organisms whose genomic sequence is known by comparing the homology of the amino acid sequences or the corresponding backtranslated nucleic acid sequences from databases with the SeQ ID. NO. 14.

The *Homo sapiens* Δ24-reductase (Seq. ID. No. 16), for example, is 96% identical to *Mus musculus* Δ24-reductase (Seq. ID. No. 14).

Further examples of Δ24-reductases and Δ24-reductase genes can furthermore readily be found for various organisms whose genomic sequence is unknown, for example starting from the sequence SEQ. ID. No. 13, by hybridization techniques and PCR techniques in a manner known per se.

Accordingly, a protein which is at least 30% identical at the amino acid level with the sequence SEQ. ID. NO. 14 means a protein which is at least 30% identical when comparing its sequence with the sequence SEQ. ID. NO. 14, in particular according to the above program algorithm with the above set of parameters.

In a further, particularly preferred embodiment, the Δ24-reductase activity is increased by introducing into organisms nucleic acids which encode proteins comprising the amino acid sequence of *Mus musculus* Δ24-reductase (SEQ. ID. NO. 14).

Suitable nucleic acid sequences can be obtained, for example, by backtranslating the polypeptide sequence according to the genetic code.

Preference is given to using for this those codons which are frequently used according to the organism-specific codon usage. Said codon usage can readily be determined on the basis of computer analyses of other known genes of the organisms in question.

If the protein is to be expressed in yeast, for example, it is often advantageous to use the codon usage of yeast for backtranslation.

In a particularly preferred embodiment, a nucleic acid comprising the sequence SEQ. ID. NO. 13 is introduced into the organism.

The sequence SEQ. ID. NO. 13 represents the *Mus musculus* genomic DNA which encodes the Δ24-reductase of the sequence SEQ ID NO. 14.

Furthermore, all of the Δ24-reductase genes mentioned above can be prepared in a manner known per se by chemical synthesis from the nucleotide building blocks, for example by fragment condensation of individual overlapping complementary nucleic acid building blocks of the double helix. The chemical synthesis of oligonucleotides may be carried out, for example, in a known manner according to the phosphoramidite method (Voet, Voet, 2nd edition, Wiley Press New York, pages 896-897). Annealing of synthetic oligonucleotides and filling-in of gaps with the aid of the Klenow fragment of DNA polymerase and the ligation reactions and also general cloning methods are described in Sambrook et al. (1989), Molecular cloning: A laboratory manual, Cold Spring Harbor Laboratory Press.

In a further preferred embodiment of the method of the invention, organisms are cultured which have, compared to the wild type, a reduced activity of at least one of the activities selected from the group consisting of C24-methyltransferase activity and Δ22-desaturase activity in addition to the above-described genetic modifications.

In a further particularly preferred embodiment, organisms are cultured which have, compared to the wild type, a reduced C24-methyltransferase activity and a reduced Δ22-desaturase activity in addition to the above-described genetic modifications.

A reduced activity means both the reduced and the complete elimination of said activity. Reducing an activity therefore also comprises a reduction in the amount of the corresponding protein in the organism up to a complete absence of the corresponding protein, which can be tested, for example, via missing detectability of the corresponding enzyme activity or missing immunological detectability of the corresponding proteins.

C24-methyltransferase activity means the enzyme activity of a C24-methyltransferase.

A C24-methyltransferase means a protein which has the enzymic activity of converting zymosterol to fecosterol (ergosta-8,24(28)dienol).

Accordingly, C24-methyltransferase activity means the amount of zymosterol converted or the amount of fecosterol formed by the protein C24-methyltransferase in a particular time.

In the case of a reduced C24-methyltransferase activity compared to the wild type, thus the amount of zymosterol converted or the amount of fecosterol formed by the protein C24-methyltransferase in a particular time is reduced in comparison with the wild type.

The C24-methyltransferase activity is reduced preferably to at least 90%, further preferably to at least 70%, further preferably to at least 50%, further preferably to at least 30%, more preferably to at least 10%, still more preferably to at least 5%, in particular to 0%, of the C24-methyltransferase activity of the wild type. Therefore, particular preference is given to eliminating the C24-methyltransferase activity in the organism.

Δ22-desaturase activity means the enzyme activity of a Δ22-desaturase.

A Δ22-desaturase means a protein which has the enzymic activity of converting ergosta-5,7-dienol to ergosta-5,7,22,24-tetraen-3β-ol.

Accordingly, Δ22-desaturase activity means the amount of ergosta-5,7-dienol converted or the amount of ergosta-5,7,22,24-tetraen-3β-ol formed by the protein Δ22-desaturase in a particular time.

In the case of a reduced Δ22-desaturase activity compared to the wild type, thus the amount of ergosta-5,7-dienol converted or the amount of ergosta-5,7,22,24-tetraen-3β-ol formed by the protein Δ22-desaturase in a particular time is reduced in comparison with the wild type.

The Δ22-desaturase activity is reduced preferably to at least 90%, further preferably to at least 70%, further preferably to at least 50%, further preferably to at least 30%, more preferably to at least 10%, still more preferably to at least 5%, in particular to 0%, of the Δ22-desaturase activity of the wild type. Therefore, particular preference is given to eliminating the Δ22-desaturase activity in the organism.

The reduction in C24-methyltransferase activity and/or Δ22-desaturase activity may be carried out independently of one another by different cell-biological mechanisms, for example by inhibiting the corresponding activity at the protein level, for example by adding inhibitors of the corresponding enzymes or by reducing gene expression of the corresponding nucleic acids encoding a C24-methyltransferase or Δ22-desaturase, compared to the wild type.

In a particularly preferred embodiment of the method of the invention, the C24-methyltransferase activity and/or the Δ22-desaturase activity are reduced compared to the wild type by reducing the gene expression of the corresponding nucleic acids encoding a C24-methyltransferase or Δ22-desaturase.

Likewise, gene expression of the nucleic acids encoding a C24-methyltransferase or Δ22-desaturase may be reduced compared to the wild type in various ways, for example by
a) introducing nucleic acid sequences which can be transcribed to an antisense nucleic acid sequence which is capable of inhibiting the C24-methyltransferase activity and/or Δ22-desaturase activity, for example by inhibiting the expression of endogenous C24-methyltransferase and/or Δ22-desaturase activity,
b) overexpression of homologous C24-methyltransferase nucleic acid sequences and/or Δ22-desaturase nucleic acid sequences, which leads to cosuppression,
c) introducing nonsense mutations into the endogene by means of introducing RNA/DNA oligonucleotides into the organism,
d) introducing specific DNA-binding factors, for example factors of the zinc finger transcription factor type, which cause a reduction in gene expression or
e) generating knockout mutants, for example with the aid of T-DNA mutagenesis or homologous recombination.

In a preferred embodiment of the method of the invention, gene expression of the nucleic acids encoding a C24-methyltransferase or Δ22-desaturase is reduced by generating knockout mutants, particularly preferably by homologous recombination.

Therefore, preference is given to using an organism which has no functional C24-methyltransferase gene and/or Δ22-desaturase gene.

In a preferred embodiment, knockout mutants are generated, i.e. the C24-methyltransferase-gene target locus and/or the Δ22-desaturase-gene target locus are deleted with simultaneous integration of an expression cassette containing at least one of the nucleic acids described above or below, which encode a protein whose activity is increased in comparison with the wild type, by homologous recombination.

For this purpose, it is possible to use nucleic acid constructs which, in addition to the expression cassettes described below which contain promoter, coding sequence and, where appropriate, terminator and in addition to a selection marker at the 3' and 5' ends, described below, contain nucleic acid sequences which are identical to nucleic acid sequences at the start and the end of the gene to be deleted.

After selection by recombinase systems, the selection marker may preferably be removed again, for example via loxP signals at the 3' and 5' ends of the selection marker, using a Cre recombinase (Cre-loxP system).

In the preferred organism *Saccharomyces cerevisiae*, the C24-methyltransferase gene is the gene ERG6 (SEQ. ID. NO. 19). SEQ. ID. NO. 20 represents the corresponding *Saccharomyces cerevisiae* C24-methyltransferase (Hardwick, K. G. et al.: SED6 is identical to ERG6, and encodes a putative methyltransferase required for ergosterol synthesis. Yeast. February; 10(2):265-9).

In the preferred organism *Saccharomyces cerevisiae*, the Δ22-desaturase gene is the gene ERG5 (SEQ. ID. NO. 21). SEQ. ID. NO. 22 represents the corresponding *Saccharomyces cerevisiae* Δ22-desaturase (Skaggs, B. A. et al,: Cloning and characterization of the *Saccharomyces cerevisiae* C-22 sterol desaturase gene, encoding a second cytochrome P-450 involved in ergosterol biosynthesis, Gene. 1996 Feb. 22; 169 (1):105-9).

In a further preferred embodiment of the method of the invention, organisms are cultured which have, in addition to the above-described modifications, an increased activity of at least one of the activities selected from the group consisting of HMG-CoA-reductase activity, lanosterol-C14-demethylase activity, squalene-epoxidase activity, squalene-synthetase activity and sterol-acyltransferase activity, compared to the wild type.

HMG-CoA-reductase activity means the enzyme activity of an HMG-CoA reductase (3-hydroxy-3-methylglutaryl-coenzyme-A reductase).

HMG-CoA reductase means a protein which has the enzymic activity of converting 3-hydroxy-3-methylglutaryl-coenzyme A to mevalonate.

Accordingly, HMG-CoA-reductase activity means the amount of 3-hydroxy-3-methylglutaryl-coenzyme A converted or the amount of mevalonate formed by the protein HMG-CoA reductase in a particular time.

In the case of an increased HMG-CoA-reductase activity compared to the wild type, thus the amount of 3-hydroxy-3-methylglutaryl-coenzyme A converted or the amount of mevalonate formed by the protein HMG-CoA reductase in a particular time is increased in comparison with the wild type.

This increase in HMG-CoA-reductase activity is preferably at least 5%, further preferably at least 20%, further preferably at least 50%, further preferably at least 100%, more preferably at least 300%, still more preferably at least 500%, in particular at least 600%, of the HMG-CoA-reductase activity of the wild type.

Lanosterol C14-demethylase activity means the enzyme activity of a lanosterol C14-demethylase.

Lanosterol C14-demethylase means a protein which has the enzymic activity of converting lanosterol to 4,4-dimethylcholesta-8,14,24-trienol.

Accordingly, lanosterol C14-demethylase activity means the amount of lanosterol converted or the amount of 4,4-dimethylcholesta-8,14,24-trienol formed by the protein lanosterol C14-demethylase in a particular time.

In the case of an increased lanosterol C14-demethylase activity compared to the wild type, thus the amount of lanosterol converted or the amount of 4,4-dimethylcholesta-8,14,24-trienol formed by the protein lanosterol C14-demethylase in a particular time is increased in comparison with the wild type.

This increase in lanosterol C14-demethylase activity is preferably at least 5%, further preferably at least 20%, further preferably at least 50%, further preferably at least 100%, more preferably at least 300%, still more preferably at least 500%, in particular at least 600%, of the lanosterol C14-demethylase activity of the wild type.

Squalene-epoxidase activity means the enzyme activity of a squalene epoxidase.

Squalene epoxidase means a protein which has the enzymic activity of converting squalene to squalene epoxide.

Accordingly, squalene-epoxidase activity means the amount of squalene converted or the amount of squalene epoxide formed by the protein squalene epoxidase in a particular time.

In the case of an increased squalene-epoxidase activity compared to the wild type, thus the amount of squalene converted or the amount of squalene epoxide formed by the protein squalene epoxidase in a particular time is increased in comparison with the wild type.

This increase in squalene-epoxidase activity is preferably at least 5%, further preferably at least 20%, further preferably at least 50%, further preferably at least 100%, more preferably at least 300%, still more preferably at least 500%, in particular at least 600%, of the squalene-epoxidase activity of the wild type.

Squalene-synthetase activity means the enzyme activity of a squalene synthetase.

Squalene synthetase means a protein which has the enzymic activity of converting farnesyl-pyrophosphate to squalene.

Accordingly, squalene-synthetase activity means the amount of farnesyl-pyrophosphate converted or the amount of squalene formed by the protein squalene synthetase in a particular time.

In the case of an increased squalene-synthetase activity compared to the wild type, thus the amount of farnesyl-pyrophosphate converted or the amount of squalene formed by the protein squalene synthetase in a particular time is increased in comparison with the wild type.

This increase in squalene-synthetase activity is preferably at least 5%, further preferably at least 20%, further preferably at least 50%, further preferably at least 100%, more preferably at least 300%, still more preferably at least 500%, in particular at least 600%, of the squalene-synthetase activity of the wild type.

Sterol-acyltransferase activity means the enzyme activity of a sterol acyltransferase.

Sterol acyltransferase means a protein which has the enzymic activity of converting 7-dehydrocholesterol to corresponding acetylated 7-dehydrocholesterol.

Accordingly, sterol-acyltransferase activity means the amount of 7-dehydrocholesterol converted or the amount of acetylated 7-dehydrocholesterol formed by the protein sterol acyltransferase in a particular time.

In the case of an increased sterol-acyltransferase activity compared to the wild type, thus the amount of 7-dehydrocholesterol converted or the amount of acetylated 7-dehydrocholesterol formed by the protein sterol acyltransferase in a particular time is increased in comparison with the wild type.

This increase in sterol-acyltransferase activity is preferably at least 5%, further preferably at least 20%, further preferably at least 50%, further preferably at least 100%, more preferably at least 300%, still more preferably at least 500%, in particular at least 600%, of the sterol-acyltransferase activity of the wild type.

In a preferred embodiment, the HMG-CoA-reductase activity is increased compared to the wild type by increasing the gene expression of a nucleic acid encoding an HMG-CoA reductase.

In a particularly preferred embodiment of the method of the invention, gene expression of a nucleic acid encoding an HMG-CoA reductase is increased by introducing into the organism a nucleic acid construct comprising an HMG-CoA reductase-encoding nucleic acid whose expression in said organism is subject to a reduced regulation, in comparison with the wild type.

A reduced regulation in comparison with the wild type means a reduced regulation and, preferably, no regulation at the expression or protein level, in comparison with the above-defined wild type.

The reduced regulation may be achieved preferably by a promoter which is functionally linked with the coding sequence in the nucleic acid construct and which is subject to a reduced regulation in the organism, in comparison with the wild-type promoter.

For example, the medium ADH promoter in yeast is subject only to a reduced regulation and is therefore particularly preferred as promoter in the above-described nucleic acid construct.

This promoter fragment of the ADH12s promoter, also referred to as ADH1 hereinbelow, exhibits nearly constitutive expression (Ruohonen L, Penttila M, Keranen S. (1991) Optimization of *Bacillus* alpha-amylase production by *Saccharomyces cerevisiae*. Yeast. May-June; 7(4):337-462; Lang C, Looman A C. (1995) Efficient expression and secretion of *Aspergillus niger* RH5344 polygalacturonase in *Saccharomyces cerevisiae*. Appl Microbiol Biotechnol. December; 44(1-2):147-56) so that transcriptional regulation no longer proceeds via intermediates of ergosterol biosynthesis.

Other preferred promoters with reduced regulation are constitutive promoters such as, for example, the yeast TEF1 promoter, the yeast GPD promoter or the yeast PGK promoter (Mumberg D, Muller R, Funk M. (1995) Yeast vectors for the controlled expression of heterologous proteins in different genetic backgrounds. Gene. 1995 Apr. 14; 156(1):119-22; Chen CY, Oppermann H, Hitzeman R A. (1984) Homologous versus heterologous gene expression in the yeast, *Saccharomyces cerevisiae*. Nucleic Acids Res. December 11; 12(23): 8951-70).

In a further preferred embodiment, reduced regulation can be achieved by using as an HMG-CoA reductase-encoding nucleic acid a nucleic acid whose expression in the organism is subject to a reduced regulation, in comparison with the orthologous nucleic acid intrinsic to said organism.

Particular preference is given to using as an HMG-CoA reductase-encoding nucleic acid a nucleic acid which encodes only the catalytic region of HMG-CoA reductase (truncated (t-) HMG-CoA reductase). This nucleic acid (t-HMG), described in EP 486 290 and WO 99/16886 encodes only the catalytically active part of HMG-CoA reductase, with the membrane domain responsible for regulation at the protein level missing. This nucleic acid is thus subject to a reduced regulation, in particular in yeast, and leads to an increase in gene expression of HMG-CoA reductase.

In a particularly preferred embodiment, nucleic acids are introduced, preferably via the above-described nucleic acid construct, which encode proteins comprising the amino acid sequence SEQ. ID. NO. 24 or a sequence derived from this sequence by substitution, insertion or deletion of amino acids, which is at least 30% identical at the amino acid level to the sequence SEQ ID. NO. 24, and having the enzymic property of an HMG-CoA reductase.

The sequence SEQ ID NO. 24 is the amino acid sequence of the truncated HMG-CoA reductase (t-HMG).

Further examples of HMG-CoA reductases and thus also of the t-HMG-CoA reductases reduced to the catalytic region or of the coding genes can readily be found, for example, for various organisms whose genomic sequence is known by comparing the homology of the amino acid sequences or of the corresponding backtranslated nucleic acid sequences from databases with the sequence SEQ ID. No. 24.

Further examples of HMG-CoA reductases and thus also of the t-HMG-CoA reductases reduced to the catalytic region and of the coding genes can furthermore readily be found for various organisms whose genomic sequence is unknown by hybridization techniques and PCR techniques in a manner known per se, for example starting from the sequence SEQ ID NO. 23.

Particular preference is given to using as a truncated HMG-CoA reductase-encoding nucleic acid a nucleic acid comprising the sequence SEQ ID NO. 23.

In a particularly preferred embodiment, the reduced regulation is achieved by using as an HMG-CoA reductase-encoding nucleic acid a nucleic acid whose expression in the organism is subject to a reduced regulation, in comparison with the orthologous nucleic acid intrinsic to said organism, and by using a promoter which is subject to a reduced regulation in said organism, in comparison with the wild-type promoter.

In a preferred embodiment, the lanosterol C14-demethylase activity is increased compared to the wild type by increasing the gene expression of a nucleic acid encoding a lanosterol C14-demethylase.

In a further preferred embodiment, gene expression of a nucleic acid encoding a lanosterol C14-demethylase is increased by introducing into the organism one or more nucleic acids encoding a lanosterol C14-demthylase.

For this purpose, it is possible to use in principle any lanosterol C14-demethylase gene (ERG11), i.e. any nucleic acids encoding a lanosterol C14-demethylase. In the case of genomic lanosterol C14-demethylase nucleic acid sequences from eukaryotic sources, which contain introns, already processed nucleic acid sequences such as the corresponding cDNAs are to be used preferably, if the host organism is unable to or cannot be enabled to express the appropriate lanosterol C14-demethylase.

Examples of lanosterol C14-demethylase genes are nucleic acids encoding a lanosterol C14-demethylase of *Saccharomyces cerevisiae* (Kalb V F, Loper J C, Dey C R, Woods C W, Sutter T R (1986) Isolation of a cytochrome P-450 structural gene from *Saccharomyces cerevisiae*. Gene 45(3):237-45), *Candida albicans* (Lamb D C, Kelly D E, Baldwin B C, Gozzo F, Boscott P, Richards W G, Kelly S L (1997) Differential inhibition of *Candida albicans* CYP51 with azole antifungal stereoisomers. FEMS Microbiol Lett 149(1):25-30), *Homo sapiens* (Stromstedt M, Rozman D, Waterman M R. (1996) The ubiquitously expressed human CYP51 encodes lanosterol 14 alpha-demethylase, a cytochrome P450 whose expression is regulated by oxysterols. Arch Biochem Biophys 1996 May 1; 329(1):73-81c) or *Rattus norvegicus*, Aoyama Y, Funae Y, Noshiro M, Horiuchi T, Yoshida Y. (1994) Occurrence of a P450 showing high homology to yeast lanosterol 14-demethylase (P450(14DM)) in the rat liver. Biochem Biophys Res Commun. June 30; 201(3):1320-6).

In this preferred embodiment, thus at least one further lanosterol C14-demethylase gene is present in the transgenic organisms of the invention, compared to the wild type.

The number of C14-demethylase genes in the transgenic organisms of the invention is at least two, preferably more than two, particularly preferably more than three and very particularly preferably more than five.

Preference is given to using in the above-described method nucleic acids which encode proteins comprising the amino acid sequence SEQ. ID. NO. 26 or a sequence derived from this sequence by substitution, insertion or deletion of amino acids, which is at least 30%, preferably at least 50%, more preferably at least 70%, still more preferably at least 90%, most preferably at least 95%, identical at the amino acid level with the sequence SEQ. ID. NO. 26, and having the enzymic property of a lanosterol C14-demethylase.

The sequence SEQ. ID. NO. 26 represents the amino acid sequence of *Saccharomyces cerevisiae* lanosterol C14-demethylase.

Further examples of lanosterol C14-demethylases and lanosterol C14-demethylase genes can readily be found, for example, for various organisms whose genomic sequence is known by comparing the homology of the amino acid sequences or the corresponding backtranslated nucleic acid sequences from databases with the SeQ ID. NO. 26.

Further examples of lanosterol C14-demethylases and lanosterol C14-demethylase genes can furthermore readily be found for various organisms whose genomic sequence is unknown, for example starting from the sequence SEQ. ID. No. 25, by hybridization techniques and PCR techniques in a manner known per se.

Accordingly, a protein which is at least 30% identical at the amino acid level with the sequence SEQ. ID. NO. 26 means a protein which is at least 30% identical when comparing its sequence with the sequence SEQ. ID. NO. 26, in particular according to the above program algorithm with the above set of parameters.

In another preferred embodiment, nucleic acids are introduced into organisms, which encode proteins comprising the amino acid sequence of *Saccharomyces cerevisiae* lanosterol C14-demethylase (SEQ. ID. NO. 26).

Suitable nucleic acid sequences can be obtained, for example, by backtranslating the polypeptide sequence according to the genetic code.

Preference is given to using for this those codons which are frequently used according to the organism-specific codon usage. Said codon usage can readily be determined on the basis of computer analyses of other known genes of the organisms in question.

If the protein is to be expressed in yeast, for example, it is often advantageous to use the codon usage of yeast for the backtranslation.

In a particularly preferred embodiment, a nucleic acid comprising the sequence SEQ. ID. NO. 25 is introduced into the organism.

The sequence SEQ. ID. NO. 25 represents the genomic DNA of *Saccharomyces cerevisiae* (ORF S0001049), which encodes the lanosterol C14-demethylase of the sequence SEQ ID NO. 26.

Furthermore, all of the lanosterol C14-demethylase genes mentioned above can be prepared in a manner known per se by chemical synthesis from the nucleotide building blocks, for example by fragment condensation of individual overlapping complementary nucleic acid building blocks of the double helix. The chemical synthesis of oligonucleotides may be carried out, for example, in a known manner according to the phosphoramidite method (Voet, Voet, 2nd edition, Wiley Press New York, pages 896-897). Annealing of synthetic oligonucleotides and filling-in of gaps with the aid of the Klenow fragment of DNA polymerase and the ligation reactions and also general cloning methods are described in Sambrook et al. (1989), Molecular cloning: A laboratory manual, Cold Spring Harbor Laboratory Press.

In a preferred embodiment, the squalene-epoxidase activity is increased compared to the wild type by increasing the gene expression of a nucleic acid encoding a squalene epoxidase.

In a further preferred embodiment, gene expression of a nucleic acid encoding a squalene epoxidase is increased by introducing into the organism one or more nucleic acids encoding a squalene epoxidase.

For this purpose, it is possible to use in principle any squalene-epoxidase gene (ERG1), i.e. any nucleic acids encoding a squalene epoxidase. In the case of genomic squalene epoxidase nucleic acid sequences from eukaryotic sources, which contain introns, already processed nucleic acid sequences such as the corresponding cDNAs are to be used preferably, if the host organism is unable to or cannot be enabled to express the appropriate squalene epoxidase.

Examples of nucleic acids encoding a squalene epoxidase are nucleic acids encoding a squalene epoxidase of *Saccharomyces cerevisiae* (Jandrositz, A., et al (1991) The gene encoding squalene epoxidase from *Saccharomyces cerevisiae*: cloning and characterization. Gene 107:155-160, of *Mus musculus* (Kosuga K, Hata S, Osumi T, Sakakibara J, Ono T. (1995) Nucleotide sequence of a cDNA for mouse squalene epoxidase, Biochim Biophys Acta, February 21; 1260(3):345-8b), of *Rattus norvegicus* (Sakakibara J, Watanabe R, Kanai Y, Ono T. (1995) Molecular cloning and expression of rat squalene epoxidase. J Biol Chem January 6; 270(1):17-20c) or of *Homo sapiens* (Nakamura Y, Sakakibara J, Izumi T, Shibata A, Ono T. (1996) Transcriptional regulation of squalene epoxidase by sterols and inhibitors in HeLa cells., J. Biol. Chem. 1996, Apr. 5; 271(14):8053-6).

In this preferred embodiment, thus at least one further squalene epoxidase is present in the transgenic organisms of the invention, compared to the wild type.

The number of squalene-epoxidase genes in the transgenic organisms of the invention is at least two, preferably more than two, particularly preferably more than three and very particularly preferably more than five.

Preference is given to using in the above-described method nucleic acids which encode proteins comprising the amino acid sequence SEQ. ID. NO. 28 or a sequence derived from this sequence by substitution, insertion or deletion of amino acids, which is at least 30%, preferably at least 50%, more preferably at least 70%, still more preferably at least 90%, most preferably at least 95%, identical at the amino acid level with the sequence SEQ. ID. NO. 28, and having the enzymic property of a squalene epoxidase.

The sequence SEQ. ID. NO. 28 represents the amino acid sequence of *Saccharomyces cerevisiae* squalene epoxidase.

Further examples of squalene epoxidases and squalene-epoxidase genes can readily be found, for example, for various organisms whose genomic sequence is known by comparing the homology of the amino acid sequences or the corresponding backtranslated nucleic acid sequences from databases with the SeQ ID. NO. 28.

Further examples of squalene epoxidases and squalene-epoxidase genes can furthermore readily be found for various organisms whose genomic sequence is unknown, for example starting from the sequence SEQ. ID. No. 27, by hybridization techniques and PCR techniques in a manner known per se.

In another preferred embodiment, nucleic acids are introduced into organisms, which encode proteins comprising the amino acid sequence of *Saccharomyces cerevisiae* squalene epoxidase (SEQ. ID. NO. 28).

Suitable nucleic acid sequences can be obtained, for example, by backtranslating the polypeptide sequence according to the genetic code.

Preference is given to using for this those codons which are frequently used according to the organism-specific codon usage. Said codon usage can readily be determined on the basis of computer analyses of other known genes of the organisms in question.

If the protein is to be expressed in yeast, for example, it is often advantageous to use the codon usage of yeast for backtranslation.

In a particularly preferred embodiment, a nucleic acid comprising the sequence SEQ. ID. NO. 27 is introduced into the organism.

The sequence SEQ. ID. NO. 27 represents the genomic DNA of *Saccharomyces cerevisiae* (ORF YGR175C), which encodes the squalene epoxidase of the sequence SEQ ID NO. 28.

Furthermore, all of the squalene-epoxidase genes mentioned above can be prepared in a manner known per se by chemical synthesis from the nucleotide building blocks, for example by fragment condensation of individual overlapping complementary nucleic acid building blocks of the double helix. The chemical synthesis of oligonucleotides may be carried out, for example, in a known manner according to the phosphoramidite method (Voet, Voet, 2nd edition, Wiley Press New York, pages 896-897). Annealing of synthetic oligonucleotides and filling-in of gaps with the aid of the Klenow fragment of DNA polymerase and the ligation reactions and also general cloning methods are described in Sambrook et al. (1989), Molecular cloning: A laboratory manual, Cold Spring Harbor Laboratory Press.

In a preferred embodiment, the squalene-synthetase activity is increased compared to the wild type by increasing the gene expression of a nucleic acid encoding a squalene synthetase.

In a further preferred embodiment, gene expression of a nucleic acid encoding a squalene synthetase is increased by introducing into the organism one or more nucleic acids encoding a squalene synthetase.

For this purpose, it is possible to use in principle any squalene-synthetase gene (ERG9), i.e. any nucleic acids encoding a squalene synthetase. In the case of genomic squalene synthetase nucleic acid sequences from eukaryotic sources, which contain introns, already processed nucleic acid sequences such as the corresponding cDNAs are to be used preferably, if the host organism is unable to or cannot be enabled to express the appropriate squalene synthetase.

Examples of nucleic acids encoding a squalene synthetase are nucleic acids encoding a *Saccharomyces cerevisiae* squalene synthetase (ERG9) (Jennings, S. M., (1991): Molecular cloning and characterization of the yeast gene for squalene synthetase. Proc Natl Acad Sci USA. July 15; 88(14):6038-42), nucleic acids encoding a *Botryococcus braunii* Okada squalene synthetase (Devarenne, T. P. et al.: Molecular characterization of squalene synthetase from the green microalga *Botryococcus braunii*, raceB, Arch. Biochem. Biophys. 2000, Jan. 15, 373(2):307-17), nucleic acids encoding a Potato tuber squalene synthetase (Yoshioka H. et al.: cDNA cloning of sesquiter penecyclase and squalene synthase, and expression of the genes in potato tuber infected with *Phytophthora infestans*, Plant. Cell. Physiol. 1999, September; 40(9):993-8) and nucleic acids encoding a *Glycyrrhiza glabra* squalene synthetase (Hayashi, H. et al.: Molecular cloning and characterization of two cDNAs for *Glycyrrhiza glabra* squalene synthase, Biol. Pharm. Bull. 1999, September; 22(9):947-50).

In this preferred embodiment, thus at least one further squalene-synthetase gene is present in the transgenic organisms of the invention, compared to the wild type.

The number of squalene-synthetase genes in the transgenic organisms of the invention is at least two, preferably more than two, particularly preferably more than three and very particularly preferably more than five.

Preference is given to using in the above-described method nucleic acids which encode proteins comprising the amino acid sequence SEQ. ID. NO. 30 or a sequence derived from this sequence by substitution, insertion or deletion of amino acids, which is at least 30%, preferably at least 50%, more preferably at least 70%, still more preferably at least 90%, most preferably at least 95%, identical at the amino acid level with the sequence SEQ. ID. NO. 30, and having the enzymic property of a squalene synthetase.

The sequence SEQ. ID. NO. 30 represents the amino acid sequence of *Saccharomyces cerevisiae* squalene synthetase (ERG9).

Further examples of squalene synthetases and squalene-synthetase genes can readily be found, for example, for various organisms hose genomic sequence is known by comparing the homology of the amino acid sequences or the corresponding backtranslated nucleic acid sequences from databases with the SeQ ID. NO. 30.

Further examples of squalene synthetases and squalene-synthetase genes can furthermore readily be found for various organisms whose genomic sequence is unknown, for example starting from the sequence SEQ. ID. No. 29, by hybridization techniques and PCR techniques in a manner known per se.

In another preferred embodiment, nucleic acids are introduced into organisms, which encode proteins comprising the amino acid sequence of *Saccharomyces cerevisiae* squalene synthetase (SEQ. ID. NO. 30).

Suitable nucleic acid sequences can be obtained, for example, by backtranslating the polypeptide sequence according to the genetic code.

Preference is given to using for this those codons which are frequently used according to the organism-specific codon usage. Said codon usage can readily be determined on the basis of computer analyses of other known genes of the organisms in question.

If the protein is to be expressed in yeast, for example, it is often advantageous to use the codon usage of yeast for the backtranslation.

In a particularly preferred embodiment, a nucleic acid comprising the sequence SEQ. ID. NO. 29 is introduced into the organism.

The sequence SEQ. ID. NO. 29 represents the genomic DNA of *Saccharomyces cerevisiae* (ORF YHR190W), which encodes the squalene synthetase of the sequence SEQ ID NO. 30.

Furthermore, all of the squalene-synthetase genes mentioned above can be prepared in a manner known per se by chemical synthesis from the nucleotide building blocks, for example by fragment condensation of individual overlapping complementary nucleic acid building blocks of the double helix. The chemical synthesis of oligonucleotides may be carried out, for example, in a known manner according to the phosphoramidite method (Voet, Voet, 2nd edition, Wiley Press New York, pages 896-897). Annealing of synthetic oligonucleotides and filling-in of gaps with the aid of the Klenow fragment of DNA polymerase and the ligation reactions and also general cloning methods are described in Sambrook et al. (1989), Molecular cloning: A laboratory manual, Cold Spring Harbor Laboratory Press.

In a preferred embodiment, the sterol-acyltransferase activity is increased compared to the wild type by increasing the gene expression of a nucleic acid encoding a sterol acyltransferase.

In a further preferred embodiment, gene expression of a nucleic acid encoding a sterol acyltransferase is increased by introducing into the organism one or more nucleic acids encoding a sterol acyltransferase.

For this purpose, it is possible to use in principle any sterol-acyltransferase gene (SAT1 or SAT2), i.e. any nucleic acids encoding a sterol acyltransferase. In the case of genomic sterol acyltransferase nucleic acid sequences from eukaryotic sources, which contain introns, already processed nucleic acid sequences such as the corresponding cDNAs are to be used preferably, if the host organism is unable to or cannot be enabled to express the appropriate sterol acyltransferase.

Examples of nucleic acids encoding a sterol acyltransferase are nucleic acids encoding a *Saccharomyces cerevisiae* sterol acyltransferase (SAT1) or (SAT2) (Yang, H.: Sterol esterification in yeast: a two-gene process. Science. 1996 May 31; 272(5266):1353-6), a further nucleic acid encoding a further *Saccharomyces cerevisiae* sterol acyltransferase (J. Biol. Chem. 1996, Sep. 27; 271(39):24157-63), nucleic acids encoding a human sterol acyltransferase (Chang, C. C. et al., Molecular cloning and functional expression of human acyl-coenzyme A:cholesterol acyltransferase cDNA in mutant Chinese hamster ovary cells, J. Biol. Chem. 1993, Oct. 5; 268(28):20747-55) and nucleic acids encoding a murine sterol acyltransferase (Uelmen, P. J.: Tissue-specific expression and cholesterol regulation of acylcoenzyme A:cholesterol acyltransferase (ACAT) in mice. Molecular cloning of mouse ACAT cDNA, chromosomal localization, and regulation of ACAT in vivo and in vitro, J. Biol. Chem. 1995 Nov. 3; 270(44):26192-201).

In this preferred embodiment, thus at least one further sterol-acyltransferase gene is present in the transgenic organisms of the invention, compared to the wild type.

The number of sterol-acyltransferase genes in the transgenic organisms of the invention is at least two, preferably more than two, particularly preferably more than three and very particularly preferably more than five.

Preference is given to using in the above-described method nucleic acids which encode proteins comprising the amino acid sequence SEQ. ID. NO. 32 or SEQ ID NO. 50 or a sequence derived from these sequences by substitution, insertion or deletion of amino acids, which is at least 30%, preferably at least 50%, more preferably at least 70%, still more preferably at least 90%, most preferably at least 95%, identical at the amino acid level with the sequence SEQ. ID. NO. 32 or SEQ. ID. NO. 50, and having the enzymic property of a sterol acyltransferase.

The sequence SEQ. ID. NO. 32 represents the amino acid sequence of *Saccharomyces cerevisiae* sterol acyltransferase SAT1.

The sequence SEQ. ID. NO. 50 represents the amino acid sequence *Saccharomyces cerevisiae* sterol acyltransferase SAT2.

SAT 1 and SAT2 differ from one another by a different substrate specificity.

Further examples of sterol acyltransferases and sterol-acyltransferase genes can readily be found, for example, for various organisms whose genomic sequence is known by comparing the homology of the amino acid sequences or the corresponding backtranslated nucleic acid sequences from databases with the SeQ ID. NO. 32 or 50.

Further examples of sterol acyltransferase and sterol-acyltransferase genes can furthermore readily be found for various organisms whose genomic sequence is unknown, for example starting from the sequence SEQ. ID. No. 31 or 49, by hybridization techniques and PCR techniques in a manner known per se.

In another preferred embodiment, nucleic acids are introduced into organisms, which encode proteins comprising the amino acid sequence of *Saccharomyces cerevisiae* sterol acyltransferase SAT1 (SEQ. ID. NO. 32) or *Saccharomyces cerevisiae* sterol acyltransferase SAT2 (SEQ. ID. NO. 50).

Suitable nucleic acid sequences can be obtained, for example, by backtranslating the polypeptide sequence according to the genetic code.

Preference is given to using for this those codons which are frequently used according to the organism-specific codon usage. Said codon usage can readily be determined on the basis of computer analyses of other known genes of the organisms in question.

If the protein is to be expressed in yeast, for example, it is often advantageous to use the codon usage of yeast for the backtranslation.

In a particularly preferred embodiment, a nucleic acid comprising the sequence SEQ. ID. NO. 31 or 49 is introduced into the organism.

The sequence SEQ. ID. NO. 31 represents the genomic DNA of *Saccharomyces cerevisiae* (ORF YNR019W), which encodes the sterol acyltransferase SAT1 of the sequence SEQ ID NO. 32.

The sequence SEQ. ID. NO. 49 represents the genomic DNA of *Saccharomyces cerevisiae* (ORF YCR048W), which encodes the sterol acyltransferase SAT2 of the sequence SEQ ID NO. 50.

Furthermore, all of the sterol-acyltransferase genes mentioned above can be prepared in a manner known per se by chemical synthesis from the nucleotide building blocks, for example by fragment condensation of individual overlapping complementary nucleic acid building blocks of the double helix. The chemical synthesis of oligonucleotides may be carried out, for example, in a known manner according to the phosphoramidite method (Voet, Voet, 2nd edition, Wiley Press New York, pages 896-897). Annealing of synthetic oligonucleotides and filling-in of gaps with the aid of the Klenow fragment of DNA polymerase and the ligation reactions and also general cloning methods are described in Sambrook et al. (1989), Molecular cloning: A laboratory manual, Cold Spring Harbor Laboratory Press.

According to the invention, organisms mean, for example, bacteria, in particular bacteria of the genus *Bacillus*, *Escherichia coli*, *Lactobacillus* spec. or *Streptomyces* spec., for example yeasts, in particular yeasts of the genus *Saccharomyces cerecisiae*, *Pichia pastoris* or *Klyveromyces* spec.

for example fungi, in particular fungi of the genus *Aspergillus* spec., *Penicillium* spec. or *Dictyostelium* spec.

and also, for example, insect cell lines, which are capable, either as wild type or owing to previous genetic modification, of producing zymosterol and/or the biosynthetic intermediates and/or secondary products thereof.

Particularly preferred organisms are yeasts, in particular those of the species *Saccharomyces cerevisiae*, in particular the yeast strains *Saccharomyces cerevisiae* AH22, *Saccharomyces cerevisiae* GRF, *Saccharomyces cerevisiae* DBY747 and *Saccharomyces cerevisiae* BY4741.

In the case of yeasts as organisms or genetically modified organisms, it is possible, as mentioned above, to increase at least one of the activities selected from the group consisting of Δ8-Δ7-isomerase activity, Δ5-desaturase activity and Δ24-reductase activity by overexpressing the corresponding nucleic acids.

The overexpression may be carried out both homologously by introducing nucleic acids intrinsic to yeast and heterologously by introducing nucleic acids from other organisms, in particular mammals, or natural or artificial variants derived therefrom into the yeast. Preference is given to using mammalian genes in yeasts, since these genes have a better substrate specificity with respect to 7-dehydrocholesterol.

The Δ8-Δ7-isomerase activity, Δ5-desaturase activity, Δ24-reductase activity, C24-methyltransferase activity, Δ22-desaturase activity, HMG-CoA-reductase activity, lanosterol-C14-demethylase activity, squalene-epoxidase activity, squalene-synthetase activity and sterol-acyltransferase activity of the genetically modified organism of the invention and of the reference organism is determined under the following conditions:

The activity of HMG-CoA reductase is determined as described in Th. Polakowski, Molekularbiologische Beeinflussung des Ergosterolstoffwechsels der Hefe *Saccharomyces cerevisiae* [influencing the ergosterol metabolism of the yeast *Saccharomyces cerevisiae* by molecular biological means], Shaker-Verlag, Aachen 1999, ISBN 3-8265-6211-9, beschrieben.

According to this, $10^9$ yeast cells of a 48 h culture are harvested by centrifugation (3500×g, 5 min) and washed in 2 ml of buffer I (100 mM potassium phosphate buffer, pH 7.0). The cell pellet is taken up in 500 µl of buffer 1 (cytosolic proteins) or 2 (100 mM potassium phosphate buffer pH 7.0; 1% Triton X-100) (total proteins), and 1 µl of 500 mM PMSF in isopropanol is added. 500 µl of glass beads (d=0.5 mm) are added to the cells and the cells are disrupted by vortexing 5× for one minute each. The liquid between the glass beads is transferred to a new Eppendorf vessel. Cell debris and membrane components are removed by centrifugation (14000×g; 15 min). The supernatant is transferred to a new Eppendorf vessel and represents the protein fraction.

The activity of HMG-CoA reductase is determined by measuring NADPH+H$^+$ consumption during the reduction of 3-hydroxy-3-methylglutaryl-CoA which is added as substrate.

In a 1000 µl assay mixture, 20 µl of yeast protein isolate are combined with 910 µl of buffer I; 50 µl of 0.1 M DTT and 10 µl of 16 mM NADPH+H$^+$. The mixture is adjusted to 30° C. and measured in a spectrophotometer at 340 nm for 7.5 min. The decrease in NADPH, which is measured over this period, is the rate of degradation without addition of substrate and is taken into account as background.

Subsequently, substrate (10 µl of 30 mM HMG-CoA) is added, and measurement continues for another 7.5 min. The HMG-CoA-reductase activity is calculated by determining the specific rate of NADPH degradation.

The activity of lanosterol C14-demethylase is determined as described in Omura, T and Sato, R. (1964) The carbon monoxide binding pigment in liver microsomes. J. Biol. Chem. 239, 2370-2378. In this assay, the amount of P450 enzyme as holoenzyme with bound heme can be semi-quantified. The (active) holoenzyme (with heme) can be reduced by CO and only the CO-reduced enzyme has an absorption maximum at 450 nm. Thus the absorption maximum at 450 nm is a measure for lanosterol C14-demethylase activity.

The activity is determined by diluting a microsomal fraction (4-10 mg/ml protein in 100 mM potassium phosphate buffer) 1:4 so that the protein concentration used in the assay is 2 mg/ml. The assay is carried out directly in a cuvette.

A spatula tipful of dithionite ($S_2O_4Na_2$) is added to the microsomes. The baseline is recorded in the 380-500 nm region in a spectrophotometer.

Subsequently, approx. 20-30 CO bubbles are passed through the sample. The absorption is then measured in the same region. The absorption level at 450 nm corresponds to the amount of P450 enzyme in the assay mixture.

The activity of squalene epoxidase is determined as described in Leber R, Landl K, Zinser E, Ahorn H, Spok A, Kohlwein S D, Turnowsky F, Daum G. (1998) Dual localization of squalene epoxidase, Erg1p, in yeast reflects a relationship between the endoplasmic reticulum and lipid particles, Mol. Biol. Cell. 1998, February; 9(2):375-86.

In this method, a total volume of 500 µl contains from 0.35 to 0.7 mg of microsomal protein or from 3.5 to 75 µg of lipid-particle protein in 100 mM Tris-HCl, pH 7.5, 1 mM EDTA, 0.1 mM FAD, 3 mM NADPH, 0.1 mM squalene 2,3-epoxidase cyclase inhibitor U18666A, 32 µM [$^3$H] squalene dispersed in 0.005% Tween 80.

The assay is carried out at 30° C. After 10 minutes of pretreatment, the reaction is started by adding squalene and stopped after 15, 30 or 45 min by lipid extraction with 3 ml of chloroform/methanol (2:1 vol/vol) and 750 µl of 0.035% $MgCl_2$.

The lipids are dried under nitrogen and redissolved in 0.5 ml of chloroform/methanol (2:1 vol/vol). For thin layer chromatography, portions are applied to a Silica Gel 60 plate (0.2 mm) and fractionated using chloroform as eluent. The positions containing [$^3$H]2,3-oxidosqualene and [$^3$H]squalene were scraped off and quantified in a scintillation counter.

The Δ8-Δ7-isomerase activity is determined, with a slight modification, as described in Silve S. et al.: Emopamil-binding Protein, a Mammalian Protein That Binds a Series of Structurally Diverse Neuroprotective Agents, Exhibits 8-7 Sterol Isomerase Activity in Yeast. J Biol Chem 1996 Sep. 13; 271(37):22434-40:

Microsomes prepared from a culture volume of 10 ml are incubated in the presence of 75 µM cholesta-8-en-3-ol at 30° C. for 3 h. The sterols are then extracted with 4 times 5 ml of hexane and purified. Aliquots are analyzed by means of GC/MS.

The Δ5-desaturase activity is determined, with slight modification, as described in Nishi, S. et al. (2000): cDNA cloning of the mammalian sterol C5-desaturase and the expression in yeast mutant. Biochim. Biophys. Acta1490(1-2),106-108:

Microsomes prepared from a culture volume of 10 ml are incubated in the presence of 75 µM lathosterol and 2 mM NADH at 30° C. for 3 h. The sterols are then extracted with 4 times 5 ml of hexane and purified. Aliquots are analyzed by means of GC/MS.

The Δ24-reductase activity can be determined as described below:

Microsomes prepared from a culture volume of 10 ml are incubated in the presence of 75 µM cholesta-5,7,24-trienol at 30° C. for 3 h. The sterols are then extracted with 4 times 5 ml of hexane and purified. Aliquots are analyzed by means of GC/MS.

The C24-methyltransferase activity can be determined as described below:

80% of the protein Erg6p (C24-methyltransferase) are detectable in lipid particles in the yeast (Athenstaedt K, Zweytick D, Jandrositz A, Kohlwein S D, Daum G: Identification and characterization of major lipid particle proteins of the yeast Saccharomyces cerevisiae. J. Bacteriol. 1999 October; 181(20):6441-8). The enzyme activity is determined by preparing lipid particles from a culture volume (48 h) of 100 ml (according to a method described in Athenstaedt K, Zweytick D, Jandrositz A, Kohlwein S D, Daum G: Identification and characterization of major lipid particle proteins of the yeast Saccharomyces cerevisiae. J. Bacteriol. 1999 October; 181(20):6441-8).

The protein content is determined by a Biorad enzyme assay and 3 mg of protein are used in a volume of 500 µl for each assay mixture. 50 µM [methyl-$^3$H$_3$]-S-adenosylmethionine and 50 µM zymosterol are added to the assay mixture which is then incubated at 35° C. for 10 min. Subsequently, the same volume (500 µl) of chloroform/methanol (4:1) is added and the sterols are then extracted.

The proportion of zymosterol with incorporated [methyl-$^3$H$_3$]-S-adenosylmethionine can be determined by means of scintillation measurement, since chloroform/methanol extraction extracts only lipid-soluble substances. For quantification, the radioactive decays are likewise determined for 50 µM [methyl-$^3$H$_3$]-S-adenosylmethionine by means of scintillation measurement.

This method is a modification of the method described in Nes W D, Guo D, Zhou W.: Substrate-based inhibitors of the (S)-adenosyl-L-methionine:delta24(25)- to delta24(28)-sterol methyl transferase from Saccharomyces cerevisiae, Arch. Biochem. Biophys. 1997 Jun. 1; 342(1):68-81.

The activity of Δ22-desaturase (ERG5p) can be determined as described below:

Various concentrations of Ergosta-5,7-dienol, purified from S. cerevisiae erg5 mutants (Parks et al, 1985. Yeast sterols.yeast mutants as tools for the study of sterol metabolism. Methods Enzymol. 111:333-346) and 50 µg of dilauroylphosphatidylcholine are mixed and treated with ultrasound until a white suspension is formed. Prepared microsomes are added (1 ml)(3 mg/ml protein). NADPH (1 mM final concentration) is added to the assay mixture to start the enzyme reaction. The mixture is incubated at 37° C. for 20 min. The reaction is stopped by adding 3 ml of methanol and sterols are hydrolyzed by adding 2 ml of 60% (wt/vol) KOH in water. The mixture is incubated at 90° C. for 2 h. After cooling, the mixture is extracted three times with 5 ml of hexane and concentrated in a rotary evaporator. Subsequently, the sterols are silylated with bis(trimethylsilyl)trifluoroacetamide (50 µl in 50 µl toluene) at 60° C. for 1 h. The sterols are analyzed by gas chromatography-mass spectrometry (GC-MS) (for example Model VG 12-250 gas chromatograph-mass spectrometer; VG Biotech, Manchester, United Kingdom). The resultant Δ22-desaturated intermediate can be identified depending on the amount of substrate used. Microsomes which are not incubated with substrate serve as reference.

This method is a modification of the method described in Lamb et al: Purification, reconstitution, and inhibition of cytochrome P-450 sterol delta22-desaturase from the pathogenic fungus Candida glabrata. Antimicrob Agents Chemother. 1999 July; 43(7):1725-8.

The squalene-synthetase activity can be determined as described below:

The assays contain 50 mM MOPS, pH 7.2, 10 mM $MgCl_2$, 1% (v/v) Tween-80, 10% (v/v) 2-propanol, 1 mM DTT, 1 mg/mL BSA, NADPH, FPP (or PSPP) and microsomes (protein content 3 mg) in a total volume of 200 µl in glass tubes. The reaction mixtures containing the radioactive substrate [1-$^3$H]FPP (15-30 mCi/µmol) are incubated at 30° C. for 30 min and one volume of 1:1 (v/v) 40% aqueous KOH:methanol is added to the suspension mixture. Liquid NaCl is added to saturate the solution and 2 ml of naphtha containing 0.5% (v/v) squalene are likewise added.

The suspension is vortexed for 30 s. In each case 1 ml of the naphtha layer is applied to a packed 0.5×6 cm aluminum column (80-200 mesh, Fisher) using a Pasteur pipette. The column has been pre-equilibrated with 2 ml of naphtha containing 0.5% (v/v) squalene. The column is then eluted with 5×1 ml of toluene containing 0.5% (v/v) squalene. Squalene radioactivity is measured in Cytoscint (ICN) scintillation cocktail in a scintillation counter (Beckman).

This method is a modification of the method described in Radisky et al., Biochemistry. 2000 Feb. 22; 39(7):1748-60, Zhang et al. (1993) Arch. Biochem. Biophys. 304, 133-143 and Poulter, C. D. et al. (1989) J. Am. Chem. Soc. 111, 3734-3739.

The sterol-acyltransferase activity can be determined as described below:

A 200 ml main culture is inoculated at 1% strength from a 20 ml preculture which has been incubated for two days and is incubated in complete medium overnight. The cells are harvested and then washed in two volumes of HP buffer (100 mM potassium phosphate buffer, pH 7.4; 0.5 mM EDTA; 1 mM glutathione; 20 µM leupeptin; 64 µM benzamidine; 2 mM PMSF) and resuspended in HP buffer.

After adding 1 g of glass beads, the cells are disrupted by vortexing 8 times for one minute each. The supernatant is ultracentrifuged at 105000×g. The pellet is taken up in 1 ml of ACAT buffer (100 mM potassium phosphate buffer pH7,4; 1 mM glutathione).

The enzyme assay is carried out in a volume of 500 µl. The substrate ergosterol is taken up in 62.5 ml of 0.5×ACAT buffer with vigorous vortexing. 250 µl of this solution are used as substrate in the assay. To this, 20 µl of protein extract, 50 µl of water and 130 µl of 0.5×ACAT buffer are added.

The mixture is incubated at 37° C. for 15 min. Subsequently, 50 µl of 14C-oleoyl-CoA (600000 dpm) are added and the reaction is stopped after one minute by adding 4 ml of chloroform/methanol (2:1). To this, 500 µl of $H_2O$ are added. The phases are separated by briefly centrifuging the suspension at 2000×g. The lower phase is evaporated to dryness in a pear-shaped flask and redissolved in 100 µl of chloroform/methanol (4:1) and applied to a TLC plate (silica gel 60 F254). The TLC is carried out using petroleum ether/diethyl ether/acetic acid 90:10:1 as eluent. The spots of the steryl ester fractions are cut out and the number of radioactive decays is determined in a scintillation column. The enzyme activity can be determined via the amount of sterile ester-bound 14C-oleoyl-CoA molecules.

In a preferred embodiment of the method of the invention 7-dehydrocholesterol and/or the biosynthetic intermediates and/or intermediates thereof are prepared by culturing organisms, in particular yeasts, which have, compared to the wild type, an increased activity of at least one of the activities selected from the group consisting of Δ8-Δ7-isomerase activity, Δ5-desaturase activity and Δ24-reductase activity and which have additionally a reduced activity of at least one of the activities selected from the group consisting of C24-methyltransferase activity and Δ22-desaturase activity and which have additionally an increased HMG-CoA-reductase activity, an increased lanosterol-C14-demethylase activity and an increased squalene-epoxidase activity.

In other preferred embodiments of the method of the invention, 7-dehydrocholesterol and/or the biosynthetic intermediates and/or secondary products thereof are prepared by culturing organisms, in particular yeasts, which have, compared to the wild type, an increased Δ8-Δ7-isomerase activity,
an increased Δ5-desaturase activity,
an increased Δ24-reductase activity,
an increased Δ8-Δ7-isomerase activity and an increased Δ5-desaturase activity,
an increased Δ8-Δ7-isomerase activity and an increased Δ24-reductase activity,
an increased Δ5-desaturase activity and an increased Δ24-reductase activity,
an increased Δ8-Δ7-isomerase activity, an increased Δ5-desaturase activity and an increased Δ24-reductase activity,
an increased Δ8-Δ7-isomerase activity and a reduced C24-methyltransferase activity,
an increased Δ5-desaturase activity and a reduced C24-methyltransferase activity,
an increased Δ24-reductase activity and a reduced C24-methyltransferase activity,
an increased Δ8-Δ7-isomerase activity, an increased Δ5-desaturase activity and a reduced C24-methyltransferase activity,
an increased Δ8-Δ7-isomerase activity, an increased Δ24-reductase activity and a reduced C24-methyltransferase activity,
an increased Δ5-desaturase activity, an increased Δ24-reductase activity and a reduced C24-methyltransferase activity,
an increased Δ8-Δ7-isomerase activity, an increased Δ5-desaturase activity, an increased Δ24-reductase activity and a reduced C24-methyltransferase activity,
an increased Δ8-Δ7-isomerase activity and a reduced Δ22-desaturase activity,
an increased Δ5-desaturase activity and a reduced Δ22-desaturase activity,
an increased Δ24-reductase activity and a reduced Δ22-desaturase activity,
an increased Δ8-Δ7-isomerase activity, an increased Δ5-desaturase activity and a reduced Δ22-desaturase activity,
an increased Δ8-Δ7-isomerase activity, an increased Δ24-reductase activity and a reduced Δ22-desaturase activity,
an increased Δ5-desaturase activity, an increased Δ24-reductase activity and a reduced Δ22-desaturase activity,
an increased Δ8-Δ7-isomerase activity, an increased Δ5-desaturase activity, an increased Δ24-reductase activity and a reduced Δ22-desaturase activity,
an increased Δ8-Δ7-isomerase activity, a reduced Δ22-desaturase activity and a reduced C24-ethyltransferase activity,
an increased Δ5-desaturase activity, a reduced Δ22-desaturase activity and a reduced C24-methyltransferase activity,
an increased Δ24-reductase activity, a reduced Δ22-desaturase activity and a reduced C24-methyltransferase activity,
an increased Δ8-Δ7-isomerase activity, an increased Δ5-desaturase activity, a reduced Δ22-desaturase activity and a reduced C24-methyltransferase activity,
an increased Δ8-Δ7-isomerase activity, an increased Δ24-reductase activity, a reduced Δ22-desaturase activity and a reduced C24-methyltransferase activity,
an increased Δ5-desaturase activity, an increased Δ24-reductase activity, a reduced Δ22-desaturase activity and a reduced C24-methyltransferase activity,
an increased Δ8-Δ7-isomerase activity, an increased Δ5-desaturase activity, an increased Δ24-reductase activity, a reduced Δ22-desaturase activity and a reduced C24-methyltransferase activity,
an increased Δ8-Δ7-isomerase activity and an increased HMG-CoA-reductase activity,
an increased Δ5-desaturase activity and an increased HMG-CoA-reductase activity,
an increased Δ24-reductase activity and an increased HMG-CoA-reductase activity,
an increased Δ8-Δ7-isomerase activity, an increased HMG-CoA-reductase activity and an increased Δ5-desaturase activity,
an increased Δ8-Δ7-isomerase activity, an increased HMG-CoA-reductase activity and an increased Δ24-reductase activity,
an increased Δ5-desaturase activity, an increased HMG-CoA-reductase activity and an increased Δ24-reductase activity,
an increased Δ8-Δ7-isomerase activity, an increased Δ5-desaturase activity, an increased HMG-CoA-reductase activity and an increased Δ24-reductase activity,
an increased Δ8-Δ7-isomerase activity, an increased HMG-CoA-reductase activity and a reduced C24-methyltransferase activity,
an increased Δ5-desaturase activity, an increased HMG-CoA-reductase activity and a reduced C24-methyltransferase activity,
an increased Δ24-reductase activity, an increased HMG-CoA-reductase activity and a reduced C24-methyltransferase activity,
an increased Δ8-Δ7-isomerase activity, an increased Δ5-desaturase activity, an increased HMG-CoA-reductase activity and a reduced C24-methyltransferase activity, an increased Δ8-Δ7-isomerase activity, an increased Δ24-reductase activity, an increased HMG-CoA-reductase activity and a reduced C24-methyltransferase activity, an increased Δ5-desaturase activity, an increased Δ24-reductase activity and a reduced C24-methyltransferase activity, an increased Δ8-Δ7-isomerase activity, an increased Δ5-desaturase activity, an increased Δ24-reductase activity, an increased HMG-CoA-reductase activity and a reduced C24-methyltransferase activity, an increased Δ8-Δ7-isomerase activity, an increased HMG-CoA-reductase activity and a reduced Δ22-desaturase activity, an increased Δ5-desaturase activity, an increased HMG-CoA-reductase activity and a reduced Δ22-desaturase activity, an increased Δ24-reductase activity, an increased HMG-CoA-reductase activity and a reduced Δ22-desaturase activity, an increased Δ8-Δ7-isomerase activity, an increased Δ5-desaturase activity, an increased HMG-CoA-reductase activity and a reduced Δ22-desaturase activity, an increased Δ8-Δ7-isomerase activity, an increased Δ24-reductase activity, an increased HMG-CoA-reductase activity and a reduced Δ22-desaturase activity, an increased Δ5-desaturase activity, an increased Δ24-reductase activity, an increased HMG-CoA-reductase activity and a reduced Δ22-desaturase activity, an increased Δ8-Δ7-isomerase activity, an increased Δ5-desaturase activity, an increased Δ24-reductase activity, an increased HMG-CoA-reductase activity and a reduced Δ22-desaturase activity, an increased Δ8-Δ7-isomerase activity, a reduced Δ22-desaturase activity, an increased HMG-CoA-reductase activity and a reduced C24-methyltransferase activity, an increased Δ5-desaturase activity, a reduced Δ22-desaturase activity, an increased HMG-CoA-reductase activity and a reduced C24-methyltransferase activity, an increased Δ24-reductase activity, a reduced Δ22-desaturase activity, an increased HMG-CoA-reductase activity and a reduced C24-methyltransferase activity, an increased Δ8-Δ7-isomerase activity, an increased Δ5-desaturase activity, a reduced Δ22-desaturase activity, an increased HMG-CoA-reductase activity and a reduced C24-methyltransferase activity, an increased Δ8-Δ7-isomerase activity, an increased Δ24-reductase activity, a reduced Δ22-desaturase activity, an increased HMG-CoA-reductase activity and a reduced C24-methyltransferase activity, an increased Δ5-desaturase activity, an increased Δ24-reductase activity, a reduced Δ22-desaturase activity, an increased HMG-CoA-reductase activity and a reduced C24-methyltransferase activity, an increased Δ8-Δ7-isomerase activity, an increased Δ5-desaturase activity, an increased Δ24-reductase activity, a reduced Δ22-desaturase activity, an increased HMG-CoA-reductase activity and a reduced C24-methyltransferase activity, an increased Δ8-Δ7-isomerase activity and an increased lanosterol-C14-demethylase activity, an increased Δ5-desaturase activity and an increased lanosterol-C14-demethylase activity, an increased Δ24-reductase activity and an increased lanosterol-C14-demethylase activity, an increased Δ8-Δ7-isomerase activity, an increased lanosterol-C14-demethylase activity and an increased Δ5-desaturase activity, an increased Δ8-Δ7-isomerase activity, an increased lanosterol-C14-demethylase activity and an increased Δ24-reductase activity, an increased Δ5-desaturase activity, an increased lanosterol-C14-demethylase activity and an increased Δ24-reductase activity, an increased Δ8-Δ7-isomerase activity, an increased Δ5-desaturase activity, an increased lanosterol-C14-demethylase activity and an increased Δ24-reductase activity, an increased Δ8-Δ7-isomerase activity, an increased lanosterol-C14-demethylase activity and a reduced C24-methyltransferase activity, an increased Δ5-desaturase activity and a reduced C24-methyltransferase activity, an increased Δ24-reductase activity, an increased lanosterol-C14-demethylase activity and a reduced C24-methyltransferase activity, an increased Δ8-Δ7-isomerase activity, an increased Δ5-desaturase activity, an increased lanosterol-C14-demethylase activity and a reduced C24-methyltransferase activity, an increased Δ8-Δ7-isomerase activity, an increased Δ24-reductase activity, an increased lanosterol-C14-demethylase activity and a reduced C24-methyltransferase activity, an increased Δ5-desaturase activity, an increased Δ24-reductase activity, an increased lanosterol-C14-demethylase activity and a reduced C24-methyltransferase activity, an increased Δ8-Δ7-isomerase activity, an increased Δ5-desaturase activity, an increased Δ24-reductase activity, an increased lanosterol-C14-demethylase activity and a reduced C24-methyltransferase activity, an increased Δ8-Δ7-isomerase activity, an increased lanosterol-C14-demethylase activity and a reduced Δ22-desaturase activity, an increased Δ5-desaturase activity, an increased lanosterol-C14-demethylase activity and a reduced Δ22-desaturase activity, an increased Δ24-reductase activity, an increased lanosterol-C14-demethylase activity and a reduced Δ22-desaturase activity, an increased Δ8-Δ7-isomerase activity, an increased Δ5-desaturase activity, an increased lanosterol-C14-demethylase activity and a reduced Δ22-desaturase activity, an increased Δ8-Δ7-isomerase activity, an increased Δ24-reductase activity, an increased lanosterol-C14-demethylase activity and a reduced Δ22-desaturase activity, an increased Δ5-desaturase activity, an increased Δ24-reductase activity, an increased lanosterol-C14-demethylase activity and a reduced Δ22-desaturase activity, an increased Δ8-Δ7-isomerase activity, an increased Δ5-desaturase activity, an increased Δ24-reductase activity, an increased lanosterol-C14-demethylase activity and a reduced Δ22-desaturase activity, an increased Δ8-Δ7-isomerase activity, a reduced Δ22-desaturase activity, an increased lanosterol-C14-demethylase activity and a reduced C24-methyltransferase activity, an increased Δ5-desaturase activity, a reduced Δ22-desaturase activity, an increased lanosterol-C14-demethylase activity and a reduced C24-methyltransferase activity, an increased Δ24-reductase activity, a reduced Δ22-desaturase activity, an increased lanosterol-C14-demethylase activity and a reduced C24-methyltransferase activity, an increased Δ8-Δ7-isomerase activity, an increased Δ5-desaturase activity, a reduced Δ22-desaturase activity, an increased lanosterol-C14-demethylase activity and a reduced C24-methyltransferase activity, an increased Δ8-Δ7-isomerase activity, an increased Δ24-reductase activity, a reduced Δ22-desaturase activity, an increased lanosterol-C14-demethylase activity and a reduced C24-methyltransferase activity, an increased Δ5-desaturase activity, an increased Δ24-reductase activity, a reduced Δ22-desaturase activity, an increased lanosterol-C14-demethylase activity and a reduced C24-methyltransferase activity, an increased Δ8-Δ7-isomerase activity, an increased Δ5-desaturase activity, an increased Δ24-reductase activity, a reduced Δ22-desaturase activity, an increased lanosterol-C14-demethylase activity and a reduced C24-methyltransferase activity, an increased Δ8-Δ7-isomerase activity, an increased lanosterol-C14-demethylase activity and an increased HMG-CoA-reductase activity, an increased Δ5-desaturase activity, an increased lanosterol-C14-demethylase activity and an increased HMG-CoA-reductase activity, an increased Δ24-reductase activity, an increased lanosterol-C14-demethylase activity and an increased HMG-CoA-reductase activity, an increased AB-A7-isomerase activity, an increased HMG-CoA-reductase activity, an increased lanosterol-C14-demethylase activity and an increased Δ5-desaturase activity, an increased Δ8-Δ7-isomerase activity, an increased HMG-CoA-reductase activity, an increased lanosterol-C14-demethylase activity and an increased Δ24-reductase activity, an increased Δ5-desaturase activity, an increased HMG-CoA-reductase activity, an increased lanosterol-C14-demethylase activity and an increased Δ24-reductase activity, an increased Δ8-Δ7-isomerase activity, an increased Δ5-desaturase activity, an increased HMG-CoA-reductase activity, an increased lanosterol-C14-demethylase activity and an increased Δ24-reductase activity, an increased Δ8-Δ7-isomerase activity, an increased HMG-CoA-reductase activity, an increased lanosterol-C14-demethylase activity and a reduced C24-methyltransferase activity, an increased Δ5-desaturase activity, an increased HMG-CoA-reductase activity, an increased lanosterol-C14-demethylase activity and a reduced C24-methyltransferase activity, an increased Δ24-reductase activity, an increased HMG-CoA-reductase activity, an increased lanosterol-C14-demethylase activity and a reduced C24-methyltransferase activity, an increased Δ8-Δ7-isomerase activity, an increased Δ5-desaturase activity, an increased HMG-CoA-reductase activity, an increased lanosterol-C14-demethylase activity and a reduced C24-methyltransferase activity, an increased Δ8-Δ7-isomerase activity, an increased Δ24-reductase activity, an increased HMG-CoA-reductase activity, an increased lanosterol-C14-demethylase activity and a reduced C24-methyltransferase activity, an increased Δ5-desaturase activity, an increased Δ24-reductase activity, an increased lanosterol-C14-demethylase activity and a reduced C24-methyltransferase activity, an increased Δ8-Δ7-isomerase activity, an increased Δ5-desaturase activity, an increased Δ24-reductase activity, an increased HMG-CoA-reductase activity, an increased lanosterol-C14-demethylase activity and a reduced C24-methyltransferase activity, an increased Δ8-Δ7-isomerase activity, an increased HMG-CoA-reductase activity, an increased lanosterol-C14-demethylase activity and a reduced Δ22-desaturase activity, an increased Δ5-desaturase activity, an increased HMG-CoA-reductase activity, an increased lanosterol-C14-demethylase activity and a reduced Δ22-desaturase activity, an increased Δ24-reductase activity, an increased HMG-CoA-reductase activity, an increased lanosterol-C14-demethylase activity and a reduced Δ22-desaturase activity, an increased Δ8-Δ7-isomerase activity, an increased Δ5-desaturase activity, an increased HMG-CoA-reductase activity, an increased lanosterol-C14-demethylase activity and a reduced Δ22-desaturase activity, an increased Δ8-Δ7-isomerase activity, an increased Δ24-reductase activity, an increased HMG-CoA-reductase activity, an increased lanosterol-C14-demethylase activity and a reduced Δ22-desaturase activity, an increased Δ5-desaturase activity, an increased Δ24-reductase activity, an increased HMG-CoA-reductase activity and a reduced Δ22-desaturase activity, an increased Δ8-Δ7-isomerase activity, an increased Δ5-desaturase activity, an increased Δ24-reductase activity, an increased HMG-CoA-reductase activity, an increased lanosterol-C14-demethylase activity and a reduced Δ22-desaturase activity, an increased Δ8-Δ7-isomerase activity, a reduced Δ22-desaturase activity, an increased HMG-CoA-reductase activity, an increased lanosterol-C14-demethylase activity and a reduced C24-methyltransferase activity, an increased Δ5-desaturase activity, a reduced Δ22-desaturase activity, an increased HMG-CoA-reductase activity, an increased lanosterol-C14-demethylase activity and a reduced C24-methyltransferase activity, an increased Δ24-reductase activity, a reduced Δ22-desaturase activity, an increased HMG-CoA-reductase activity, an increased lanosterol-C14-demethylase activity and a reduced C24-methyltransferase activity, an increased Δ8-Δ7-isomerase activity, an increased Δ5-desaturase activity, a reduced Δ22-desaturase activity, an increased HMG-CoA-reductase activity, an increased lanosterol-C14-demethylase activity and a reduced C24-methyltransferase activity, an increased Δ8-Δ7-isomerase activity, an increased Δ24-reductase activity, a reduced Δ22-desaturase activity, an increased HMG-CoA-reductase activity, an increased lanosterol-C14-demethylase activity and a reduced C24-methyltransferase activity, an increased Δ5-desaturase activity, an increased Δ24-reductase activity, a reduced Δ22-desaturase activity, an increased HMG-CoA-reductase activity, an increased lanosterol-C14-demethylase activity and a reduced C24-methyltransferase activity, an increased Δ8-Δ7-isomerase activity, an increased Δ5-desaturase activity, an increased Δ24-reductase activity, a reduced Δ22-desaturase activity, an increased HMG-CoA-reductase activity, an increased lanosterol-C14-demethylase activity and a reduced C24-methyltransferase activity, an increased Δ8-Δ7-isomerase activity, an increased Δ5-desaturase activity, an increased Δ24-reductase activity, a reduced Δ22-desaturase activity, an increased HMG-CoA-reductase activity, an increased lanosterol-C14-demethylase activity and a reduced C24-methyltransferase activity, an increased Δ8-Δ7-isomerase activity, an increased Δ5-desaturase activity, an increased Δ24-reductase activity, a reduced Δ22-desaturase activity, an increased HMG-CoA-reductase activity, an increased lanosterol-C14-demethylase activity, an increased squalene-epoxidase activity and a reduced C24-methyltransferase activity, or an increased Δ8-Δ7-isomerase activity, an increased Δ5-desaturase activity, an increased Δ24-reductase activity, a reduced Δ22-desaturase activity, an increased HMG-CoA-reductase activity, an increased lanosterol-C14-demethylase activity, an increased squalene-epoxidase activity and a reduced C24-methyltransferase activity.

In further particularly preferred embodiments of the method of the invention, 7-dehydrocholesterol and/or the biosynthetic intermediates and/or secondary products thereof are prepared by culturing organisms, in particular yeasts, which have, compared to the wild type, an increased Δ8-Δ7-isomerase activity, an increased Δ5-desaturase activity, an increased Δ24-reductase activity, a reduced Δ22-desaturase activity, an increased HMG-CoA-reductase activity, an increased lanosterol-C14-demethylase activity and an increased squalene-epoxidase activity, an increased Δ8-Δ7-isomerase activity, an increased Δ5-desaturase activity, an increased Δ24-reductase activity, an increased HMG-CoA-reductase activity, an increased lanosterol-C14-demethylase activity, an increased squalene-epoxidase activity and a reduced C24-methyltransferase activity, an increased Δ8-Δ7-isomerase activity, an increased Δ5-desaturase activity, an increased Δ24-reductase activity, a reduced Δ22-desaturase activity, an increased HMG-CoA-reductase activity, an increased lanosterol-C14-demethylase activity, an increased squalene-epoxidase activity and a reduced C24-methyltransferase activity, an increased Δ8-Δ7-isomerase activity, an increased Δ5-desaturase activity, an increased Δ24-reductase activity, a reduced Δ22-desaturase activity, an increased HMG-CoA-reductase activity, an increased lanosterol-C14-demethylase activity, an increased squalene-epoxidase activity, an increased squalene-synthetase activity and a reduced C24-methyltransferase activity, an increased Δ8-Δ7-isomerase activity, an increased Δ5-desaturase activity, an increased Δ24-reductase activity, a reduced Δ22-desaturase activity, an increased HMG-CoA-reductase activity, an increased lanosterol-C14-demethylase activity, an increased squalene-epoxidase activity, an increased sterol-acyltransferase activity and a reduced C24-methyltransferase activity, an increased Δ8-Δ7-isomerase activity, an increased Δ5-desaturase activity, an increased Δ24-reductase activity, a reduced Δ22-desaturase activity, an increased HMG-CoA-reductase activity, an increased lanosterol-C14-demethylase activity, an increased squalene-epoxidase activity, an increased squalene-synthetase activity, an increased sterol-acyltransferase activity and a reduced C24-methyltransferase activity.

Biosynthetic 7-dehydrocholesterol intermediates mean all compounds which appear as intermediates during 7-dehydrocholesterol biosynthesis in the organism used, preferably the compounds mevalonate, farnesyl pyrophosphate, geraniol pyrophosphate, squalene epoxide, 4-dimethylcholesta-8,14,24-trienol, 4,4-dimethylzymosterol, squalene, farnesol, geraniol, lanosterol, zymosterol, lathosterol, cholesta-7,24-dienol and cholesta-5,7,24-trienol.

Biosynthetic secondary products of zymosterol mean all compounds which can be derived biosynthetically from 7-dehydrocholesterol in the organism used, i.e. for which 7-dehydrocholesterol appears as an intermediate. These may be compounds which the organism used produces naturally from 7-dehydrocholesterol, such as, for example, cholesterol or vitamin D3 in mammals. However, they also mean compounds which can be produced in the organism from 7-dehydrocholesterol only by introducing genes and enzyme activities of other organisms for which the starting organism has no orthologous gene.

It is possible, for example, to prepare secondary products from 7-dehydrocholesterol, which are naturally present only in mammals, by introducing mammalian genes into yeast:

Introducing a human or murine nucleic acid encoding a human or murine Δ-7-reductase enables the yeast to produce cholesterol.

Under UV irradiation, vitamin $D_3$ (cholecalciferol) is produced from 7-dehydrocholesterol via provitamin $D_3$ by rearrangement.

Therefore, the biosynthetic secondary products of 7-dehydrocholesterol mean in particular provitamin D3, vitamin $D_3$ (cholecalciferol) and/or cholesterol.

Preferred biosynthetic secondary products are provitamin $D_3$ and in particular vitamin $D_3$.

The compounds prepared in the method of the invention may be used in biotransformations, chemical reactions and for therapeutic purposes, for example for producing vitamin $D_3$ from 7-dehydrocholesterol via UV irradiation, or for producing steroid hormones via biotransformation starting from cholesta-7,24-dienol or cholesta-5,7,24-trienol.

In the inventive method for preparing 7-dehydrocholesterol and/or the biosynthetic intermediates and/or secondary products thereof, the step of culturing the genetically modified organisms, also referred to as transgenic organisms hereinbelow, is preferably followed by harvesting said organisms and isolating 7-dehydrocholesterol and/or the biosynthetic intermediates and/or secondary products thereof from said organisms.

The organisms are harvested in a manner known per se and appropriate for the particular organism. Microorganisms such as bacteria, mosses, yeasts and fungi or plant cells which are cultured in liquid media by fermentation may be removed, for example, by centrifugation, decanting or filtration.

7-Dehydrocholesterol and/or the biosynthetic intermediates and/or secondary products thereof are isolated from the harvested biomass together or each compound is harvested separately in a manner known per se, for example by extraction and, where appropriate, further chemical or physical purification processes such as, for example, precipitation methods, crystallography, thermal separation methods such as rectification methods or physical separation methods such as, for example, chromatography.

The transgenic organisms, in particular yeasts, are preferably prepared either by transforming the starting organisms, in particular yeasts, with a nucleic acid construct containing at least one nucleic acid selected from the group consisting of nucleic acids encoding a Δ8-Δ7-isomerase, nucleic acids encoding a Δ5-desaturase and nucleic acids encoding a Δ24-reductase which are functionally linked with one or more regulatory signals ensuring transcription and translation in organisms. In this embodiment, the transgenic organisms are prepared using a nucleic acid construct.

In a particularly preferred embodiment, the above-described nucleic acid construct additionally contains at least one nucleic acid selected from the group consisting of nucleic acids encoding an HMG-CoA-reductase activity, nucleic acids encoding a lanosterol-C14-demethylase, nucleic acids encoding a squalene epoxidase, nucleic acids encoding a squalene synthetase and nucleic acids encoding a sterol acyltransferase which are functionally linked to one or more regulatory signals ensuring transcription and translation in organisms.

However, the transgenic organisms may also preferably be prepared by transforming the starting organisms, in particular yeasts, with at least one nucleic acid construct selected from the group consisting of nucleic acid constructs containing nucleic acids encoding a Δ8-Δ7-isomerase, nucleic acid construct containing nucleic acids encoding a Δ5-desaturase and nucleic acid construct containing nucleic acids encoding a Δ24-reductase which nucleic acids are in each case functionally linked to one or more regulatory signals ensuring transcription and translation in organisms. In this embodiment, the transgenic organisms are prepared using individual nucleic acid constructs or a combination of nucleic acid constructs.

In a particularly preferred embodiment, the above-described combination of nucleic acid constructs additionally comprises at least one nucleic acid construct selected from the group consisting of nucleic acid construct containing nucleic acids encoding an HMG-CoA-reductase activity, nucleic acid construct containing nucleic acids encoding a lanosterol-C14-demethylase, nucleic acid construct containing nucleic acids encoding a squalene epoxidase, nucleic acid construct containing nucleic acids encoding a squalene synthetase and nucleic acid construct containing nucleic acids encoding a sterol acyltransferase which nucleic acids are in each case functionally linked to one or more regulatory signals ensuring transcription and translation in organisms.

Nucleic acid constructs in which the encoding nucleic acid sequence is functionally linked to one or more regulatory signals ensuring transcription and translation in organisms, in particular in yeasts, are also referred to as expression cassettes hereinbelow.

Examples of nucleic acid constructs containing said expression cassette are vectors and plasmids.

Accordingly, the invention further relates to nucleic acid constructs, in particular nucleic acid constructs functioning as expression cassettes, which contain at least one nucleic acid selected from the group consisting of nucleic acids encoding a Δ8-Δ7-isomerase, nucleic acids encoding a Δ5-desaturase and nucleic acids encoding a Δ24-reductase which are functionally linked to one or more regulatory signals ensuring transcription and translation in organisms.

In a preferred embodiment, said nucleic acid construct additionally comprises at least one nucleic acid selected from the group consisting of nucleic acids encoding an HMG-CoA-reductase activity, nucleic acids encoding a lanosterol-C14-demethylase, nucleic acids encoding a squalene epoxidase, nucleic acids encoding a squalene synthetase and nucleic acids encoding a sterol acyltransferase which are functionally linked to one or more regulatory signals ensuring transcription and translation in organisms.

As an alternative, it is also possible to prepare the transgenic organisms of the invention by transformation with individual nucleic acid constructs or with a combination of nucleic acid constructs, said combination comprising at least one nucleic acid construct selected from the groups A to C A nucleic acid construct comprising nucleic acids encoding a Δ8-Δ7-isomerase, which are functionally linked to one or more regulatory signals ensuring transcription and translation in organisms, B nucleic acid construct comprising nucleic acids encoding a Δ5-desaturase, which are functionally linked to one or more regulatory signals ensuring transcription and translation in organisms and C nucleic acid construct comprising nucleic acids encoding a Δ24-reductase, which are functionally linked to one or more regulatory signals ensuring transcription and translation in organisms, and at least one nucleic acid construct selected from the groups D to H D nucleic acid construct comprising nucleic acids encoding an HMG-CoA reductase, which are functionally linked to one or more regulatory signals ensuring trancription and translation in organisms, E nucleic acid construct comprising nucleic acids encoding a lanosterol C14-demethylase, which are functionally linked to one or more regulatory signals ensuring trancription and translation in organisms, F nucleic acid construct comprising nucleic acids encoding a squalene epoxidase, which are functionally linked to one or more regulatory signals ensuring trancription and translation in organisms, G nucleic acid construct comprising nucleic acids encoding a squalene synthetase, which are functionally linked to one or more regulatory signals ensuring trancription and translation in organisms, H nucleic acid construct comprising nucleic acids encoding a sterol acyltransferase, which are functionally linked to one or more regulatory signals ensuring trancription and translation in organisms.

The regulatory signals preferably contain one or more promoters which ensure transcription and translation in organisms, in particular in yeasts.

The expression cassettes include regulatory signals, i.e. regulatory nucleic acid sequences, which control expression of the coding sequence in the host cell. According to a preferred embodiment, an expression cassette comprises upstream, i.e. at the 5' end of the coding sequence, a promoter and downstream, i.e. at the 3' end, a terminator and, where appropriate, further regulatory elements which are operatively linked to the coding sequence for at least one of the above-described genes located in between.

Operative linkage means the sequential arrangement of promoter, coding sequence, where appropriate, terminator and, where appropriate, further regulatory elements in such a way that each of the regulatory elements can properly carry out its function in the expression of the coding sequence.

The preferred nucleic acid constructs, expression cassettes and plasmids for yeasts and fungi and methods for preparing transgenic yeasts and also the transgenic yeasts themselves are described by way of example below.

A suitable promoter of the expression cassette is in principle any promoter which is able to control the expression of foreign genes in organisms, in particular in yeasts.

Preference is given to using in particular a promoter which is subject to reduced regulation in yeast, such as, for example, the medium ADH promoter.

This promoter fragment of the ADH12s promoter, also referred to as ADH1 hereinbelow, exhibits nearly constitutive expression (Ruohonen L, Penttila M, Keranen S. (1991) Optimization of *Bacillus* alpha-amylase production by *Saccharomyces cerevisiae*. Yeast. May-June; 7(4):337-462; Lang C, Looman A C. (1995) Efficient expression and secretion of *Aspergillus niger* RH5344 polygalacturonase in *Saccharomyces cerevisiae*. Appl Microbiol Biotechnol. December; 44(1-2):147-56) so that transcriptional regulation no longer proceeds via intermediates of ergosterol biosynthesis.

Other preferred promoters with reduced regulation are constitutive promoters such as, for example, the yeast TEF1 promoter, the yeast GPD promoter or the yeast PGK promoter (Mumberg D, Muller R, Funk M. (1995) Yeast vectors for the controlled expression of heterologous proteins in different genetic backgrounds. Gene. 1995 Apr. 14; 156(1):119-22; Chen C Y, Oppermann H, Hitzeman R A. (1984) Homologous versus heterologous gene expression in the yeast, *Saccharomyces cerevisiae*. Nucleic Acids Res. December 11; 12(23): 8951-70).

The expression cassette may also contain inducible promoters, in articular a chemically inducible promoter which can be used to control expression of the nucleic acids encoding a Δ8-Δ7-isomerase, Δ5-desaturase, Δ24-reductase, HMG-CoA-reductase, lanosterol-C14-demethylase, squalene epoxidase, squalene synthetase or sterol acyltransferase in the organism at a particular time.

Promoters of this kind, such as, for example, the yeast CupI promoter (Etcheverry T. (1990) Induced expression using yeast copper metallothionein promoter. Methods Enzymol. 1990; 185:319-29.), the yeast Gal1-10 promoter (Ronicke V, Graulich W, Mumberg D, Muller R, Funk M. (1997) Use of conditional promoters for expression of heterologous proteins in *Saccharomyces cerevisiae*, Methods Enzymol. 283: 313-22) or the yeast Pho5 promoter (Bajwa W, Rudolph H, Hinnen A. (1987) PHO5 upstream sequences confer phosphate control on the constitutive PHO3 gene. Yeast. 1987 March; 3(1):33-42), may be used, for example.

A suitable terminator of the expression cassette is in principle any terminator which is able to control the expression of foreign genes in organisms, in particular in yeasts.

Preference is given to the tryptophan terminator of yeasts (TRP1 terminator).

An expression cassette is preferably prepared by fusing a suitable promoter with the above-described nucleic acids encoding a Δ8-Δ7-isomerase, Δ5-desaturase, Δ24-reductase, HMG-CoA-reductase, lanosterol-C14-demethylase, squalene epoxidase, squalene synthetase or sterol acyltransferase and, where appropriate, a terminator according to common recombination and cloning techniques as described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

The nucleic acids of the invention may be prepared synthetically or obtained naturally or may contain a mixture of synthetic and natural nucleic acid components and may also comprise various heterologous gene sections of various organisms.

As described above, preference is given to synthetic nucleotide sequences with codons which are preferred by yeasts. These codons which are preferred by yeasts may be determined from codons which have the highest frequency in proteins and which are expressed in most of the interesting yeast species.

When preparing an expression cassette, it is possible to manipulate various DNA fragments in order to obtain a nucleotide sequence which expediently can be read in the correct direction and is provided with a correct reading frame. The DNA fragments may be linked to one another by attaching adaptors or linkers to said fragments.

Expediently, the promoter and terminator regions may be provided in the direction of transcription with a linker or polylinker which contains one or more restriction sites for inserting this sequence. Normally, the linker has from 1 to 10, mostly from 1 to 8, preferably from 2 to 6, restriction sites. Generally, the linker is, within the regulatory regions, less than 100 bp, frequently less than 60 bp, but at least 5 bp, in length. The promoter may be both native or homologous and non-native or heterologous to the host organism. The expression cassette preferably includes in the 5'-3' direction of transcription the promoter, a coding nucleic acid sequence or a nucleic acid construct and a region for transcriptional termination. Various termination regions can be exchanged with one another randomly.

It is furthermore possible to use manipulations which provide appropriate restriction cleavage sites or which remove excess DNA or restriction cleavage sites. In those cases for which insertions, deletions or substitutions such as, for example, transitions and transversions are suitable, in vitro mutagenesis, primer repair, restriction or ligation can be used.

In suitable manipulations such as, for example, restriction, "chewing-back" or filling-in of protruding ends to form "blunt ends", complementary fragment ends may be provided for ligation.

The invention further relates to the use of the above-described nucleic acids, the above-described nucleic acid constructs or the above-described proteins for preparing transgenic organisms, in particular yeasts.

Preferably, said transgenic organisms, in particular yeasts, have an increased content of 7-dehydrocholesterol and/or of the biosynthetic intermediates and/or secondary products thereof compared to the wild type.

Therefore, the invention further relates to the use of the above-described nucleic acids or the nucleic acid constructs of the invention for increasing the content of 7-dehydrocholesterol and/or of the biosynthetic intermediates and/or secondary products thereof in organisms.

The above-described proteins and nucleic acids may be used for producing 7-dehydrocholesterol and/or the biosynthetic intermediates and/or secondary products thereof in transgenic organisms.

The transfer of foreign genes into the genome of an organism, in particular of yeast, is referred to as transformation.

For this purpose, methods known per se can be used for transformation, in particular in yeasts.

Examples of suitable methods for transforming yeasts are the LiAC method as described in Schiestl R H, Gietz R D. (1989) High efficiency transformation of intact yeast cells using single stranded nucleic acids as a carrier, Curr Genet. December; 16 (5-6):339-46, electroporation as described in Manivasakam P, Schiestl R H. (1993) High efficiency transformation of *Saccharomyces cerevisiae* by electroporation. Nucleic Acids Res. September 11; 21(18):4414-5, and the preparation of protoplasts, as described in Morgan A J. (1983) Yeast strain improvement by protoplast fusion and transformation, Experientia Suppl. 46:155-66

The construct to be expressed is preferably cloned into a vector, in particular into plasmids which are suitable for transforming yeasts, such as, for example, the vector systems Yep24 (Naumovski L, Friedberg E C (1982) Molecular cloning of eucaryotic genes required for excision repair of UV-irradiated DNA: isolation and partial characterization of the RAD3 gene of *Saccharomyces cerevisiae*. J Bacteriol October; 152(1):323-31), Yep13 (Broach J R, Strathern J N, Hicks J B. (1979) Transformation in yeast: development of a hybrid cloning vector and isolation of the CAN1 gene. Gene. 1979 December; 8(1):121-33), the pRS series of vectors (Centromer and Episomal) (Sikorski R S, Hieter P. (1989) A system of shuttle vectors and yeast host strains designed for efficient manipulation of DNA in *Saccharomyces cerevisiae*. Genetics. May; 122(1):19-27) and the vector systems YCp19 or pYEXBX.

Accordingly, the invention furthermore relates to vectors, in particular plasmids, which comprise the above-described nucleic acids, nucleic acid constructs or expression cassettes.

The invention further relates to a method for preparing genetically modified organisms by functionally introducing an above-described nucleic acid or an above-described nucleic acid construct into the starting organism.

The invention further relates to said genetically modified organisms, the genetic modification increasing at least one of the activities selected from the group consisting of Δ8-Δ7-isomerase activity, Δ5-desaturase activity and Δ24-reductase activity, compared to a wild type.

Preferably, at least one of the activities is increased by increasing the gene expression of at least one nucleic acid selected from the group consisting of nucleic acids encoding a Δ8-Δ7-isomerase, nucleic acids encoding a Δ5-desaturase and nucleic acids encoding a Δ24-reductase.

Preferably, gene expression of the above-described nucleic acids is increased by increasing in the organism the copy number of the nucleic acids encoding a Δ8-Δ7-isomerase, encoding a Δ5-desaturase and/or encoding a Δ24-reductase.

Accordingly, the invention preferably relates to an above-described genetically modified organism which contains two or more nucleic acids encoding a Δ8-Δ7-isomerase and/or two or more nucleic acids encoding a Δ5-desaturase and/or two or more nucleic acids encoding a Δ24-reductase.

In a preferred embodiment, the genetically modified organism has, compared to the wild type, in addition to the above-described genetic modifications a reduced activity of at least one of the activities selected from the group consisting of C24-methyltransferase activity and delta22-desaturase activity.

The reduction of at least one of the activities is preferably caused by reducing, compared to the wild type, gene expression of at least one nucleic acid selected from the group consisting of nucleic acids encoding a C24-methyltransferase and nucleic acids encoding a delta22-desaturase.

A particularly preferred genetically modified organism has, apart from the above-described genetic modifications, no functional C24-methyltransferase gene and/or delta22-desaturase gene.

Particular preference is given to above-mentioned genetically modified organisms in which the genetic modification additionally increases at least one of the activities selected from the group consisting of HMG-CoA-reductase activity, lanosterol-C14-demethylase activity, squalene-epoxidase activity, squalene-synthetase activity and sterol-acyltransferase activity compared to a wild type.

Preferably, at least one of these activities is increased, as mentioned above, by increasing, compared to the wild type, gene expression of at least one nucleic acid selected from the group consisting of nucleic acids encoding an HMG-CoA-reductase activity, nucleic acids encoding a lanosterol-C14-demethylase, nucleic acids encoding a squalene epoxidase, nucleic acids encoding a squalene synthetase and nucleic acids encoding a sterol acyltransferase.

Preferably, gene expression of at least one nucleic acid selected from the group consisting of nucleic acids encoding an HMG-CoA-reductase activity, nucleic acids encoding a lanosterol-C14-demethylase, nucleic acids encoding a squalene epoxidase, nucleic acids encoding a squalene synthetase and nucleic acids encoding a sterol acyltransferase is increased compared to the wild type by increasing in the organism the copy number of at least one nucleic acid selected from the group consisting of nucleic acids encoding an HMG-CoA-reductase activity, nucleic acids encoding a lanosterol-C14-demethylase, nucleic acids encoding a squalene epoxidase, nucleic acids encoding a squalene synthetase and nucleic acids encoding a sterol acyltransferase.

Accordingly, the invention preferably relates to an above-described genetically modified organism which contains two or more of at least one nucleic acid selected from the group consisting of nucleic acids encoding an HMG-CoA-reductase activity, nucleic acids encoding a lanosterol-C14-demethylase, nucleic acids encoding a squalene epoxidase, nucleic acids encoding a squalene synthetase and nucleic acids encoding a sterol acyltransferase.

In particular, the invention preferably relates to a genetically modified organism which contains, in addition to the above-described genetic modifications, two or more nucleic acids encoding an HMG-CoA-reductase and/or two or more nucleic acids encoding a lanosterol-C14-demethylase and/or two or more nucleic acids encoding a squalene epoxidase and/or two or more nucleic acids encoding a squalene synthetase and/or two or more nucleic acids encoding a sterol acyltransferase.

The above-described genetically modified organisms have, compared to the wild type, an increased content of 7-dehydrocholesterol and/or of the biosynthetic intermediates and/or secondary products thereof.

Accordingly, the invention relates to an above-described genetically modified organism which, compared to the wild type, has an increased content of 7-dehydrocholesterol and/or of the biosynthetic intermediates and/or secondary products thereof.

Preferred genetically modified organisms are yeasts or fungi which have been genetically modified according to the invention, in particular yeasts which have been genetically modified according to the invention, in particular the yeast species Saccharomyces cerevisiae which has been genetically modified according to the invention, in particular the genetically modified yeast strains Saccharomyces cerevisiae AH22, Saccharomyces cerevisiae GRF, Saccharomyces cerevisiae DBY747 and Saccharomyces cerevisiae BY4741.

In the scope of the present invention, increasing the content of 7-dehydrocholesterol and/or of the biosynthetic intermediates and/or secondary products thereof preferably means the artificially acquired ability to produce biosynthetically an increased amount of at least one of these compounds mentioned above in the genetically modified organism compared to the genetically unmodified organism.

Accordingly, as mentioned at the beginning, wild type preferably means the genetically unmodified organism, but in particular the reference organism mentioned above.

An increased content of 7-dehydrocholesterol and/or of the biosynthetic intermediates and/or secondary products thereof in comparison with the wild type means in particular the increase in the content of at least one of the abovementioned compounds in the organism by at least 50%, preferably 100%, more preferably 200%, particularly preferably 400%, in comparison with the wild type.

The content of at least one of the mentioned compounds is preferably determined according to analytical methods known per se and preferably refers to those compartments of the organism, in which sterols are produced.

The invention is illustrated by the following examples but is not limited to them:

I. General Experimental Conditions

1. Restriction

Restriction of the plasmids (1 to 10 μg) was carried out in 30 μl reaction mixtures. For this purpose, the DNA was taken up in 24 μl of $H_2O$ and admixed with 3 μl of the appropriate buffer, 1 ml of BSA (bovine serum albumin) and 2 μl of enzyme. The enzyme concentration was 1 unit/μl or 5 units/μl, depending on the amount of DNA. In some cases, 1 μl of RNase was added to the reaction mixture in order to degrade the tRNA. The restriction mixture was incubated at 37° C. for 2 hours. The restriction was monitored using a minigel.

2. Gel Electrophoreses

The gel electrophoreses were carried out in minigel or wide minigel apparatuses. The minigels (approx. 20 ml, 8 pockets) and the wide minigels (50 ml, 15 or 30 pockets) consisted of 1% strength agarose in TAE. The running buffer used was 1×TAE.

After adding 3 µl of stop solution, the samples (10 µl) were applied. λ-DNA cut with HindIII (bands at: 23.1 kb; 9.4 kb; 6.6 kb; 4.4 kb; 2.3 kb; 2.0 kb; 0.6 kb) served as standard. For fractionation, a voltage of 80 V was applied for 45 to 60 min. Thereafter, the gel was stained in ethidium bromide solution and documented under UV light using the INTAS video documentation system or photographed using an orange filter.

3. Gel Elution

The desired fragments were isolated by means of gel elution. The restriction mixture was applied to several pockets of a minigel and fractionated. Only λ-HindIII and a "sacrifice lane" were stained in ethidium bromide solution, examined under UV light, and the desired fragment was marked. This prevented the DNA of the remaining pockets from being damaged by ethidium bromide and UV light. Putting the stained and unstained gel slices side by side made it possible to excise the desired fragment from the unstained gel slice on the basis of the marking. The agarose slice with the fragment to be isolated was introduced into a dialysis tube, sealed in air-bubble-free together with a small amount of TAE buffer and introduced into the BioRad minigel apparatus. The running buffer was 1×TAE and the voltage was 100 V for 40 min. Afterward, the polarity was switched for 2 min in order to redissolve DNA sticking to the dialysis tube. The buffer in the dialysis tube, which contained the DNA fragments, was transferred to reaction vessels and subjected to ethanol precipitation. For this purpose, 1/10 volume of 3M sodium acetate, tRNA (1 µl per 50 µl of solution) and 2.5 volumes of ice-cold 96% strength ethanol were added to the DNA solution. The mixture was incubated at −20° C. for 30 min and then removed by centrifugation at 12 000 rpm, 4° C., 30 min. The DNA pellet was dried and taken up in 10 to 50 µl of $H_2O$ (depending on the amount of DNA).

4. Klenow Treatment

The Klenow treatment fills in protruding ends of DNA fragments, resulting in blunt ends. Per 1 µg of DNA, the following reaction mixture was pipetted:

| | | |
|---|---|---|
| DNA pellet + 11 µl | | $H_2O$ |
| | +1.5 µl | 10 × Klenow buffer |
| | +1 µl | 0.1 M DTT |
| | +1 µl | nucleotide (dNTP 2 mM) |
| | +1 µl | Klenow polymerase (1 unit/µl) |

The DNA should be from an ethanol precipitation, in order to prevent contaminations from inhibiting the Klenow polymerase. The reaction mixture was incubated at 37° C. for 30 min, and the reaction was stopped by incubating for another 5 min at 70° C. The DNA was recovered from the reaction mixture by ethanol precipitation and taken up in 10 µl of $H_2O$.

5. Ligation

The DNA fragments to be ligated were combined. The final volume of 13.1 µl contained approx. 0.5 µl of DNA with a vector/insert ratio of 1:5. The sample was incubated at 70° C. for 45 seconds, cooled to room temperature (approx. 3 min) and then incubated on ice for 10 min. The ligation buffers were then added: 2.6 µl of 500 mM Tris-HCl pH 7.5 and 1.3 µl of 100 mM $MgCl_2$, followed by incubation on ice for a further 10 min. After adding 1 µl of 500 mM DTT and 1 µl of 10 mM ATP and another 10 min on ice, 1 µl of ligase (1 unit/pl) was added. The whole treatment should be carried out as free from vibrations as possible so that adjoining DNA ends are not separated again. The ligation was carried out at 14° C. over night.

6. Transformation of E. coli

Competent Escherichia coli (E. coli) NM522 cells were transformed with the DNA of the ligation mixture. A reaction mixture containing 50 µg of the pScL3 plasmids and a reaction mixture without DNA were run as positive control and zero control, respectively. For each transformation mixture, 100 µl of 8% PEG solution, 10 µl of DNA and 200 µl of competent cells (E. coli NM522) were pipetted into a benchtop-centrifuge tube. The reaction mixtures were put on ice for 30 min and agitated occasionally.

Then the heat shock was carried out: 1 min at 42° C. For regeneration, 1 ml of LB medium was added to the cells and the suspension was incubated on a shaker at 37° C. for 90 min. In each case, 100 µl of the undiluted reaction mixtures, a 1:10 dilution and a 1:100 dilution were plated on LB+ampicillin plates and incubated at 37° C. over night.

7. Plasmid Isolation from E. coli (Miniprep)

E. coli colonies were grown in 1.5 ml of LB+ampicillin medium in benchtop-centrifuge tubes at 37° C. and 120 rpm over night. On the next day, the cells were removed by centrifugation at 5000 rpm and 4° C. for 5 min and the pellet was taken up in 50 µl of TE buffer. 100 µl of 0.2 N NaOH, 1% SDS solution were added to and mixed with each reaction mixture, and the mixture was put on ice for 5 min (lysis of the cells). Then, 400 µl of Na acetate/NaCl solution (230 µl of $H_2O$, 130 µl of 3 M sodium acetate, 40 µl of 5M NaCl) were added, the reaction mixture was mixed and put on ice for a further 15 min (protein precipitation). After centrifugation at 11 000 rpm for 15 minutes, the supernatant containing the plasmid DNA was transferred to an Eppendorf vessel. If the supernatant was not completely clear, centrifugation was repeated. 360 µl of ice-cold isopropanol were added to the supernatant and the reaction mixture was incubated at −20° C. for 30 min (DNA precipitation). The DNA was removed by centrifugation (15 min, 12 000 rpm, 4° C.), the supernatant was discarded, the pellet was washed in 100 µl of ice-cold 96% strength ethanol, incubated at −20° C. for 15 min and again removed by centrifugation (15 min, 12 000 rpm, 4° C.). The pellet was dried in a SpeedVac and then taken up in 100 µl of $H_2O$. The plasmid DNA was characterized by restriction analysis. For this purpose, 10 µl of each reaction mixture were restriction-digested and fractionated gel-electrophoretically in a wide minigel (see above).

8. Plasmid Preparation from E. coli (Maxiprep)

In order to isolate larger amounts of plasmid DNA, the maxiprep method was carried out. Two flasks with 100 ml of LB+ampicillin medium were inoculated with a colony or with 100 µl of a frozen culture which carries the plasmid to be isolated and incubated at 37° C. and 120 rpm over night. On the next day, the culture (200 ml) was transferred to a GSA beaker and centrifuged at 4000 rpm (2600×g) for 10 min. The cell pellet was taken up in 6 ml of TE buffer. The cell wall was digested by adding 1.2 ml of lysozyme solution (20 mg/ml of TE buffer) and incubated at room temperature for 10 min. Subsequently, the cells were lysed with 12 ml of a 0.2 N NaOH, 1% SDS solution, followed by incubation at room temperature for another 5 min. The proteins were precipitated by adding 9 ml of a cooled 3 M sodium acetate solution (pH 4.8) and incubation on ice for 15 minutes. After centrifugation (GSA: 13 000 rpm (27 500×g), 20 min, 4° C.), the supernatant containing the DNA was transferred to a new GSA beaker and the DNA was precipitated with 15 ml of ice-cold isopropanol and incubation at −20° C. for 30 min. The DNA pellet was washed in 5 ml of ice-cold ethanol and dried in air (approx. 30-60 min). Thereafter, it was taken up in 1 ml of $H_2O$. The plasmid was checked by restriction analysis. The concentration was determined by applying dilutions to a minigel. The salt content was reduced by microdialysis (pore size 0.025 μm) for 30-60 minutes.

9. Transformation of Yeast

For the transformation of yeast, a preculture of the strain *Saccharomyces cerevisiae* AH22 was prepared. A flask containing 20 ml of YE medium was inoculated with 100 μl of the frozen culture and incubated at 28° C. and 120 rpm over night. The main culture was carried out under the same conditions in flasks containing 100 ml of YE medium which was inoculated with 10 μl, 20 μl or 50 μl of the preculture.

9.1 Preparation of Competent Cells

On the next day, the cells in the flasks were counted by means of a Thoma chamber and the flask containing from 3-5×$10^7$ cells/ml was chosen for the subsequent procedure. The cells were harvested by centrifugation (GSA: 5000 rpm (4000×g) 10 min). The cell pellet was taken up in 10 ml of TE buffer and distributed into two benchtop-centrifuged tubes (5 ml each). The cells were removed by centrifugation at 6000 rpm for 3 min and then washed twice with in each case 5 ml of TE buffer. The cell pellet was then taken up in 330 μl of lithium acetate buffer per $10^9$ cells, transferred to a sterile 50 ml Erlenmeyer flask and agitated at 28° C. for one hour. As a result, the cells were competent for transformation.

9.2 Transformation

For each transformation mixture, 15 μl of herring sperm DNA (10 mg/ml), 10 μl of the DNA to be transformed (approx. 0.5 μg) and 330 μl of competent cells were pipetted into a benchtop-centrifuged tube and incubated at 28° C. for 30 min (without agitation). Then, 700 μl of 50% PEG 6000 were added and the suspension was incubated at 28° C. for another hour, without agitation. This was followed by a heat shock at 42° C. for 5 min. 100 μl of the suspension were plated on selection medium (YNB, Difco) in order to select for leucine prototrophy. In the case of selection for G418 resistance, the cells are regenerated after the heat shock (see under 9.3 Regeneration phase).

9.3 Regeneration Phase

Since the selection marker is the resistance to G418, the cells needed time to express the resistance gene. 4 ml of YE medium were added to the transformation mixtures which were then incubated on the shaker (120 rpm) at 28° C. over night. On the next day, the cells were removed by centrifugation (6000 rpm, 3 min), taken up in 1 ml YE medium, and 100 μl or 200 μl thereof were plated on YE+G418 plates. The plates were incubated at 28° C. for several days.

10. PCR Reaction Conditions

The reaction conditions for the polymerase chain reaction must be optimized in each individual case and do not apply absolutely to each reaction mixture. Thus it is possible, inter alia, to vary the amount of DNA used, the salt concentrations and the melting temperature. For our task, it proved advantageous to combine in an Eppendorf vessel which was suitable for use in a thermocycler the following substances: 5 μl of Super buffer, 8 μl of dNTPs (0.625 μM each), 5' primer, 3' primer and 0.2 μg of template DNA, dissolved in enough water so as to result in a total volume of 50 μl for the PCR reaction mixture, were added to 2 μl of (=0.1 U) Super Taq polymerase. The reaction mixture was briefly centrifuged and overlaid with a drop of oil. Between 37 and 40 cycles were chosen for amplification.

II. EXAMPLES

Example 1

Expression and overexpression of a truncated HMG-CoA reductase, a squalene epoxidase (ERG1) and/or a lanosterol-C14-demethylase (ERG11), partially with deletion of ERG5 and ERG6 in *S. cerevisiae* GRF18 and GRFura3, respectively.

1.1 Preparation of the Plasmids pFlat1 and pFlat3 and pFlat4

The expression vector pFlat3 was prepared by linearizing the plasmid YEp24 (Naumovski L, Friedberg E C (1982) Molecular cloning of eucaryotic genes required for excision repair of UV-irradiated DNA: isolation and partial characterization of the RAD3 gene of *Saccharomyces cerevisiae*. J Bacteriol October; 152(1):323-31) via restriction with SphI and a 900 bp SphI fragment of the vector pPT2B (Lang C, Looman A C. (1995) Efficient expression and secretion of *Aspergillus niger* RH5344 polygalacturonase in *Saccharomyces cerevisiae*. Appl Microbiol Biotechnol. December; 44(1-2): 147-56) which contains the ADH1 promoter and the TRP1 terminator of the yeast *Saccharomyces cerevisiae* and a multiple-cloning site of the vector pUC19 (Yanisch-Perron C, Vieira J, Messing J. (1985) Improved M13 phage cloning vectors and host strains: nucleotide sequences of the M13 mp18 and pUC19 vectors. Gene. 1985; 33(1): 103-19.) was integrated.

The multiple-cloning site was extended by a polylinker containing the restriction sites NotI and XhoI. The polylinker was integrated via the SalI cleavage site of the vector. The resulting plasmid is denoted pFlat1.

The vector pFlat3 was prepared by linearizing the vector pFlat1 by the enzyme NcoI and blunt-ending it by means of Klenow treatment. This was followed by integrating a BamHI fragment which had been blunt-ended by means of Klenow-polymerase treatment and which contains the yeast LEU2 gene and originates from the plasmid YDpL (Berben, G., Dumont, J., Gilliquet, V., Bolle, P. A. and Hilger F. (1991) The YDp Plasmids: a Uniform Set of Vectors Bearing Versatile Disruption Cassettes for *Saccharomyces cerevisiae*. Yeast 7: 475-477.).

The vector pFlat4 was prepared by linearizing the vector pFlat1 by the enzyme NcoI and blunt-ending it by means of Klenow treatment. This was followed by integrating a BamHI fragment which had been blunt-ended by means of Klenow-polymerase treatment and which contains the yeast HIS3 gene and originates from plasmid YDpH (Berben et al., 1991).

1.2 Integration of ERG1, ERG11, ERG4, ERG2 or ERG3 or of the Δ24-Reductase Gene into the Vectors pFLat1, pFlat3 and pFlat4

Figure 7:
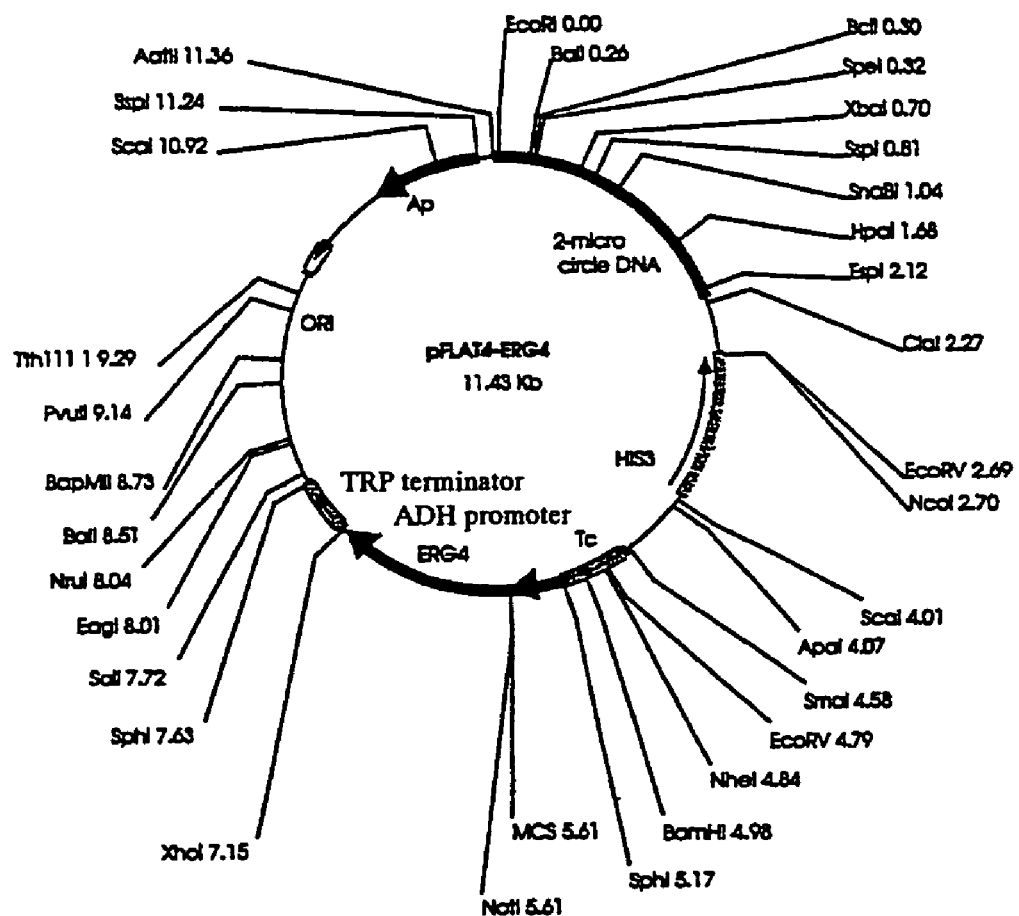

First, a NotI restriction cleavage site was inserted at the 5'-coding side of the genes ERG1, ERG11, ERG4, delta24-reductase, ERG2 or ERG3 and an XhoI restriction cleavage site was inserted at the 3'-coding side of said genes by means of PCR and the corresponding coding regions were amplified. Subsequently, the amplicons were treated with the restriction enzymes NotI and XhoI. The plasmids pFlat1, pFlat3 and pFlat4 were treated in parallel with enzymes NotI and XhoI. The cleaved amplicons were then integrated into the cleaved plasmids via ligation using T4 ligase. FIG. 7 depicts as an example the plasmid pFLAT-3-ERG4.

Primer sequences for cloning ERG1, ERG11, ERG2, ERG3, ERG4, delta24-reductase:

```
Primer ERG1-5' (SEQ. ID. No. 51):
CTGCGGCCGC ATCATGTCTG CTGTTAACGT TGC

Primer ERG1-3' (SEQ. ID. No. 52):
TTCTCGAGTT AACCAATCAA CTCACCAAAC

Primer ERG11-5' (SEQ. ID. No. 53):
CTGCGGCCGCAGGATGTCTGCTACCAAGTCAATCG

Primer ERG11-3' (SEQ. ID. No. 54):
ATCTCGAGCTTAGATCTTTTGTTCTGGATTTCTC

Primer ERG2-5' (SEQ. ID. No. 55):
CTGCGGCCGCACCATGAAGTTTTTCCCACT CC

Primer ERG2-3' (SEQ. ID. No. 56):
TTCTCGAGTTAGAACTTTTTGTTTTGCAACAAG

Primer ERG3-5' (SEQ. ID. No. 57):
CTGCGGCCGCAATATGGATTTGGTCTTAGAAGTCG

Primer ERG3-3' (SEQ. ID. No. 58):
AACTCGAGTCAGTTGTTCTTCTTGGTATTTG

Primer ERG4-5' (SEQ. ID. No. 59):
CTGCGGCCGCACTATGGCAAAGGATAATAGTGAG

Primer ERG4-3' (SEQ. ID. No. 60):
TTCTCGAGCTAGAAAACATAAGGAATAAAGAC

Primer Δ24R-5' (SEQ. ID. No. 47):
CTGCGGCCGCAAGATGGAGCCCGCCGTGTCGC

Primer Δ24R-3' (SEQ. ID. No. 48)
AACTCGAGTCAGTGCCTTGCCGCCTTGC
```

1.3 Preparation of the Integration Vectors pUG6-tHMG, pUG6-ERG1, pUG6-ERG11

1.3.1 pUG6-tHMG

The DNA sequence for the expression cassette composed of ADH1-promoter-tHMG-tryptophan-terminator was isolated from the vector YepH2 (Polakowski, T., Stahl, U., Lang, C. (1998): Overexpression of a cytosolic HMG-CoA reductase in yeast leads to squalene accumulation. Appl. Microbiol. Biotechnol. 49: 66-71) by restriction with the enzymes EcoRV and Bsp68I (NruI) by using standard methods. The DNA fragment obtained was cloned with blunt ends into the EcoRV cleavage site of the vector pUG6 (Güldener, U et al. (1996): A new efficient gene disruption cassette for repeated use in budding yeast, Nucleic Acids Res. July 1; 24(13):2519-24), resulting in the vector denoted pUG6-tHMG (FIG. 1).

1.3.2 pUG6-ERG1

Figure 2:
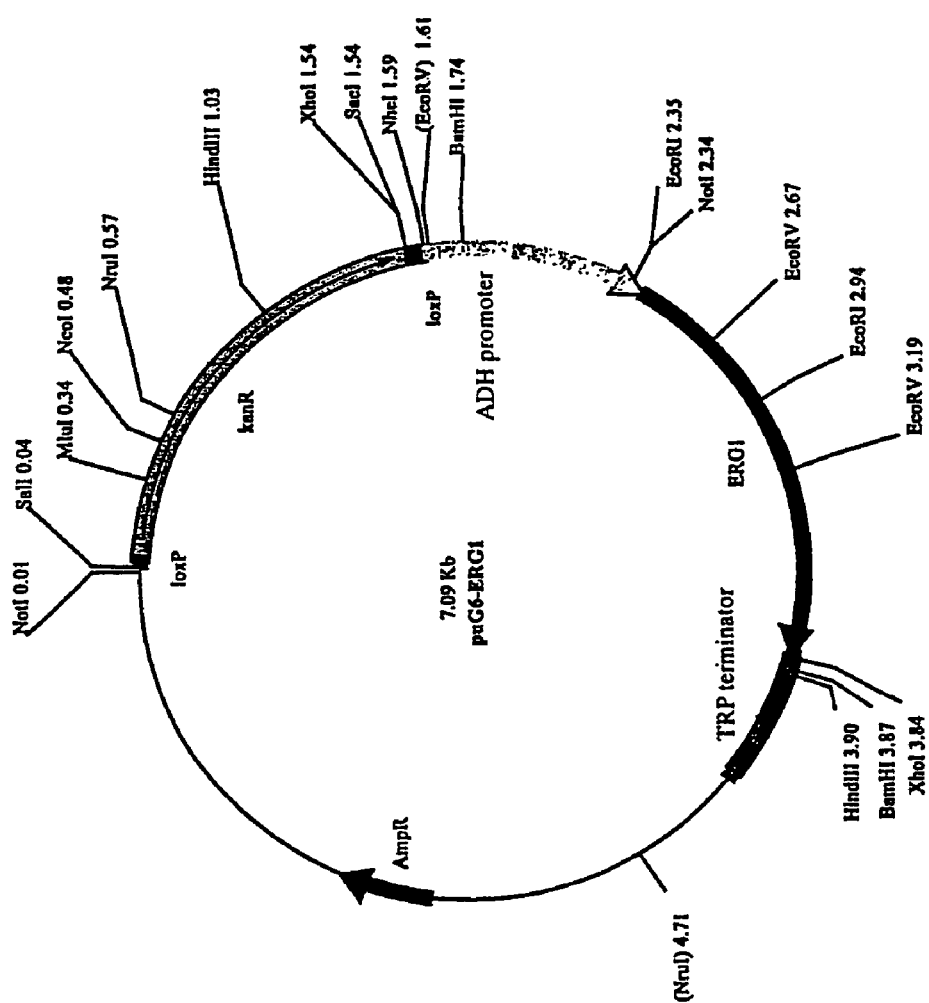

The DNA sequence for the expression cassette composed of ADH1-promoter-ERG1-tryptophan-terminator was isolated from the vector pFlat3-ERG1 by restriction with the enzymes NheI and Bsp68I (NruI), using standard methods. After Klenow treatment, the DNA fragment obtained was cloned with blunt ends into the EcoRV cleavage site of the vector pUG6 (Güldener, U et al. (1996): A new efficient gene disruption cassette for repeated use in budding yeast, Nucleic Acids Res. July 1; 24(13):2519-24), resulting in the vector denoted pUG6-ERG1 (FIG. 2).

1.3.3 pUG6-ERG11

Figure 3:
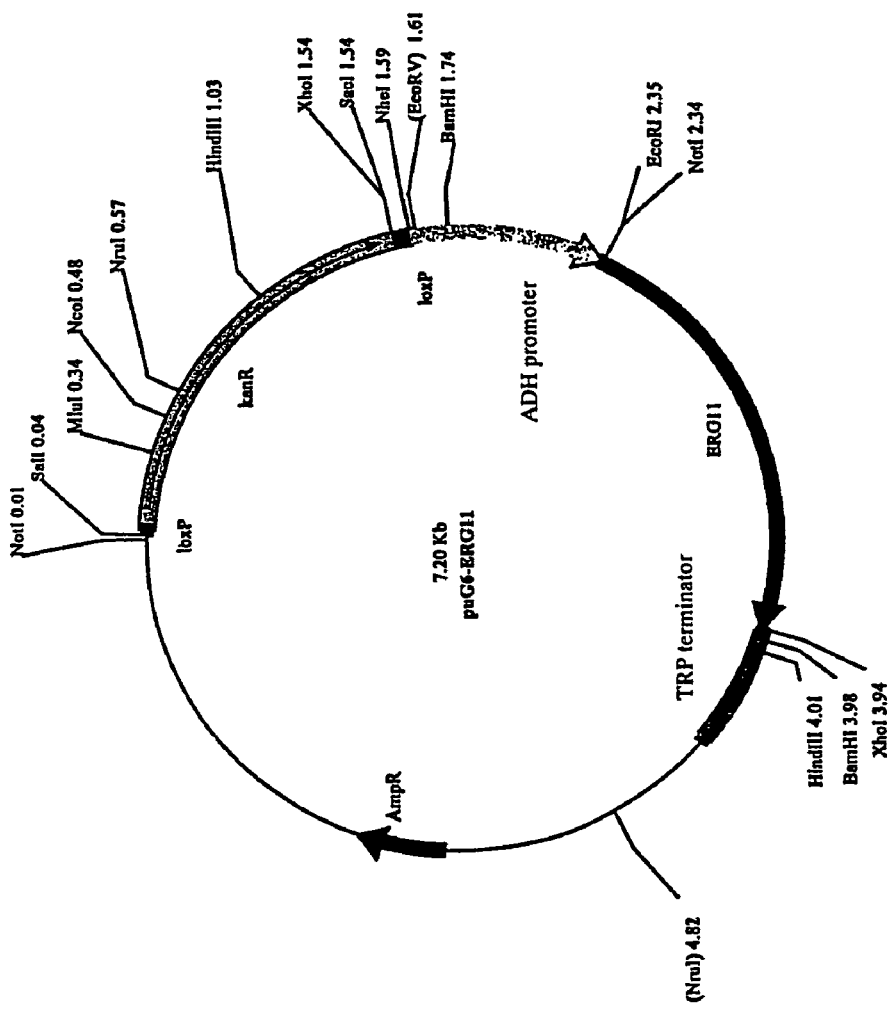

The DNA sequence for the expression cassette composed of ADH1-promotor-ERG11-tryptophan-terminator was isolated from the vector pFlat3-ERG11 by restriction with the enzymes EcoRV and Bsp68I (NruI) using standard methods. The DNA fragment obtained was cloned with blunt ends into the EcoRV cleavage site of the vector pUG6 (Güldener, U et al. (1996): A new efficient gene disruption cassette for repeated use in budding yeast, Nucleic Acids Res. July 1; 24(13):2519-24), resulting in the vector denoted pUG6-ERG11 (FIG. 3).

1.4. Integrative Transformation of the Expression Cassettes into the Yeast Strains GRF or GRFura3

After plasmid isolation, fragments of the vectors pUG6-tHMG, pUG6-ERG1 and pUG6-ERG11 were amplified by means of PCR in such a way that the resulting fragments consist of the following components: loxP-kanMX-loxP-ADH1 promoter-target gene-tryptophan terminator, with target gene meaning tHMG, ERG1 and, ERG11 and kanMX respectively, meaning a kanamycin-resistance gene.

The selected primers were oligonucleotide sequences which contain in the annealing region the sequences beyond the cassettes to be amplified of the vector pUG6-target gene and which contain at the 5' and 3' protruding ends in each case 40 base pairs of the 5' or 3' sequence of the integration locus. This ensures that on the one hand the entire fragment, including KanMX and target gene, is amplified and, on the other hand, this fragment can then be transformed into yeast and be integrated by homologous recombination into the target gene locus of the yeast. Depending on the target gene locus in the yeast, the following oligonucleotide sequences were used as primers:

For integration at the URA3 gene locus:

```
URA3-Crelox-5' (SEQ. ID. No. 33):
5'-ATGTCGAAAG CTACATATAA GGAACGTGCT GCATCTCATC
CCAGCTGAAG CTTCGTACGC-3'

URA3-Crelox-3' (SEQ. ID. No. 34):
5'-TTAGTTTTGC TGGCCGCATC TTCTCAAATA TGCTTCCCAG
GCATAGGCCA CTAGTGGATC TG-3'
```

For integration at the LEU2 gene locus:

```
LEU2-Crelox-5' (SEQ. ID. No. 35):
5'-GAATACTCAG GTATCGTAAG ATGCAAGAGT TCGAATCTCT
CCAGCTGAAG CTTCGTACGC-3'

LEU2-Crelox-3' (SEQ. ID. No. 36):
5'-TCTACCCTAT GAACATATTC CATTTTGTAA TTTCGTGTCG
GCATAGGCCA CTAGTGGATC TG-3'
```

For integration at the HIS3 gene locus:

```
HIS3-Crelox-5' (SEQ. ID. No. 37):
5'-ATGACAGAGC AGAAAGCCCT AGTAAAGCGT ATTACAAATG
CCAGCTGAAG CTTCGTACGC-3'

HIS3-Crelox-3' (SEQ. ID. No. 38):
5'-CTACATAAGA ACACCTTTGG TGGAGGGAAC ATCGTTGGTA
GCATAGGCCA CTAGTGGATC TG-3'
```

For integration at the ERG6 gene locus:

```
ERG6-Crelox-5' (SEQ. ID. No. 39):
5'-ATGAGTGAAA CAGAATTGAG AAAAAGACAG GCCCAATTCA
CCAGCTGAAG CTTCGTACGC-3'
```

-continued

ERG6-Crelox-3' (SEQ. ID. No. 40):
5'-TTATTGAGTT GCTTCTTGGG AAGTTTGGGA GGGGGTTTCG
GCATAGGCCA CTAGTGGATC TG-3'

For integration at the ERG5 gene locus:

ERG5-Crelox-5' (SEQ. ID. No. 41):
5'-ATGAGTTCTG TCGCAGAAAA TATAATACAA CATGCCACTC
CCAGCTGAAG CTTCGTACGC-3'

ERG5-Crelox-3' (SEQ. ID. No. 42):
5'-TTATTCGAAG ACTTCTCCAG TAATTGGGTC TCTCTTTTTG
GCATAGGCCA CTAGTGGATC TG-3'

The resistance to Geneticin (G418) served as selection marker. The resulting strains contained a copy of the particular target gene (tHMG, ERG1 or ERG11) under the control of the ADH promoter and the tryptophan terminator. At the same time, it was possible to delete the particular gene of the target locus by integrating the expression cassette. In order to subsequently remove again the gene for G418 resistance, the resultant yeast strain was transformed with the cre recombinase-containing vector pSH47 (Guldener U, Heck S, Fielder T, Beinhauer J, Hegemann J H. (1996) A new efficient gene disruption cassette for repeated use in budding yeast. Nucleic Acids Res. July 1; 24(13):2519-24). This vector caused the expression of cre recombinase in the yeast, and, as a consequence, the sequence region within the two loxP sequences was removed by recombination, and this in turn resulted in only one of the two loxP sequences and the ADH1 promoter-target gene-tryptophan terminator expression cassette remaining in the target gene locus.

As a consequence, the yeast strain loses its G418 resistance again and is therefore suitable for integrating or removing further genes by means of this "cre-lox" system into or from said yeast strain. The vector pSH47 can then be removed selectively by cultivation on FOA medium.

Thus it is possible to integrate a plurality of target genes successively into the yeast strain under the control of the ADH1 promoter and tryptophan terminator at various target loci.

Figure 4:
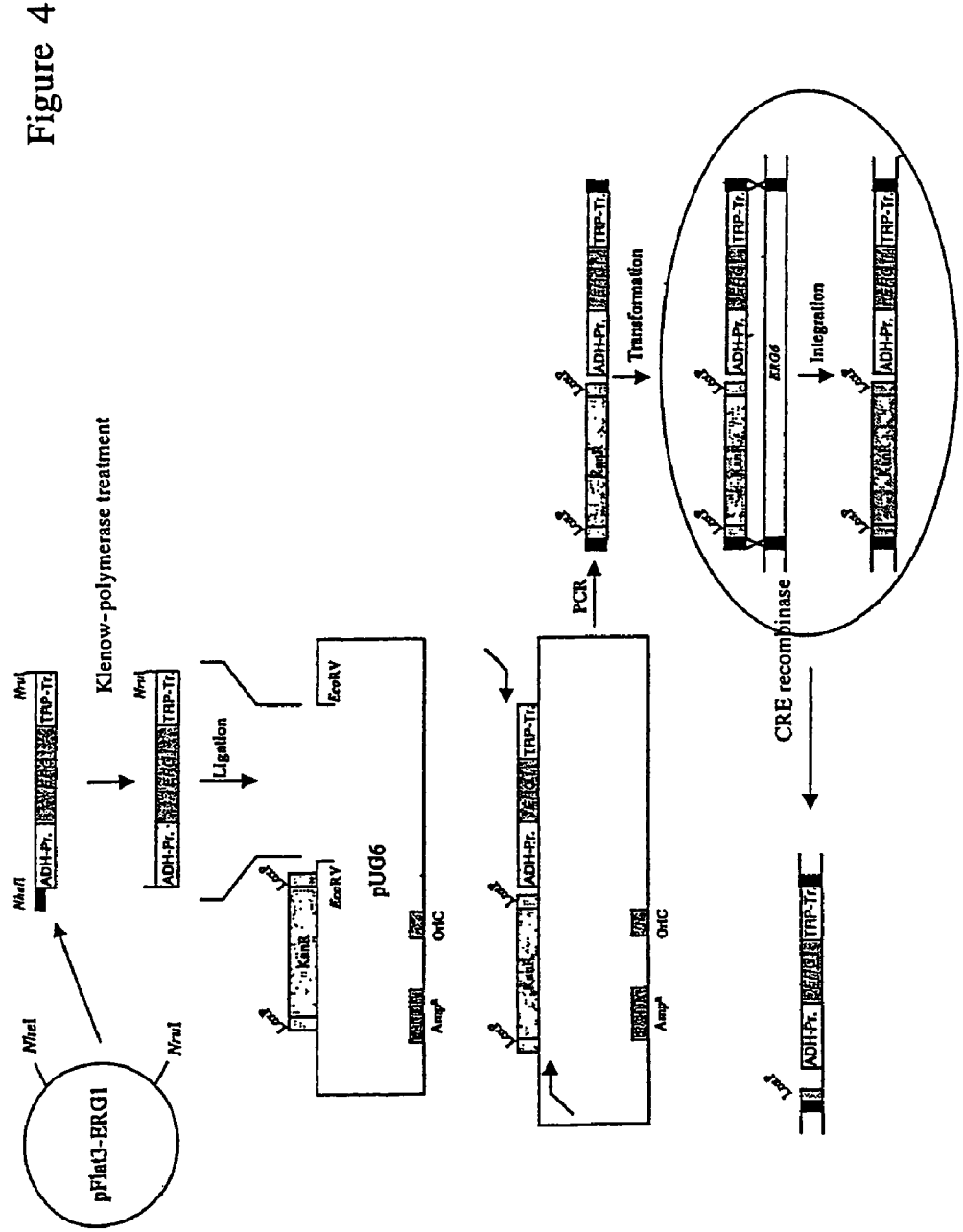

First, a target gene is integrated at the URA3 locus or a ura3 strain is used in order to render the yeast strain uracil-auxotrophic, since the vector pSH47 contains a URA3 gene for selection of uracil-prototrophic strains. FIG. 4 shows an example of the method.

This method produced the yeast integration and deletion strains listed in Table 1, with, in a manner known per se, the gene in lower-case letters representing a deletion and the gene in capital letters representing an integration.

TABLE 1

| No. | Strain name | Modification compared to GRF yeast strain |
|---|---|---|
| I | GRFtH1 | ura3, tHMG:leu2 |
| II | GRFtH1E1 | ERG1:ura3, tHMG:leu2 |
| III | GRFtH1E11 | ura3, tHMG:leu2, ERG11:his3 |
| IV | GRFtH1E1E11 | ERG1:ura3, tHMG:leu2, ERG11:his3 |
| V | GRFtH1E1E11erg5erg6 | ura3, tHMG:leu2, ERG1:erg6, ERG11:erg5 |
| VI | GRFtH1erg5erg6 | ura3, tHMG:leu2, erg5, erg6 |

The yeast strains were cultured in a culture volume of 20 ml in WMVIII medium at 28° C. and 160 rpm for 48 hours. Subsequently, 500 µl of this preculture were transferred to a 50 ml main culture of the same medium and cultured in a baffled flask at 28° C. and 160 rpm for 3 days.

After 3 days, the sterols and squalene were extracted (Parks L W, Bottema C D, Rodriguez R J, Lewis T A. (1985) Yeast sterols: yeast mutants as tools for the study of sterol metabolism. Methods Enzymol. 1985; 111:333-46.) and analyzed by means of gas chromatography. The following values were obtained (see Table 2).

TABLE 2

| No. | Strain name | Content of sterols 1 to 11 in [peak area/gTS] | | | | | | | | | | |
|---|---|---|---|---|---|---|---|---|---|---|---|---|
| | | 1 | 2 | 3 | 4 | 5 | 6 | 7 | 8 | 9 | 10 | 11 |
| I | GRFtH1 | 9.9 | 0.8 | 0.3 | 1.2 | 1.1 | 1.0 | 0.0 | 0.0 | 0.0 | 0.0 | 4.7 |
| II | GRFtH1E1 | 6.8 | 1.9 | 0.4 | 1.5 | 2.2 | 2.1 | 0.0 | 0.0 | 0.0 | 0.0 | 6.9 |
| III | GRFtH1E11 | 9.9 | 0.4 | 0.7 | 2.3 | 1.9 | 1.9 | 0.0 | 0.0 | 0.0 | 0.0 | 5.0 |
| IV | GRFtH1E1E11 | 6.0 | 1.2 | 0.9 | 3.0 | 2.3 | 2.2 | 0.0 | 0.0 | 0.0 | 0.0 | 7.2 |
| V | GRFtH1E1E11erg5erg6 | 5.8 | 0.8 | 0.4 | 23.1 | 0.0 | 0.0 | 0.0 | 0.0 | 11.8 | 0.0 | 0.0 |
| VI | GRFtH1erg5erg6 | 9.9 | 0.8 | 0.3 | 12.6 | 0.0 | 0.0 | 0.0 | 0.0 | 7.1 | 0.0 | 0.0 |

1 = Squalene
2 = Lanosterol
3 = Dimethylzymosterol
4 = Zymosterol
5 = Fecosterol
6 = Episterol
7 = Cholesta-7,24-dienol
8 = Cholesta-8-enol
9 = Cholesta-5,7,24 trienol
10 = 7-Dehydrocholesterol
11 = Ergosterol Example 2

Expression of the Heterologous Gene Encoding a Δ8-Δ7-isomerase (Ebp) from Mice (*Mus musculus*) in Yeast The cDNA sequence of *Mus musculus* Δ8-Δ7-isomerase (Moebius, F. F., Soellner, K. E. M., Fiechter, B., Huck, C. W., Bonn, G., Glossmann, H. (1999): Histidine77, Glutamic Acid123, Threonine126, Asparagine194, and Tryptophan197 of Human Emopamil Protein Are Required for in Vivo Sterol Δ8-Δ7 Isomerisation. Biochem. 38, 1119-1127) was amplified by PCR from the cDNA clone IMAGp998A22757 (Host:

E. coli DH10B) of the Deutsches Resourcenzentrum für Genomforschung [German resource center for genome research] GmbH (Berlin).

Figure 5A:
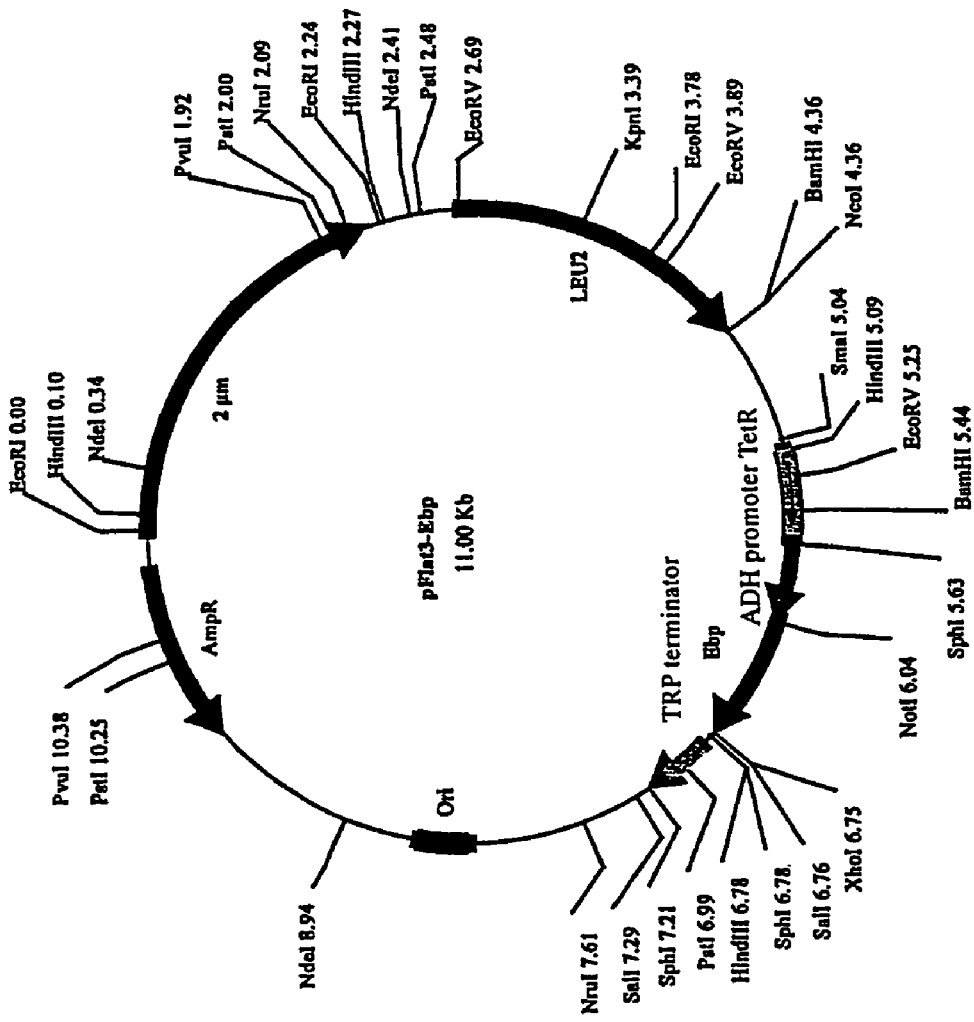

The primers used here are the DNA oligomers Ebp-5' (SEQ. ID. No. 43) and Ebp-3' (SEQ. ID. No. 44). The DNA fragment obtained was treated with restriction enzymes NotI and XhoI and then integrated into the vectors pFlat3 and pFlat1 (FIG. 4) which likewise been treated with the enzymes NotI and XhoI beforehand by means of a ligase reaction. The resulting vectors pFlat1-EBP and pFlat3-EBP (FIG. 5a) contain the EBP gene under the control of the ADH promoter and the tryptophan terminator.

The expression vector pFlat3-EBP was then transformed into the yeast strains I to VI of Table 1 from Example 1 and also into the GRFura3 strain. The yeast strains obtained in this way were then cultured in a culture volume of 20 ml in WMVIII medium at 28° C. and 160 rpm for 48 hours. Subsequently, 500 µl of this preculture were transferred to a 50 ml main culture of the same medium and cultured in a baffled flask at 28° C. and 160 rpm for 3 days.

The sterols were extracted after 3 days and analyzed by means of gas chromatography, as described in Example 1. The influence of the expression of a *Mus musculus* Δ8-Δ7-isomerase in combination with the experssion of the transcriptionally deregulated intrinsic yeast genes tHMG and/or ERG1 and/or ERG11 and/or deletion of the intrinsic yeast genes ERG6 and ERG5 is listed in Table 3. The abbreviations have the following meanings:

−=decrease; 0=no change; /=not present;

+, ++, +++, ++++=concentrated to highly concentrated.

Example 3

Figure 5B:
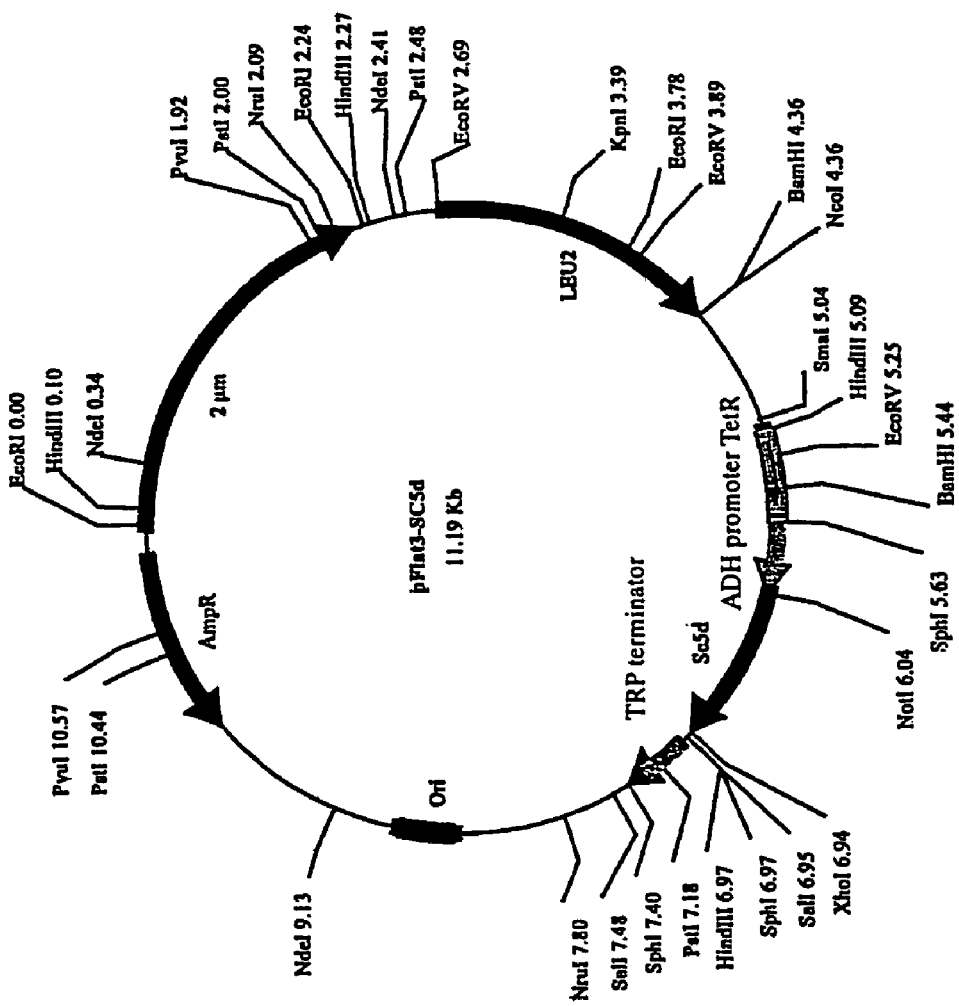
Figure 5C:
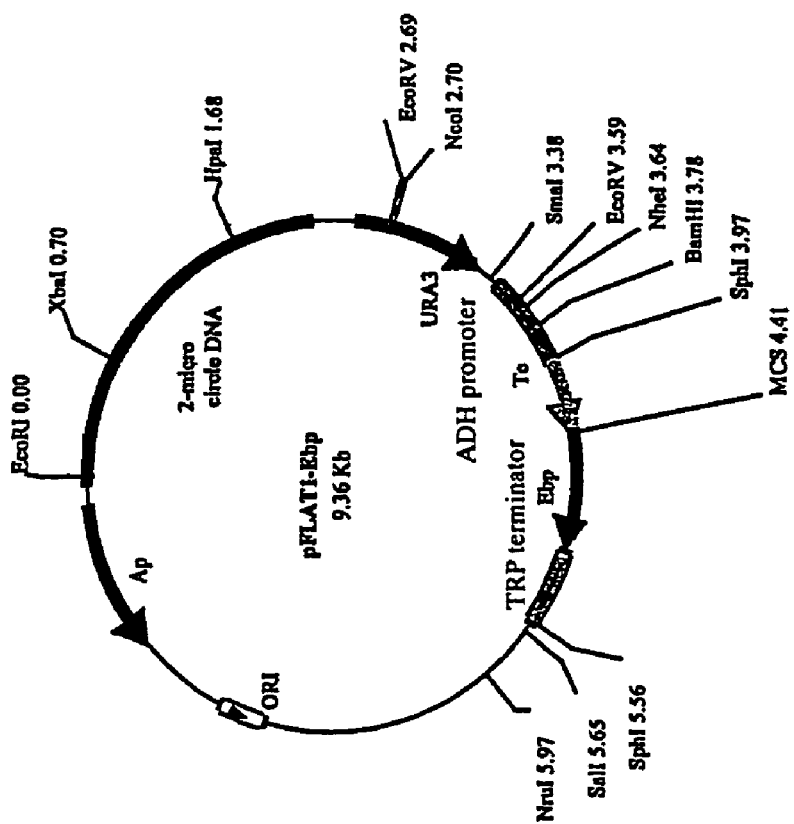

Expression of the Heterologous Gene Encoding a Δ5-desaturase (Sc5d) from Mice (*Mus musculus*) in Yeast The cDNA sequence of *Mus musculus* Δ5-desaturase (Nishi, S., Hideaki, N., Ishibashi, T. (2000): cDNA cloning of the mammalian sterol C5-desaturase and the expression in yeast mutant. Biochim. Biophys. A 1490, 106-108) was amplified by PCR from the cDNA clone IMAGp998K144618 (Host: *E. coli* DH10B) of the Deutsches Resourcenzentrum für Genomforschung [German resource center for genome research] GmbH (Berlin). The primers used here are the DNA oligomers Sc5d-5' (SEQ. ID. No. 45) and Sc5d-3' (SEQ. ID. No. 46). The DNA fragment obtained was treated with restriction enzymes NotI and XhoI and then integrated into the vector pFlat3 (FIG. 4) which likewise had been treated with the enzymes NotI and XhoI beforehand, by means of a ligase reaction. The resulting vector pFlat3-SC5D (FIG. 5b) contains the SC5D gene under the control of the ADH promoter and the tryptophan terminator.

The expression vector pFlat3-SC5D was then transformed into the yeast strains I to VI of Table 1 from Example 1 and also into the GRFura3 strain. The yeast strains obtained in this way were then cultured in a culture volume of 20 ml in WMVIII medium at 28° C. and 160 rpm for 48 hours. Subsequently, 500 µl of this preculture were transferred to a 50 ml main culture of the same medium and cultured in a baffled flask at 28° C. and 160 rpm for 3 days.

TABLE 3

| No. | Strain name | Influence of the genetic modifications on the sterol content compared to the GRF yeast strain | | | | | | | | | | |
|-----|-------------|---|---|---|---|---|---|---|---|---|---|---|
| | | 1 | 2 | 3 | 4 | 5 | 6 | 7 | 8 | 9 | 10 | 11 |
| VII | GRFtH1 pFlat3-Ebp | 0 | 0 | 0 | 0 | 0 | 0 | / | / | / | / | 0 |
| VIII | GRFtH1E1 pFlat3-Ebp | 0 | 0 | 0 | − | 0 | 0 | + | / | / | / | 0 |
| IX | GRFtH1E11 pFlat3-Ebp | 0 | 0 | 0 | − | 0 | 0 | + | / | / | / | 0 |
| X | GRFtH1E1E11 pFlat3-Ebp | 0 | 0 | 0 | − | 0 | 0 | + | / | / | / | 0 |
| XI | GRFtH1E1E11erg5erg6 pFlat3-Ebp | 0 | 0 | 0 | −− | / | / | + | / | ++ | / | / |
| XII | GRFtH1erg5erg6 pFlat3-Ebp | 0 | 0 | 0 | − | / | / | + | / | + | / | / |

1 = Squalene
2 = Lanosterol
3 = Dimethylzymosterol
4 = Zymosterol
5 = Fecosterol
6 = Episterol
7 = Cholesta-7,24-dienol
8 = Cholesta-8-enol
9 = Cholesta-5,7,24 trienol
10 = 7-Dehydrocholesterol
11 = Ergosterol The sterols were extracted after 3 days and analyzed by means of gas chromatography, as described in Example 1. The influence of the expression of a *Mus musculus* Δ5-desaturase in combination with the experssion of the transcriptionally deregulated intrinsic yeast genes tHMG and/or ERG1 and/or ERG11 and/or deletion of the intrinsic yeast genes ERG6 and ERG5 is listed in Table 4. The abbreviations have the following meanings:

−=decrease; 0=no change; /=not present;

+, ++, +++, ++++=concentrated to highly concentrated.

TABLE 4

| | | Influence of the genetic modifications on the sterol content compared to the GRF yeast strain | | | | | | | | | | |
|---|---|---|---|---|---|---|---|---|---|---|---|---|
| No. | Strain name | 1 | 2 | 3 | 4 | 5 | 6 | 7 | 8 | 9 | 10 | 11 |
| XIII | GRFtH1 pFlat3-Sc5d | 0 | 0 | 0 | 0 | 0 | 0 | / | / | / | / | 0 |
| XIV | GRFtH1E1 pFlat3-Sc5d | 0 | 0 | 0 | − | 0 | 0 | / | / | + | / | 0 |
| XV | GRFtH1E11 pFlat3-Sc5d | 0 | 0 | 0 | − | 0 | 0 | / | / | + | / | 0 |
| XVI | GRFtH1E1E11 pFlat3-Sc5d | 0 | 0 | 0 | − | 0 | 0 | / | / | + | / | 0 |
| XVII | GRFtH1E1E11erg5erg6 pFlat3-Sc5d | 0 | − | 0 | −−− | / | / | / | / | +++ | + | / |
| XVIII | GRFtH1erg5erg6 pFlat3-Sc5d | 0 | 0 | 0 | −− | / | / | / | / | ++ | / | / |

1 = Squalene
2 = Lanosterol
3 = Dimethylzymosterol
4 = Zymosterol
5 = Fecosterol
6 = Episterol
7 = Cholesta-7,24-dienol
8 = Cholesta-8-enol
9 = Cholesta-5,7,24 trienol
10 = 7-Dehydrocholesterol
11 = Ergosterol Example 4

Expression of the Heterologous Gene Encoding a Δ24-reductase (D24R) from Mice (*Mus musculus*) in Yeast The cDNA sequence of *Mus musculus* Δ24-reductase (Waterham, H. R., Koster, J., Romeijn, G. J., Hennekam, R. C., Vreken, P., Andersson, H. C., FitzPatrick, D. R., Kelley, R. I. and Wanders, R. J., Mutations in the 3beta-Hydroxysterol Delta24-Reductase Gene Cause Desmosterolosis, an Autosomal Recessive Disorder of Cholesterol Biosynthesis, Am. J. Hum. Genet. 69 (4), 685-694 (2001)) was amplified by PCR from the cDNA clone IMAGp998K179532 (Host: *E. coli* DH10B) of the Deutsches Resourcenzentrum für Genomforschung [German resource center for genome research] GmbH (Berlin).

Figure 5D:
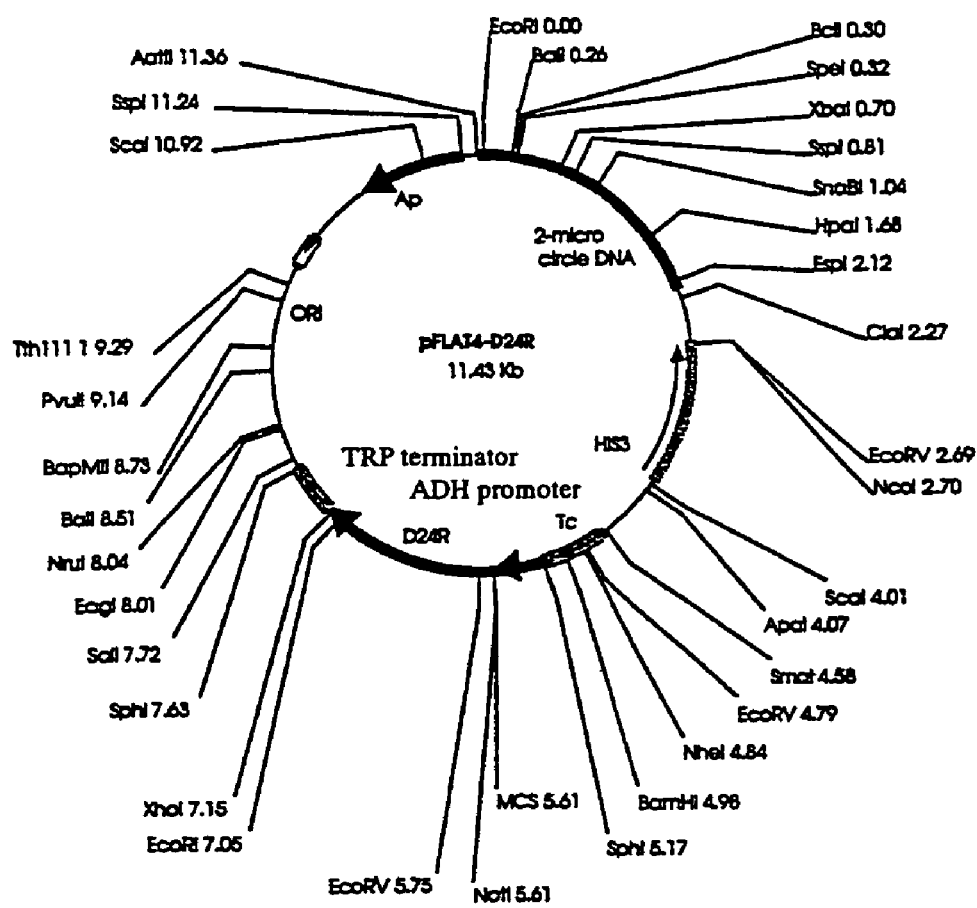
Figure 6:
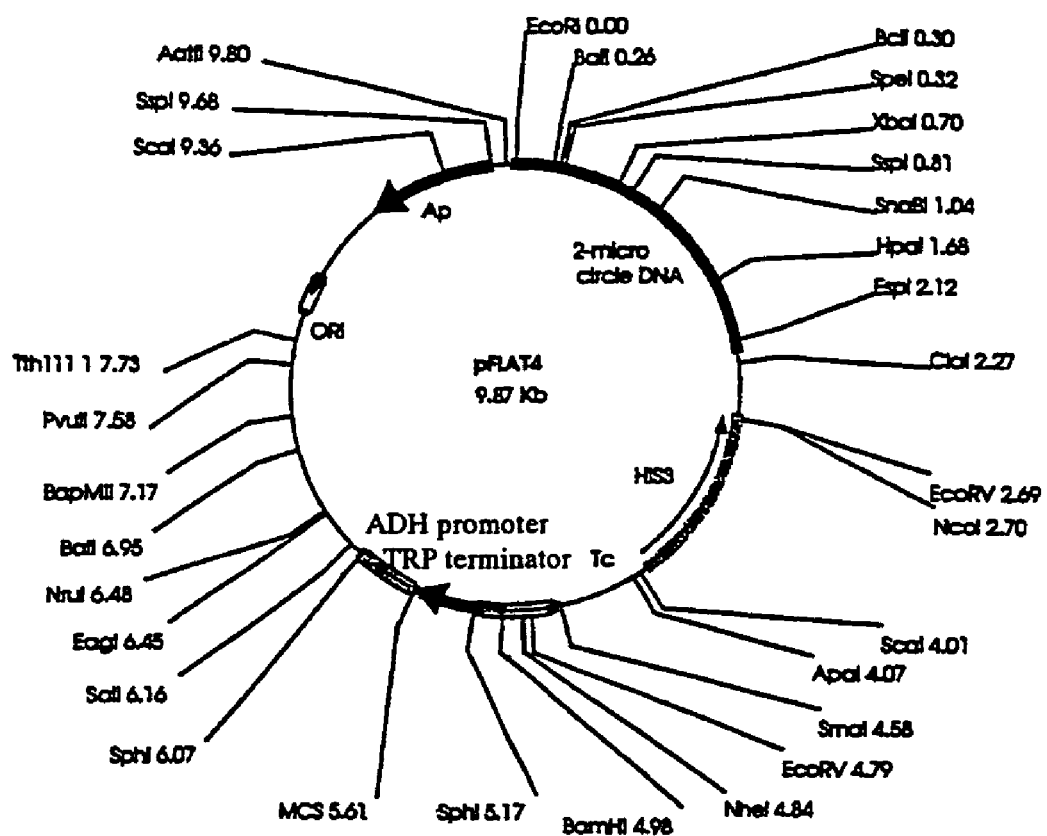

The primers used here are the DNA oligomers D24R-5' (SEQ. ID. No. 47) and D24R-3' (SEQ. ID. No. 48). The DNA fragment obtained was treated with restriction enzymes NotI and XhoI and then integrated into the vector pFlat4 (FIG. 6) which likewise had been treated with the enzymes NotI and XhoI beforehand, by means of a ligase reaction. The resulting vector pFlat4-D24R (FIG. 5d) contains the D24R gene under the control of the ADH1 promoter and the tryptophan terminator.

The expression vector pFlat4-D24R was then transformed into the yeast strains I to VI of Table 1 from Example 1 and also into the GRFura3 strain. The yeast strains obtained in this way were then cultured in a culture volume of 20 ml in WMVIII medium at 28° C. and 160 rpm for 48 hours. Subsequently, 500 μl of this preculture were transferred to a 50 ml main culture of the same medium and cultured in a baffled flask at 28° C. and 160 rpm for 3 days.

The sterols were extracted after 3 days and analyzed by means of gas chromatography, as described in Example 1. The influence of the expression of a *Mus musculus* Δ24-reductase in combination with the expression of the transcriptionally deregulated intrinsic yeast genes tHMG and/or ERG1 and/or ERG11 and/or deletion of the intrinsic yeast genes ERG6 and ERG5 is listed in Table 5. The abbreviations have the following meanings:

−=decrease; 0=no change; /=not present;

+, ++, +++, ++++=concentrated to highly concentrated.

TABLE 5

Influence of the genetic modifications on the sterol content compared to the GRF yeast strain

| No. | Strain name | 1 | 2 | 3 | 4 | 5 | 6 | 7 | 8 | 9 | 10 | 11 |
|---|---|---|---|---|---|---|---|---|---|---|---|---|
| XIX | GRFtH1 pFlat4-D24R | 0 | 0 | 0 | 0 | 0 | 0 | / | / | / | / | 0 |
| XX | GRFtH1E1 pFlat4-D24R | 0 | − | − | − | 0 | 0 | / | / | / | + | 0 |
| XXI | GRFtH1E11 pFlat4-D24R | 0 | 0 | 0 | − | 0 | 0 | / | + | / | + | 0 |
| XXII | GRFtH1E1E11 pFlat4-D24R | 0 | 0 | 0 | − | 0 | 0 | / | + | / | + | 0 |
| XXIII | GRFtH1E1E11erg5erg6 pFlat4-D24R | 0 | − | − | −−− | / | / | 0 | + | + | +++ | / |
| XXIV | GRFtH1erg5erg6 pFlat4-D24R | 0 | − | − | −− | / | / | 0 | + | + | ++ | / |

1 = Squalene
2 = Lanosterol
3 = Dimethylzymosterol
4 = Zymosterol
5 = Fecosterol
6 = Episterol
7 = Cholesta-7,24-dienol
8 = Cholesta-8-enol
9 = Cholesta-5,7,24 trienol
10 = 7-Dehydrocholesterol
11 = Ergosterol

Example 5

Coexpression of the Heterologous Genes Encoding a Δ8-Δ7-isomerase (Ebp) from Mice (*Mus musculus*) and a C5-desaturase (Sc5d) from Mice (*Mus musculus*) in Yeast The expression vectors pFlat1-EBP (from Example 2) and pFlat3-SC5D (from Example 3) were transformed into the yeast strains I to VI of Table 1 of Example 1 and also into the GRFura3 strain. The yeast strains obtained in this way were then cultured in a culture volume of 20 ml in WMVIII medium at 28° C. and 160 rpm for 48 hours. Subsequently, 500 μl of this preculture were transferred to a 50 ml main culture of the same medium and cultured in a baffled flask at 28° C. and 160 rpm for 3 days.

The sterols were extracted after 3 days and analyzed by means of gas chromatography, as described in Example 1. The influence of the expression of a Δ8-Δ7-isomerase and a *Mus musculus* C5-desaturase in combination with the expression of the transcriptionally deregulated intrinsic yeast genes tHMG and/or ERG1 and/or ERG11 and/or deletion of the intrinsic yeast genes ERG6 and ERG5 is listed in Table 6. The abbreviations have the following meanings:

−=decrease; 0=no change; /=not present;

+, ++, +++, ++++=concentrated to highly concentrated.

TABLE 6

Influence of the genetic modifications on the sterol content compared to the GRF yeast strain

| No. | Strain name | 1 | 2 | 3 | 4 | 5 | 6 | 7 | 8 | 9 | 10 | 11 |
|---|---|---|---|---|---|---|---|---|---|---|---|---|
| XXV | GRFtH1 pFlat3-Ebp/ pFlat1-Sc5d | 0 | 0 | 0 | − | 0 | 0 | / | / | + | / | 0 |
| XXVI | GRFtH1E1 pFlat3-Ebp/ pFlat1-Sc5d | 0 | − | 0 | −− | 0 | 0 | / | / | + | / | 0 |
| XXVII | GRFtH1E11 pFlat3-Ebp/ pFlat1-Sc5d | 0 | 0 | 0 | −− | 0 | 0 | / | / | + | / | 0 |
| XXVIII | GRFtH1E1E11 pFlat3-Ebp/ pFlat1-Sc5d | 0 | − | − | −− | 0 | 0 | / | / | ++ | / | 0 |
| XXIX | GRFtH1E1E11erg5erg6 pFlat3-Ebp/ pFlat1-Sc5d | 0 | − | 0 | −− | / | / | / | / | +++ | + | / |

TABLE 6-continued

Influence of the genetic modifications on the sterol content compared to the GRF yeast strain

| No. | Strain name | 1 | 2 | 3 | 4 | 5 | 6 | 7 | 8 | 9 | 10 | 11 |
|---|---|---|---|---|---|---|---|---|---|---|---|---|
| XXX | GRFtH1erg5erg6 pFlat3-Ebp/ pFlat1-Sc5d | 0 | 0 | 0 | – | / | / | / | / | ++ | + | / |

1 = Squalene
2 = Lanosterol
3 = Dimethylzymosterol
4 = Zymosterol
5 = Fecosterol
6 = Episterol
7 = Cholesta-7,24-dienol
8 = Cholesta-8-enol
9 = Cholesta-5,7,24 trienol
10 = 7-Dehydrocholesterol
11 = Ergosterol Example 6

Coexpression of the Heterologous Genes Encoding a Δ8-Δ7-isomerase (Ebp) from Mice (*Mus musculus*) Encoding a C5-desaturase (Sc5d) from Mice (*Mus musculus*) and a Δ24-reductase from Mice (*Mus musculus*) in Yeast The expression vectors pFlat1-EBP (from Example 2) and pFlat3-SC5D (from Example 3) and pFlat4-D24R (from Example 4) were transformed into the yeast strains I to VI of Table 1 of Example 1 and also into the GRFura3 strain. The yeast strains obtained in this way were then cultured in a culture volume of 20 ml in WMVIII medium at 28° C. and 160 rpm for 48 hours. Subsequently, 500 μl of this preculture were transferred to a 50 ml main culture of the same medium and cultured in a baffled flask at 28° C. and 160 rpm for 3 days.

The sterols were extracted after 3 days and analyzed by means of gas chromatography, as described in Example 1. The influence of the expression of a Δ8-Δ7-isomerase, a *Mus musculus* C5-desaturase and a *Mus musculus* Δ24-reductase in combination with the expression of the transcriptionally deregulated intrinsic yeast genes tHMG and/or ERG1 and/or ERG11 and/or deletion of the intrinsic yeast genes ERG6 and ERG5 is listed in Table 7. The abbreviations have the following meanings:

–=decrease; 0=no change; /=not present;

++, +++, ++++=concentrated to highly concentrated.

TABLE 7

Influence of the genetic modifications on the sterol content compared to the GRF yeast strain

| No | Strain name | 1 | 2 | 3 | 4 | 5 | 6 | 7 | 8 | 9 | 10 | 11 |
|---|---|---|---|---|---|---|---|---|---|---|---|---|
| XXXI | GRFtH1 pFlat3-Ebp/ pFlat1-Sc5d/ pFlat4-D24R | 0 | 0 | 0 | – | 0 | 0 | / | / | / | + | 0 |
| XXXII | GRFtH1E1 pFlat3-Ebp/ pFlat1-Sc5d/ pFlat4-D24R | 0 | – | 0 | – – | 0 | 0 | / | / | / | + | 0 |
| XXXIII | GRFtH1E11 pFlat3-Ebp/ pFlat1-Sc5d/ pFlat4-D24R | 0 | 0 | 0 | – – | 0 | 0 | / | / | / | + | 0 |
| XXXIV | GRFtH1E1E11 pFlat3-Ebp/ pFlat1-Sc5d/ pFlat4-D24R | 0 | – | – | – – | 0 | 0 | / | / | / | ++ | 0 |
| XXXV | GRFtH1E1E11erg5erg6 pFlat3-Ebp/ pFlat1-Sc5d/ pFlat4-D24R | 0 | – | 0 | – – – | / | / | / | / | + | ++++ | / |

TABLE 7-continued

| | | Influence of the genetic modifications on the sterol content compared to the GRF yeast strain | | | | | | | | | | |
|---|---|---|---|---|---|---|---|---|---|---|---|---|
| No | Strain name | 1 | 2 | 3 | 4 | 5 | 6 | 7 | 8 | 9 | 10 | 11 |
| XXXVI | GRFtH1erg5erg6 pFlat3-Ebp/ pFlat1-Sc5d/ pFlat4-D24R | 0 | 0 | 0 | − | / | / | / | / | ++ | +++ | / |

1 = Squalene
2 = Lanosterol
3 = Dimethyl zymosterol
4 = Zymosterol
5 = Fecosterol
6 = Episterol
7 = Cholesta-7,24-dienol
8 = Cholesta-8-enol
9 = Cholesta-5,7,24 trienol
10 = 7-Dehydrocholesterol
11 = Ergosterol

We claim:

1. A method for preparing 7-dehydrocholesterol and/or cholesterol by culturing yeast organisms which, compared to the wild type, have an increased activity of at least one of the activities selected from the group consisting of Δ8-Δ7-isomerase activity consisting of the enzymatic activity of Δ8-Δ7-isomerase having the amino acid sequence of SEQ ID.NO:2, 4 or 6, Δ5-desaturase activity consisting of the enzymatic activity of Δ5-desaturase having the amino acid sequence of SEQ ID.NO:8, 10 or 12 and Δ24-reductase activity consisting of the enzymatic activity of Δ24-reductase having the amino acid sequence of SEQ ID.NO: 14, 16 or 18 wherein the organisms additionally have increased activity of HMG-CoA-reductase obtained by gene expression of the nucleic acid sequence of SEQ.ID.NO: 23, harvesting the organisms after culturing and then isolating 7-dehydrocholesterol and/or cholesterol from said organisms.

2. A method for preparing 7-dehydrocholesterol and/or cholesterol by culturing yeast organisms which, compared to the wild type, have an increased activity of at least one of the activities selected from the group consisting of Δ8-Δ7-isomerase activity consisting of the enzymatic activity of Δ8-Δ7-isomerase having the amino acid sequence of SEQ ID NO: 2, 4 or 6, Δ5-desaturase activity consisting of the enzymatic activity of Δ5-desaturase having the amino acid sequence of SEQ ID.NO: 8, 10 or 12 and Δ24-reductase activity consisting of the enzymatic activity of Δ24-reductase having the amino acid sequence of SEQ ID.NO: 14, 16 or 18 wherein the organisms additionally increased activity of HMG-CoA-reductase consisting of the enzymatic activity of HMG-CoA-reductase having the amino acid sequence SEQ. ID. NO. 24, harvesting the organisms after culturing and then isolating 7-dehydrocheolesterol and/or cholesterol from said organisms.

3. The method of claim 1, wherein the cultured yeast organism has an increased Δ8-Δ7-isomerase activity consisting of the enzymatic activity of Δ8-Δ7-isomerase having SEQ ID.NO:2.

4. The method of claim 3, wherein the cultured yeast organism has an increased Δ8-Δ7-isomerase activity consisting of the enzymatic activity of Δ8-Δ7-isomerase having SEQ ID.NO:2 and an increased Δ5-desaturase activity consisting of the enzymatic activity of Δ5-desaturase having SEQ ID.NO:8.

5. The method of claim 1, wherein the cultured yeast organism has an increased Δ8-Δ7-isomerase activity consisting of the enzymatic activity of Δ8-Δ7-isomerase having SEQ ID.NO:2 and an increased Δ24-reductase activity consisting of the enzymatic activity of Δ24-reductase having SEQ ID.NO:14.

6. The method of claim 1, wherein the cultured yeast organism has an increased Δ5-desaturase activity consisting of the enzymatic activity of Δ5-desaturase having SEQ ID.NO:8.

7. The method of claim 6, wherein the cultured yeast organism has an increased Δ5-desaturase activity consisting of the enzymatic activity of Δ5-desaturase having SEQ ID.NO:8 and an increased Δ24-reductase activity consisting of the enzymatic activity of Δ24-reductase having SEQ ID.NO:14.

8. The method of claim 1, wherein the cultured yeast organism has an increased Δ24-reductase activity consisting of the enzymatic activity of Δ24-reductase having SEQ ID.NO:14.

9. The method of claim 2, wherein the cultured yeast organism has an increased Δ8-Δ7-isomerase activity consisting of the enzymatic activity of Δ8-Δ7-isomerase having SEQ ID.NO:2.

10. The method of claim 9, wherein the cultured yeast organism has an increased Δ8-Δ7-isomerase activity consisting of the enzymatic activity of Δ8-Δ7-isomerase having SEQ ID.NO:2 and an increased Δ5-desaturase activity consisting of the enzymatic activity of Δ5-desaturase having SEQ ID.NO:8.

11. The method of claim 1, wherein the cultured yeast organism has an increased Δ8-Δ7-isomerase activity consisting of the enzymatic activity of Δ8-Δ7-isomerase having SEQ ID.NO:2 and an increased Δ24-reductase activity consisting of the enzymatic activity of Δ24-reductase having SEQ ID.NO:14.

12. The method of claim 1, wherein the cultured yeast organism has an increased Δ5-desaturase activity consisting of the enzymatic activity of Δ5-desaturase having SEQ ID.NO:8.

13. The method of claim 12, wherein the cultured yeast organism has an increased Δ5-desaturase activity consisting of the enzymatic activity of Δ5-desaturase having SEQ ID.NO:8 and an increased Δ24-reductase activity consisting of the enzymatic activity of Δ24-reductase having SEQ ID.NO:14.

14. The method of claim 1, wherein the cultured yeast organism has an increased Δ24-reductase activity consisting of the enzymatic activity of Δ24-reductase having SEQ ID.NO:14.

* * * * *

SEQUENCE LISTING

<160> NUMBER OF SEQ ID NOS: 60

<210> SEQ ID NO 1
<211> LENGTH: 693
<212> TYPE: DNA
<213> ORGANISM: Mus musculus
<220> FEATURE:
<221> NAME/KEY: CDS
<222> LOCATION: (1)..(693)

<400> SEQUENCE: 1

```
atg acc acc aat acg gtc ccc ttg cac ccg tac tgg ccc agg cac ctg      48
Met Thr Thr Asn Thr Val Pro Leu His Pro Tyr Trp Pro Arg His Leu
 1               5                  10                  15 aag ctg gac aac ttc gtg cct aat gac ctc ccg act tcg cat atc ctg      96
Lys Leu Asp Asn Phe Val Pro Asn Asp Leu Pro Thr Ser His Ile Leu
             20                  25                  30 gtt ggc ctc ttc tcc atc tct ggg ggc cta att gtg atc acg tgg ctg     144
Val Gly Leu Phe Ser Ile Ser Gly Gly Leu Ile Val Ile Thr Trp Leu
         35                  40                  45 ttg tct agc cga gct tcc gtc gtc cca ctt gga gct ggg cgg cga ctg     192
Leu Ser Ser Arg Ala Ser Val Val Pro Leu Gly Ala Gly Arg Arg Leu
     50                  55                  60 gcc ttg tgc tgg ttt gct gtg tgt acc ttc att cac ctt gtg atc gag     240
Ala Leu Cys Trp Phe Ala Val Cys Thr Phe Ile His Leu Val Ile Glu
 65                  70                  75                  80 ggc tgg ttc tct ctc tac aat ggc atc ctt tta gaa gac caa gcc ttc     288
Gly Trp Phe Ser Leu Tyr Asn Gly Ile Leu Leu Glu Asp Gln Ala Phe
                 85                  90                  95 tta tcc caa ctc tgg aaa gag tat tcc aag gga gat agc cga tat atc     336
Leu Ser Gln Leu Trp Lys Glu Tyr Ser Lys Gly Asp Ser Arg Tyr Ile
            100                 105                 110 ctt agt gac agc ttc gtc gtc tgt atg gag act gtc aca gct tgt ctc     384
Leu Ser Asp Ser Phe Val Val Cys Met Glu Thr Val Thr Ala Cys Leu
        115                 120                 125 tgg gga cca ctc agc cta tgg gta gtg att gcc ttt ctc cgc caa cag     432
Trp Gly Pro Leu Ser Leu Trp Val Val Ile Ala Phe Leu Arg Gln Gln
    130                 135                 140 ccc ttc cgc ttt gtc cta cag ctt gtg gtg tct atg ggc cag ata tac     480
```

```
Pro Phe Arg Phe Val Leu Gln Leu Val Val Ser Met Gly Gln Ile Tyr
145                 150                 155                 160 ggg gat gtg ctg tac ttc ctg aca gag cta cac gaa gga ctc cag cat    528
Gly Asp Val Leu Tyr Phe Leu Thr Glu Leu His Glu Gly Leu Gln His
                165                 170                 175 ggg gag ata ggc cac ccc gtt tat ttc tgg ttc tat ttt gtt ttc ctg    576
Gly Glu Ile Gly His Pro Val Tyr Phe Trp Phe Tyr Phe Val Phe Leu
            180                 185                 190 aat gct gta tgg ttg gtg ata cca agc atc ctt gtg ctt gat gcc ata    624
Asn Ala Val Trp Leu Val Ile Pro Ser Ile Leu Val Leu Asp Ala Ile
        195                 200                 205 aag cat ctc act agt gcc cag agc gtg ctg gac agc aaa gtc atg aaa    672
Lys His Leu Thr Ser Ala Gln Ser Val Leu Asp Ser Lys Val Met Lys
    210                 215                 220 att aag agc aag cat aac taa                                         693
Ile Lys Ser Lys His Asn
225                 230

<210> SEQ ID NO 2
<211> LENGTH: 230
<212> TYPE: PRT
<213> ORGANISM: Mus musculus

<400> SEQUENCE: 2

Met Thr Thr Asn Thr Val Pro Leu His Pro Tyr Trp Pro Arg His Leu
1               5                   10                  15

Lys Leu Asp Asn Phe Val Pro Asn Asp Leu Pro Thr Ser His Ile Leu
            20                  25                  30

Val Gly Leu Phe Ser Ile Ser Gly Gly Leu Ile Val Ile Thr Trp Leu
        35                  40                  45

Leu Ser Ser Arg Ala Ser Val Val Pro Leu Gly Ala Gly Arg Arg Leu
    50                  55                  60

Ala Leu Cys Trp Phe Ala Val Cys Thr Phe Ile His Leu Val Ile Glu
65                  70                  75                  80

Gly Trp Phe Ser Leu Tyr Asn Gly Ile Leu Leu Glu Asp Gln Ala Phe
                85                  90                  95

Leu Ser Gln Leu Trp Lys Glu Tyr Ser Lys Gly Asp Ser Arg Tyr Ile
            100                 105                 110

Leu Ser Asp Ser Phe Val Val Cys Met Glu Thr Val Thr Ala Cys Leu
        115                 120                 125

Trp Gly Pro Leu Ser Leu Trp Val Val Ile Ala Phe Leu Arg Gln Gln
    130                 135                 140

Pro Phe Arg Phe Val Leu Gln Leu Val Val Ser Met Gly Gln Ile Tyr
145                 150                 155                 160

Gly Asp Val Leu Tyr Phe Leu Thr Glu Leu His Glu Gly Leu Gln His
                165                 170                 175

Gly Glu Ile Gly His Pro Val Tyr Phe Trp Phe Tyr Phe Val Phe Leu
            180                 185                 190

Asn Ala Val Trp Leu Val Ile Pro Ser Ile Leu Val Leu Asp Ala Ile
        195                 200                 205

Lys His Leu Thr Ser Ala Gln Ser Val Leu Asp Ser Lys Val Met Lys
    210                 215                 220

Ile Lys Ser Lys His Asn
225                 230

<210> SEQ ID NO 3
<211> LENGTH: 693
```

```
<212> TYPE: DNA
<213> ORGANISM: Homo sapiens
<220> FEATURE:
<221> NAME/KEY: CDS
<222> LOCATION: (1)..(693)

<400> SEQUENCE: 3 atg act acc aac gcg ggc ccc ttg cac cca tac tgg cct cag cac cta      48
Met Thr Thr Asn Ala Gly Pro Leu His Pro Tyr Trp Pro Gln His Leu
 1               5                  10                  15 aga ctg gac aac ttt gta cct aat gac cgc ccc acc tgg cat ata ctg      96
Arg Leu Asp Asn Phe Val Pro Asn Asp Arg Pro Thr Trp His Ile Leu
                20                  25                  30 gct ggc ctc ttc tct gtc aca ggg gtc tta gtc gtg acc aca tgg ctg     144
Ala Gly Leu Phe Ser Val Thr Gly Val Leu Val Val Thr Thr Trp Leu
            35                  40                  45 ttg tca ggt cgt gct gcg gtt gtc cca ttg ggg act tgg cgg cga ctg     192
Leu Ser Gly Arg Ala Ala Val Val Pro Leu Gly Thr Trp Arg Arg Leu
        50                  55                  60 tcc ctg tgc tgg ttt gca gtg tgt ggg ttc att cac ctg gtg atc gag     240
Ser Leu Cys Trp Phe Ala Val Cys Gly Phe Ile His Leu Val Ile Glu
 65                  70                  75                  80 ggc tgg ttc gtt ctc tac tac gaa gac ctg ctt gga gac caa gcc ttc     288
Gly Trp Phe Val Leu Tyr Tyr Glu Asp Leu Leu Gly Asp Gln Ala Phe
                 85                  90                  95 tta tct caa ctc tgg aaa gag tat gcc aag gga gac agc cga tac atc     336
Leu Ser Gln Leu Trp Lys Glu Tyr Ala Lys Gly Asp Ser Arg Tyr Ile
                100                 105                 110 ctg ggt gac aac ttc aca gtg tgc atg gaa acc atc aca gct tgc ctg     384
Leu Gly Asp Asn Phe Thr Val Cys Met Glu Thr Ile Thr Ala Cys Leu
            115                 120                 125 tgg gga cca ctc agc ctg tgg gtg gtg atc gcc ttt ctc cgc cag cat     432
Trp Gly Pro Leu Ser Leu Trp Val Val Ile Ala Phe Leu Arg Gln His
        130                 135                 140 ccc ctc cgc ttc att cta cag ctt gtg gtc tct gtg ggc cag atc tat     480
Pro Leu Arg Phe Ile Leu Gln Leu Val Val Ser Val Gly Gln Ile Tyr
145                 150                 155                 160 ggg gat gtg ctc tac ttc ctg aca gag cac cgc gac gga ttc cag cac     528
Gly Asp Val Leu Tyr Phe Leu Thr Glu His Arg Asp Gly Phe Gln His
                165                 170                 175 gga gag ctg ggc cac cct ctc tac ttc tgg ttt tac ttt gtc ttc atg     576
Gly Glu Leu Gly His Pro Leu Tyr Phe Trp Phe Tyr Phe Val Phe Met
            180                 185                 190 aat gcc ctg tgg ctg gtg ctg cct gga gtc ctt gtg ctt gat gct gtg     624
Asn Ala Leu Trp Leu Val Leu Pro Gly Val Leu Val Leu Asp Ala Val
        195                 200                 205 aag cac ctc act cat gcc cag agc acg ctg gat gcc aag gcc aca aaa     672
Lys His Leu Thr His Ala Gln Ser Thr Leu Asp Ala Lys Ala Thr Lys
    210                 215                 220 gcc aag agc aag aag aac tga                                         693
Ala Lys Ser Lys Lys Asn
225                 230

<210> SEQ ID NO 4
<211> LENGTH: 230
<212> TYPE: PRT
<213> ORGANISM: Homo sapiens

<400> SEQUENCE: 4

Met Thr Thr Asn Ala Gly Pro Leu His Pro Tyr Trp Pro Gln His Leu
 1               5                  10                  15
```

```
Arg Leu Asp Asn Phe Val Pro Asn Asp Arg Pro Thr Trp His Ile Leu
             20                  25                  30

Ala Gly Leu Phe Ser Val Thr Gly Val Leu Val Val Thr Thr Trp Leu
         35                  40                  45

Leu Ser Gly Arg Ala Ala Val Val Pro Leu Gly Thr Trp Arg Arg Leu
 50                  55                  60

Ser Leu Cys Trp Phe Ala Val Cys Gly Phe Ile His Leu Val Ile Glu
 65                  70                  75                  80

Gly Trp Phe Val Leu Tyr Tyr Glu Asp Leu Leu Gly Asp Gln Ala Phe
                 85                  90                  95

Leu Ser Gln Leu Trp Lys Glu Tyr Ala Lys Gly Asp Ser Arg Tyr Ile
             100                 105                 110

Leu Gly Asp Asn Phe Thr Val Cys Met Glu Thr Ile Thr Ala Cys Leu
         115                 120                 125

Trp Gly Pro Leu Ser Leu Trp Val Val Ile Ala Phe Leu Arg Gln His
130                 135                 140

Pro Leu Arg Phe Ile Leu Gln Leu Val Val Ser Val Gly Gln Ile Tyr
145                 150                 155                 160

Gly Asp Val Leu Tyr Phe Leu Thr Glu His Arg Asp Gly Phe Gln His
                 165                 170                 175

Gly Glu Leu Gly His Pro Leu Tyr Phe Trp Phe Tyr Phe Val Phe Met
             180                 185                 190

Asn Ala Leu Trp Leu Val Leu Pro Gly Val Leu Val Leu Asp Ala Val
         195                 200                 205

Lys His Leu Thr His Ala Gln Ser Thr Leu Asp Ala Lys Ala Thr Lys
210                 215                 220

Ala Lys Ser Lys Lys Asn
225                 230

<210> SEQ ID NO 5
<211> LENGTH: 669
<212> TYPE: DNA
<213> ORGANISM: Saccharomyces cerevisiae
<220> FEATURE:
<221> NAME/KEY: CDS
<222> LOCATION: (1)..(669)

<400> SEQUENCE: 5 atg aag ttt ttc cca ctc ctt ttg ttg att ggt gtt gta ggc tac att      48
Met Lys Phe Phe Pro Leu Leu Leu Leu Ile Gly Val Val Gly Tyr Ile
 1               5                  10                  15 atg aac gta ttg ttc act acc tgg ttg cca acc aat tac atg ttc gat      96
Met Asn Val Leu Phe Thr Thr Trp Leu Pro Thr Asn Tyr Met Phe Asp
             20                  25                  30 cca aaa act ttg aac gaa ata tgt aac tcg gtg att agc aaa cac aac     144
Pro Lys Thr Leu Asn Glu Ile Cys Asn Ser Val Ile Ser Lys His Asn
         35                  40                  45 gca gca gaa ggt tta tcc act gaa gac ctg tta cag gat gtc aga gac     192
Ala Ala Glu Gly Leu Ser Thr Glu Asp Leu Leu Gln Asp Val Arg Asp
 50                  55                  60 gca ctt gcc tct cat tac ggg gac gaa tac atc aac agg tac gtc aaa     240
Ala Leu Ala Ser His Tyr Gly Asp Glu Tyr Ile Asn Arg Tyr Val Lys
 65                  70                  75                  80 gaa gaa tgg gtc ttc aac aat gct ggt ggt gcg atg ggc caa atg atc     288
Glu Glu Trp Val Phe Asn Asn Ala Gly Gly Ala Met Gly Gln Met Ile
                 85                  90                  95 atc cta cac gct tcc gta tcc gag tac tta att cta ttc gga acc gct     336
Ile Leu His Ala Ser Val Ser Glu Tyr Leu Ile Leu Phe Gly Thr Ala
```

```
gtt ggt act gaa ggg cac aca ggt gtt cac ttt gct gac gac tat ttt      384
Val Gly Thr Glu Gly His Thr Gly Val His Phe Ala Asp Asp Tyr Phe
            115                 120                 125 acc atc tta cat ggt acg caa atc gca gca ttg cca tat gcc act gaa      432
Thr Ile Leu His Gly Thr Gln Ile Ala Ala Leu Pro Tyr Ala Thr Glu
130                 135                 140 gcc gaa gtt tac act cct ggt atg act cat cac ttg aag aag gga tac      480
Ala Glu Val Tyr Thr Pro Gly Met Thr His His Leu Lys Lys Gly Tyr
145                 150                 155                 160 gcc aag caa tac agc atg cca ggt ggt tcc ttt gcc ctt gaa ttg gct      528
Ala Lys Gln Tyr Ser Met Pro Gly Gly Ser Phe Ala Leu Glu Leu Ala
                165                 170                 175 caa ggc tgg att cca tgt atg ttg cca ttc ggg ttt ttg gac act ttc      576
Gln Gly Trp Ile Pro Cys Met Leu Pro Phe Gly Phe Leu Asp Thr Phe
            180                 185                 190 tcc agt act ctt gat tta tac act cta tat aga act gtc tac ctg act      624
Ser Ser Thr Leu Asp Leu Tyr Thr Leu Tyr Arg Thr Val Tyr Leu Thr
        195                 200                 205 gcc agg gac atg ggt aag aac ttg ttg caa aac aaa aag ttc taa          669
Ala Arg Asp Met Gly Lys Asn Leu Leu Gln Asn Lys Lys Phe
210                 215                 220
```

<210> SEQ ID NO 6
<211> LENGTH: 222
<212> TYPE: PRT
<213> ORGANISM: Saccharomyces cerevisiae

<400> SEQUENCE: 6

```
Met Lys Phe Phe Pro Leu Leu Leu Ile Gly Val Val Gly Tyr Ile
1               5                   10                  15

Met Asn Val Leu Phe Thr Thr Trp Leu Pro Thr Asn Tyr Met Phe Asp
                20                  25                  30

Pro Lys Thr Leu Asn Glu Ile Cys Asn Ser Val Ile Ser Lys His Asn
            35                  40                  45

Ala Ala Glu Gly Leu Ser Thr Glu Asp Leu Leu Gln Asp Val Arg Asp
        50                  55                  60

Ala Leu Ala Ser His Tyr Gly Asp Glu Tyr Ile Asn Arg Tyr Val Lys
65                  70                  75                  80

Glu Glu Trp Val Phe Asn Asn Ala Gly Gly Ala Met Gly Gln Met Ile
                85                  90                  95

Ile Leu His Ala Ser Val Ser Glu Tyr Leu Ile Leu Phe Gly Thr Ala
            100                 105                 110

Val Gly Thr Glu Gly His Thr Gly Val His Phe Ala Asp Asp Tyr Phe
        115                 120                 125

Thr Ile Leu His Gly Thr Gln Ile Ala Ala Leu Pro Tyr Ala Thr Glu
130                 135                 140

Ala Glu Val Tyr Thr Pro Gly Met Thr His His Leu Lys Lys Gly Tyr
145                 150                 155                 160

Ala Lys Gln Tyr Ser Met Pro Gly Gly Ser Phe Ala Leu Glu Leu Ala
                165                 170                 175

Gln Gly Trp Ile Pro Cys Met Leu Pro Phe Gly Phe Leu Asp Thr Phe
            180                 185                 190

Ser Ser Thr Leu Asp Leu Tyr Thr Leu Tyr Arg Thr Val Tyr Leu Thr
        195                 200                 205

Ala Arg Asp Met Gly Lys Asn Leu Leu Gln Asn Lys Lys Phe
210                 215                 220
```

```
<210> SEQ ID NO 7
<211> LENGTH: 900
<212> TYPE: DNA
<213> ORGANISM: Mus musculus
<220> FEATURE:
<221> NAME/KEY: CDS
<222> LOCATION: (1)..(900)

<400> SEQUENCE: 7 atg gac ctg gtt ctc agt gcc gcc gat tac tac ttc ttc act ccg tat        48
Met Asp Leu Val Leu Ser Ala Ala Asp Tyr Tyr Phe Phe Thr Pro Tyr
  1               5                  10                  15 gta tat cca gcc acg tgg ccc gag gac aac atc atc cga caa act att        96
Val Tyr Pro Ala Thr Trp Pro Glu Asp Asn Ile Ile Arg Gln Thr Ile
             20                  25                  30 agc ctc ctg att gtc aca aac ctg ggt gct tac att ctc tac ttc ttc       144
Ser Leu Leu Ile Val Thr Asn Leu Gly Ala Tyr Ile Leu Tyr Phe Phe
         35                  40                  45 tgt gca acc ctc agc tat tat ttt gtc tat gat cat tcc tta atg aaa       192
Cys Ala Thr Leu Ser Tyr Tyr Phe Val Tyr Asp His Ser Leu Met Lys
 50                  55                  60 cac cca cag ttt tta aag aac caa gtc tcg cgt gag atc gtg ttc act       240
His Pro Gln Phe Leu Lys Asn Gln Val Ser Arg Glu Ile Val Phe Thr
 65                  70                  75                  80 gtc aag tct ttg cct tgg atc agc atc ccc acc gtc tca cta ttc ctg       288
Val Lys Ser Leu Pro Trp Ile Ser Ile Pro Thr Val Ser Leu Phe Leu
                 85                  90                  95 ctg gag ctg agg ggt tac agc aaa ctc tac gat gac atc gga gac ttt       336
Leu Glu Leu Arg Gly Tyr Ser Lys Leu Tyr Asp Asp Ile Gly Asp Phe
            100                 105                 110 cca aat ggc tgg att cat ctc atg gtt agc gtc gta tcc ttc ctc ttt       384
Pro Asn Gly Trp Ile His Leu Met Val Ser Val Val Ser Phe Leu Phe
        115                 120                 125 ttc aca gac atg ttg atc tac agg att cat agg ggc ctg cac cac aga       432
Phe Thr Asp Met Leu Ile Tyr Arg Ile His Arg Gly Leu His His Arg
    130                 135                 140 ctg gtc tac aag cgc ata cat aaa cca cat cat att tgg aag atc ccc       480
Leu Val Tyr Lys Arg Ile His Lys Pro His His Ile Trp Lys Ile Pro
145                 150                 155                 160 acg ccg ttt gca agt cat gct ttt cac cct gtg gac ggc ttc ctt cag       528
Thr Pro Phe Ala Ser His Ala Phe His Pro Val Asp Gly Phe Leu Gln
                165                 170                 175 agt ctg cct tac cat ata tac ccc ttt gtc ttt cca ctg cac aag gtg       576
Ser Leu Pro Tyr His Ile Tyr Pro Phe Val Phe Pro Leu His Lys Val
            180                 185                 190 gtc tac tta ggt tta tat gtc ttg gtt aat gtc tgg aca att tct att       624
Val Tyr Leu Gly Leu Tyr Val Leu Val Asn Val Trp Thr Ile Ser Ile
        195                 200                 205 cat gat ggt gat ttt cgg gtt ccc cag atc tta agg cca ttt att aac       672
His Asp Gly Asp Phe Arg Val Pro Gln Ile Leu Arg Pro Phe Ile Asn
    210                 215                 220 ggg tca gct cac cac aca gac cac cac atg ttc ttt gac tat aac tat       720
Gly Ser Ala His His Thr Asp His His Met Phe Phe Asp Tyr Asn Tyr
225                 230                 235                 240 gga cag tat ttc aca ttg tgg gat aga att gga ggc tct ttt aaa cat       768
Gly Gln Tyr Phe Thr Leu Trp Asp Arg Ile Gly Gly Ser Phe Lys His
                245                 250                 255 cct tcc tct ttt gaa ggg aaa gga cca cat agt tac gtg aag aac atg       816
Pro Ser Ser Phe Glu Gly Lys Gly Pro His Ser Tyr Val Lys Asn Met
            260                 265                 270
```

```
aca gaa aaa gaa tct aac agc ttt gca gaa aac ggc tgt aaa ggc aaa         864
Thr Glu Lys Glu Ser Asn Ser Phe Ala Glu Asn Gly Cys Lys Gly Lys
        275                 280                 285 aaa gta agc aat gga gag ttt aca aag aat aag tag                         900
Lys Val Ser Asn Gly Glu Phe Thr Lys Asn Lys
    290                 295
```

<210> SEQ ID NO 8
<211> LENGTH: 299
<212> TYPE: PRT
<213> ORGANISM: Mus musculus

<400> SEQUENCE: 8

```
Met Asp Leu Val Leu Ser Ala Ala Asp Tyr Tyr Phe Phe Thr Pro Tyr
  1               5                  10                  15

Val Tyr Pro Ala Thr Trp Pro Glu Asp Asn Ile Ile Arg Gln Thr Ile
             20                  25                  30

Ser Leu Leu Ile Val Thr Asn Leu Gly Ala Tyr Ile Leu Tyr Phe Phe
         35                  40                  45

Cys Ala Thr Leu Ser Tyr Tyr Phe Val Tyr Asp His Ser Leu Met Lys
     50                  55                  60

His Pro Gln Phe Leu Lys Asn Gln Val Ser Arg Glu Ile Val Phe Thr
 65                  70                  75                  80

Val Lys Ser Leu Pro Trp Ile Ser Ile Pro Thr Val Ser Leu Phe Leu
                 85                  90                  95

Leu Glu Leu Arg Gly Tyr Ser Lys Leu Tyr Asp Asp Ile Gly Asp Phe
            100                 105                 110

Pro Asn Gly Trp Ile His Leu Met Val Ser Val Val Ser Phe Leu Phe
        115                 120                 125

Phe Thr Asp Met Leu Ile Tyr Arg Ile His Arg Gly Leu His His Arg
    130                 135                 140

Leu Val Tyr Lys Arg Ile His Lys Pro His His Ile Trp Lys Ile Pro
145                 150                 155                 160

Thr Pro Phe Ala Ser His Ala Phe His Pro Val Asp Gly Phe Leu Gln
                165                 170                 175

Ser Leu Pro Tyr His Ile Tyr Pro Phe Val Phe Pro Leu His Lys Val
            180                 185                 190

Val Tyr Leu Gly Leu Tyr Val Leu Val Asn Val Trp Thr Ile Ser Ile
        195                 200                 205

His Asp Gly Asp Phe Arg Val Pro Gln Ile Leu Arg Pro Phe Ile Asn
    210                 215                 220

Gly Ser Ala His His Thr Asp His His Met Phe Phe Asp Tyr Asn Tyr
225                 230                 235                 240

Gly Gln Tyr Phe Thr Leu Trp Asp Arg Ile Gly Gly Ser Phe Lys His
                245                 250                 255

Pro Ser Ser Phe Glu Gly Lys Gly Pro His Ser Tyr Val Lys Asn Met
            260                 265                 270

Thr Glu Lys Glu Ser Asn Ser Phe Ala Glu Asn Gly Cys Lys Gly Lys
        275                 280                 285

Lys Val Ser Asn Gly Glu Phe Thr Lys Asn Lys
    290                 295
```

<210> SEQ ID NO 9
<211> LENGTH: 900
<212> TYPE: DNA
<213> ORGANISM: Homo sapiens

<220> FEATURE:
<221> NAME/KEY: CDS
<222> LOCATION: (1)..(900)

<400> SEQUENCE: 9

```
atg gat ctt gta ctc cgt gtt gca gat tac tat ttt ttt aca cca tac      48
Met Asp Leu Val Leu Arg Val Ala Asp Tyr Tyr Phe Phe Thr Pro Tyr
 1               5                  10                  15 gtg tat cca gcc aca tgg cca gaa gat gac atc ttc cga caa gct att      96
Val Tyr Pro Ala Thr Trp Pro Glu Asp Asp Ile Phe Arg Gln Ala Ile
             20                  25                  30 agt ctt ctg att gta aca aat gtt ggt gct tac atc ctt tat ttc ttc     144
Ser Leu Leu Ile Val Thr Asn Val Gly Ala Tyr Ile Leu Tyr Phe Phe
         35                  40                  45 tgt gca aca ctg agc tat tat ttt gtc ttc gat cat gca tta atg aaa     192
Cys Ala Thr Leu Ser Tyr Tyr Phe Val Phe Asp His Ala Leu Met Lys
 50                  55                  60 cat cca caa ttt tta aag aat caa gtc cgt cga gag att aag ttt act     240
His Pro Gln Phe Leu Lys Asn Gln Val Arg Arg Glu Ile Lys Phe Thr
 65                  70                  75                  80 gtc cag gca ttg cca tgg ata agt att ctt act gtt gca ctg ttc ttg     288
Val Gln Ala Leu Pro Trp Ile Ser Ile Leu Thr Val Ala Leu Phe Leu
                 85                  90                  95 ctg gag ata aga ggt tac agc aaa tta cat gat gac cta gga gag ttt     336
Leu Glu Ile Arg Gly Tyr Ser Lys Leu His Asp Asp Leu Gly Glu Phe
            100                 105                 110 cca tat gga ttg ttt gaa ctt gtc gtt agt ata ata tct ttc ctc ttt     384
Pro Tyr Gly Leu Phe Glu Leu Val Val Ser Ile Ile Ser Phe Leu Phe
        115                 120                 125 ttc act gac atg ttc atc tac tgg att cac aga ggc ctt cat cat aga     432
Phe Thr Asp Met Phe Ile Tyr Trp Ile His Arg Gly Leu His His
    130                 135                 140 ctg gta tat aag cgc cta cat aaa cct cac cat att tgg aag att cct     480
Leu Val Tyr Lys Arg Leu His Lys Pro His His Ile Trp Lys Ile Pro
145                 150                 155                 160 act cca ttt gca agt cat gct ttt cac cct att gat ggc ttt ctt cag     528
Thr Pro Phe Ala Ser His Ala Phe His Pro Ile Asp Gly Phe Leu Gln
                165                 170                 175 agt cta cct tac cat ata tac cct ttt atc ttt cca tta cac aag gtg     576
Ser Leu Pro Tyr His Ile Tyr Pro Phe Ile Phe Pro Leu His Lys Val
            180                 185                 190 gtt tat tta agt ctg tac atc ttg gtt aat atc tgg aca att tcc att     624
Val Tyr Leu Ser Leu Tyr Ile Leu Val Asn Ile Trp Thr Ile Ser Ile
        195                 200                 205 cat gac ggt gat ttt cgt gtc ccc caa atc tta cag cca ttt att aat     672
His Asp Gly Asp Phe Arg Val Pro Gln Ile Leu Gln Pro Phe Ile Asn
    210                 215                 220 ggc tca gct cat cat aca gac cac cat atg ttc ttt gac tat aat tat     720
Gly Ser Ala His His Thr Asp His His Met Phe Phe Asp Tyr Asn Tyr
225                 230                 235                 240 gga caa tat ttc act ttg tgg gat agg att ggc ggc tca ttc aaa aat     768
Gly Gln Tyr Phe Thr Leu Trp Asp Arg Ile Gly Gly Ser Phe Lys Asn
                245                 250                 255 cct tca tcc ttt gag ggg aag gga ccg ctc agt tat gtg aag gag atg     816
Pro Ser Ser Phe Glu Gly Lys Gly Pro Leu Ser Tyr Val Lys Glu Met
            260                 265                 270 aca gag gga aag cgc agc agc cct tca gga aat ggc tgt aag aat gaa     864
Thr Glu Gly Lys Arg Ser Ser Pro Ser Gly Asn Gly Cys Lys Asn Glu
        275                 280                 285 aaa tta ttc aat gga gag ttt aca aag act gaa tag                     900
Lys Leu Phe Asn Gly Glu Phe Thr Lys Thr Glu
    290                 295
```

Lys Leu Phe Asn Gly Glu Phe Thr Lys Thr Glu
    290                 295

<210> SEQ ID NO 10
<211> LENGTH: 299
<212> TYPE: PRT
<213> ORGANISM: Homo sapiens

<400> SEQUENCE: 10

Met Asp Leu Val Leu Arg Val Ala Asp Tyr Tyr Phe Phe Thr Pro Tyr
 1               5                  10                  15

Val Tyr Pro Ala Thr Trp Pro Glu Asp Ile Phe Arg Gln Ala Ile
            20                  25                  30

Ser Leu Leu Ile Val Thr Asn Val Gly Ala Tyr Ile Leu Tyr Phe Phe
        35                  40                  45

Cys Ala Thr Leu Ser Tyr Tyr Phe Val Phe Asp His Ala Leu Met Lys
    50                  55                  60

His Pro Gln Phe Leu Lys Asn Gln Val Arg Arg Glu Ile Lys Phe Thr
 65                  70                  75                  80

Val Gln Ala Leu Pro Trp Ile Ser Ile Leu Thr Val Ala Leu Phe Leu
                85                  90                  95

Leu Glu Ile Arg Gly Tyr Ser Lys Leu His Asp Asp Leu Gly Glu Phe
            100                 105                 110

Pro Tyr Gly Leu Phe Glu Leu Val Ser Ile Ile Ser Phe Leu Phe
        115                 120                 125

Phe Thr Asp Met Phe Ile Tyr Trp Ile His Arg Gly Leu His His
    130                 135                 140

Leu Val Tyr Lys Arg Leu His Lys Pro His Ile Trp Lys Ile Pro
145                 150                 155                 160

Thr Pro Phe Ala Ser His Ala Phe His Pro Ile Asp Gly Phe Leu Gln
                165                 170                 175

Ser Leu Pro Tyr His Ile Tyr Pro Phe Ile Phe Pro Leu His Lys Val
            180                 185                 190

Val Tyr Leu Ser Leu Tyr Ile Leu Val Asn Ile Trp Thr Ile Ser Ile
        195                 200                 205

His Asp Gly Asp Phe Arg Val Pro Gln Ile Leu Gln Pro Phe Ile Asn
    210                 215                 220

Gly Ser Ala His His Thr Asp His His Met Phe Phe Asp Tyr Asn Tyr
225                 230                 235                 240

Gly Gln Tyr Phe Thr Leu Trp Asp Arg Ile Gly Gly Ser Phe Lys Asn
                245                 250                 255

Pro Ser Ser Phe Glu Gly Lys Gly Pro Leu Ser Tyr Val Lys Glu Met
            260                 265                 270

Thr Glu Gly Lys Arg Ser Ser Pro Ser Gly Asn Gly Cys Lys Asn Glu
        275                 280                 285

Lys Leu Phe Asn Gly Glu Phe Thr Lys Thr Glu
    290                 295

<210> SEQ ID NO 11
<211> LENGTH: 1098
<212> TYPE: DNA
<213> ORGANISM: Saccharomyces cerevisiae
<220> FEATURE:
<221> NAME/KEY: CDS
<222> LOCATION: (1)..(1098)

<400> SEQUENCE: 11

-continued

| | |
|---|---|
| atg gat ttg gtc tta gaa gtc gct gac cat tat gtc tta gac gac ttg<br>Met Asp Leu Val Leu Glu Val Ala Asp His Tyr Val Leu Asp Asp Leu<br>1                     5                        10                    15 | 48 |
| tac gct aaa gtt ctg ccc gct tcg ttg gca gct aat att cct gtc aag<br>Tyr Ala Lys Val Leu Pro Ala Ser Leu Ala Ala Asn Ile Pro Val Lys<br>              20                       25                        30 | 96 |
| tgg cag aaa ttg cta ggg ttg aac agt ggg ttc agc aat tct acg att<br>Trp Gln Lys Leu Leu Gly Leu Asn Ser Gly Phe Ser Asn Ser Thr Ile<br>        35                       40                        45 | 144 |
| ttg cag gag act ttg aac tcc aag aat gcc gtc aaa gaa tgt aga agg<br>Leu Gln Glu Thr Leu Asn Ser Lys Asn Ala Val Lys Glu Cys Arg Arg<br>      50                       55                        60 | 192 |
| ttc tac ggg cag gtg cca ttc ctg ttt gat atg tcg acg tct ttt<br>Phe Tyr Gly Gln Val Pro Phe Leu Phe Asp Met Ser Thr Thr Ser Phe<br>65                     70                       75                    80 | 240 |
| gca tcg cta ttg cct cgt tcc agc atc ttg aga gaa ttc ctc tca cta<br>Ala Ser Leu Leu Pro Arg Ser Ser Ile Leu Arg Glu Phe Leu Ser Leu<br>                  85                       90                    95 | 288 |
| tgg gtt att gtt acg atc ttt ggt tta cta ctt tac tta ttc acg gct<br>Trp Val Ile Val Thr Ile Phe Gly Leu Leu Leu Tyr Leu Phe Thr Ala<br>              100                       105                    110 | 336 |
| agt ctc agc tac gtg ttt gtg ttt gac aag tcg att ttc aac cat cct<br>Ser Leu Ser Tyr Val Phe Val Phe Asp Lys Ser Ile Phe Asn His Pro<br>          115                       120                    125 | 384 |
| cgt tac ttg aaa aac caa atg gca atg gaa atc aag ttg gca gtc agt<br>Arg Tyr Leu Lys Asn Gln Met Ala Met Glu Ile Lys Leu Ala Val Ser<br>      130                      135                    140 | 432 |
| gct atc cca tgg atg tcg atg ttg acc gtt cca tgg ttt gtt atg gaa<br>Ala Ile Pro Trp Met Ser Met Leu Thr Val Pro Trp Phe Val Met Glu<br>145                     150                       155                    160 | 480 |
| ttg aac ggc cat tct aaa cta tac atg aag att gat tat gaa aac cac<br>Leu Asn Gly His Ser Lys Leu Tyr Met Lys Ile Asp Tyr Glu Asn His<br>              165                       170                    175 | 528 |
| ggt gta agg aag ctc att atc gag tac ttc act ttc atc ttt ttc act<br>Gly Val Arg Lys Leu Ile Ile Glu Tyr Phe Thr Phe Ile Phe Phe Thr<br>      180                      185                    190 | 576 |
| gat tgc ggt gtg tat tta gcg cac aga tgg ttg cat tgg cca agg gtc<br>Asp Cys Gly Val Tyr Leu Ala His Arg Trp Leu His Trp Pro Arg Val<br>          195                       200                    205 | 624 |
| tac cgt gct ctg cac aag cct cat cac aag tgg ctg gtc tgc aca cct<br>Tyr Arg Ala Leu His Lys Pro His His Lys Trp Leu Val Cys Thr Pro<br>      210                      215                    220 | 672 |
| ttc gca tct cat tct ttc cat cct gta gac ggg ttt ttg caa tcc atc<br>Phe Ala Ser His Ser Phe His Pro Val Asp Gly Phe Leu Gln Ser Ile<br>225                     230                       235                    240 | 720 |
| tcg tac cac atc tac cca ttg att ctg cca tta cac aag gtt tct tat<br>Ser Tyr His Ile Tyr Pro Leu Ile Leu Pro Leu His Lys Val Ser Tyr<br>              245                       250                    255 | 768 |
| ttg att ctg ttc act ttt gtt aac ttt tgg act gtt atg att cat gac<br>Leu Ile Leu Phe Thr Phe Val Asn Phe Trp Thr Val Met Ile His Asp<br>      260                      265                    270 | 816 |
| ggt caa tac cta tca aac aat cct gcc gtc aac ggt act gcc tgc cac<br>Gly Gln Tyr Leu Ser Asn Asn Pro Ala Val Asn Gly Thr Ala Cys His<br>          275                       280                    285 | 864 |
| acg gtt cac cat cta tat ttc aac tac aac tac ggt caa ttc acc act<br>Thr Val His His Leu Tyr Phe Asn Tyr Asn Tyr Gly Gln Phe Thr Thr<br>      290                      295                    300 | 912 |
| ctg tgg gac aga cta ggg ggt tct tac cgt aga cca gat gac tca ttg<br>Leu Trp Asp Arg Leu Gly Gly Ser Tyr Arg Arg Pro Asp Asp Ser Leu<br>305                     310                       315                    320 | 960 |

```
ttt gat cct aag tta aga gat gct aag gag acc tgg gac gct caa gtt    1008
Phe Asp Pro Lys Leu Arg Asp Ala Lys Glu Thr Trp Asp Ala Gln Val
            325                 330                 335 aag gaa gtt gaa cat ttc atc aag gag gtc gaa ggt gat gat aat gat    1056
Lys Glu Val Glu His Phe Ile Lys Glu Val Glu Gly Asp Asp Asn Asp
        340                 345                 350 aga atc tat gaa aac gac cca aat acc aag aag aac aac tga            1098
Arg Ile Tyr Glu Asn Asp Pro Asn Thr Lys Lys Asn Asn
355                 360                 365

<210> SEQ ID NO 12
<211> LENGTH: 365
<212> TYPE: PRT
<213> ORGANISM: Saccharomyces cerevisiae

<400> SEQUENCE: 12

Met Asp Leu Val Leu Glu Val Ala Asp His Tyr Val Leu Asp Asp Leu
1               5                   10                  15

Tyr Ala Lys Val Leu Pro Ala Ser Leu Ala Ala Asn Ile Pro Val Lys
                20                  25                  30

Trp Gln Lys Leu Leu Gly Leu Asn Ser Gly Phe Ser Asn Ser Thr Ile
            35                  40                  45

Leu Gln Glu Thr Leu Asn Ser Lys Asn Ala Val Lys Glu Cys Arg Arg
        50                  55                  60

Phe Tyr Gly Gln Val Pro Phe Leu Phe Asp Met Ser Thr Thr Ser Phe
65                  70                  75                  80

Ala Ser Leu Leu Pro Arg Ser Ser Ile Leu Arg Glu Phe Leu Ser Leu
                85                  90                  95

Trp Val Ile Val Thr Ile Phe Gly Leu Leu Leu Tyr Leu Phe Thr Ala
            100                 105                 110

Ser Leu Ser Tyr Val Phe Val Phe Asp Lys Ser Ile Phe Asn His Pro
        115                 120                 125

Arg Tyr Leu Lys Asn Gln Met Ala Met Glu Ile Lys Leu Ala Val Ser
    130                 135                 140

Ala Ile Pro Trp Met Ser Met Leu Thr Val Pro Trp Phe Val Met Glu
145                 150                 155                 160

Leu Asn Gly His Ser Lys Leu Tyr Met Lys Ile Asp Tyr Glu Asn His
                165                 170                 175

Gly Val Arg Lys Leu Ile Ile Glu Tyr Phe Thr Phe Ile Phe Phe Thr
            180                 185                 190

Asp Cys Gly Val Tyr Leu Ala His Arg Trp Leu His Trp Pro Arg Val
        195                 200                 205

Tyr Arg Ala Leu His Lys Pro His His Lys Trp Leu Val Cys Thr Pro
    210                 215                 220

Phe Ala Ser His Ser Phe His Pro Val Asp Gly Phe Leu Gln Ser Ile
225                 230                 235                 240

Ser Tyr His Ile Tyr Pro Leu Ile Leu Pro Leu His Lys Val Ser Tyr
                245                 250                 255

Leu Ile Leu Phe Thr Phe Val Asn Phe Trp Thr Val Met Ile His Asp
            260                 265                 270

Gly Gln Tyr Leu Ser Asn Asn Pro Ala Val Asn Gly Thr Ala Cys His
        275                 280                 285

Thr Val His His Leu Tyr Phe Asn Tyr Asn Tyr Gly Gln Phe Thr Thr
    290                 295                 300

Leu Trp Asp Arg Leu Gly Gly Ser Tyr Arg Arg Pro Asp Asp Ser Leu
```

-continued

```
             305                 310                 315                 320
    Phe Asp Pro Lys Leu Arg Asp Ala Lys Glu Thr Trp Asp Ala Gln Val
                     325                 330                 335

Lys Glu Val Glu His Phe Ile Lys Glu Val Glu Gly Asp Asp Asn Asp
                340                 345                 350

Arg Ile Tyr Glu Asn Asp Pro Asn Thr Lys Lys Asn Asn
                355                 360                 365

<210> SEQ ID NO 13
<211> LENGTH: 1557
<212> TYPE: DNA
<213> ORGANISM: Mus musculus
<220> FEATURE:
<221> NAME/KEY: CDS
<222> LOCATION: (1)..(1557)

<400> SEQUENCE: 13 atg gag ccc gcc gtg tcg ctg gcc gtg tgc gcg ctg ctc ttt ctg ctc      48
Met Glu Pro Ala Val Ser Leu Ala Val Cys Ala Leu Leu Phe Leu Leu
  1               5                  10                  15 tgg gtg cga gtg aag ggg ttg gag ttc gtt ctc atc cac cag cgc tgg      96
Trp Val Arg Val Lys Gly Leu Glu Phe Val Leu Ile His Gln Arg Trp
             20                  25                  30 gtg ttc gtg tgc ctc ttc ttg ctg ccg ctc tcg ctc atc ttc gat atc     144
Val Phe Val Cys Leu Phe Leu Leu Pro Leu Ser Leu Ile Phe Asp Ile
         35                  40                  45 tac tac tac gtg cgc gcc tgg gtg gtg ttc aag ctg agc agt gcg ccg     192
Tyr Tyr Tyr Val Arg Ala Trp Val Val Phe Lys Leu Ser Ser Ala Pro
     50                  55                  60 cgc ctg cac gag cag cgc gtg cgg gac atc cag aaa cag gtc cgg gaa     240
Arg Leu His Glu Gln Arg Val Arg Asp Ile Gln Lys Gln Val Arg Glu
 65                  70                  75                  80 tgg aag gaa cag ggc agt aag acc ttc atg tgc acg ggg cgc cca ggc     288
Trp Lys Glu Gln Gly Ser Lys Thr Phe Met Cys Thr Gly Arg Pro Gly
                 85                  90                  95 tgg ctc act gtc tcg ctg cga gtc gga aag tac aag aag acc cat aag     336
Trp Leu Thr Val Ser Leu Arg Val Gly Lys Tyr Lys Lys Thr His Lys
            100                 105                 110 aac atc atg atc aac ctg atg gac atc ctg gag gtg gac acc aag aaa     384
Asn Ile Met Ile Asn Leu Met Asp Ile Leu Glu Val Asp Thr Lys Lys
        115                 120                 125 cag att gtt cga gtg gag ccc ttg gtg tct atg ggt cag gtg aca gct     432
Gln Ile Val Arg Val Glu Pro Leu Val Ser Met Gly Gln Val Thr Ala
    130                 135                 140 ttg ctg aac tcc att ggc tgg acc ctg cct gtg ttg cct gag ctt gat     480
Leu Leu Asn Ser Ile Gly Trp Thr Leu Pro Val Leu Pro Glu Leu Asp
145                 150                 155                 160 gac ctc aca gtg ggg ggc ctg atc atg ggc aca ggc atc gag tca tcg     528
Asp Leu Thr Val Gly Gly Leu Ile Met Gly Thr Gly Ile Glu Ser Ser
                165                 170                 175 tcc cac aag tat ggc ctg ttc caa cac att tgc act gcc tac gag ctg     576
Ser His Lys Tyr Gly Leu Phe Gln His Ile Cys Thr Ala Tyr Glu Leu
            180                 185                 190 atc ctg gca gac ggc agc ttt gtg cgc tgc aca ccg tct gaa aac tca     624
Ile Leu Ala Asp Gly Ser Phe Val Arg Cys Thr Pro Ser Glu Asn Ser
        195                 200                 205 gac ctg ttc tat gcc gtg ccc tgg tcc tgt ggg acc ctg ggc ttc ctg     672
Asp Leu Phe Tyr Ala Val Pro Trp Ser Cys Gly Thr Leu Gly Phe Leu
    210                 215                 220 gtg gct gcc gag atc cgg atc atc ccg gcc aag aag tat gtc aag ctg     720
```

-continued

```
                Val Ala Ala Glu Ile Arg Ile Ile Pro Ala Lys Lys Tyr Val Lys Leu
                225                 230                 235                 240 cgg ttt gag cct gtt cgg ggc ctg gag gcc atc tgt gaa aaa ttc acc              768
Arg Phe Glu Pro Val Arg Gly Leu Glu Ala Ile Cys Glu Lys Phe Thr
                245                 250                 255 cgc gag tcc cag cgg ctg gag aac cac ttc gtg gaa ggg ttg ctg tac              816
Arg Glu Ser Gln Arg Leu Glu Asn His Phe Val Glu Gly Leu Leu Tyr
                260                 265                 270 tcc ctg gat gag gct gtg gct gtc atc atg aca ggg gtc atg acg gac              864
Ser Leu Asp Glu Ala Val Ala Val Ile Met Thr Gly Val Met Thr Asp
            275                 280                 285 gac gta gag tcc agc aag ctg aat agc att ggc agt tac tac aag ccc              912
Asp Val Glu Ser Ser Lys Leu Asn Ser Ile Gly Ser Tyr Tyr Lys Pro
        290                 295                 300 tgg ttc ttc aag cat gtg gag aac tac ctg aag aca aac cgg gag ggc              960
Trp Phe Phe Lys His Val Glu Asn Tyr Leu Lys Thr Asn Arg Glu Gly
305                 310                 315                 320 ctc gaa tac att ccc ctg aga cac tac tac cac cga cac acg cgc agc             1008
Leu Glu Tyr Ile Pro Leu Arg His Tyr Tyr His Arg His Thr Arg Ser
                325                 330                 335 atc ttc tgg gag ctc cag gac atc atc cct ttc ggc aac aac ccc atc             1056
Ile Phe Trp Glu Leu Gln Asp Ile Ile Pro Phe Gly Asn Asn Pro Ile
                340                 345                 350 ttc cgc tac ctc ttc ggc tgg atg gtg cct ccc aag atc tcc ctc ctg             1104
Phe Arg Tyr Leu Phe Gly Trp Met Val Pro Pro Lys Ile Ser Leu Leu
                355                 360                 365 aag ctg acc cag ggc gag acg cta cgc aag ctg tac gag cag cac cac             1152
Lys Leu Thr Gln Gly Glu Thr Leu Arg Lys Leu Tyr Glu Gln His His
            370                 375                 380 gtg gtg cag gac atg ctg gtg ccc atg aag tgc atg tca cag gcc ctg             1200
Val Val Gln Asp Met Leu Val Pro Met Lys Cys Met Ser Gln Ala Leu
385                 390                 395                 400 cat acc ttc caa aat gac atc cac gtc tac ccc atc tgg ctg tgc cca             1248
His Thr Phe Gln Asn Asp Ile His Val Tyr Pro Ile Trp Leu Cys Pro
                405                 410                 415 ttc atc ctg ccc agc cag cca gga cta gtg cat ccc aag gga gat gaa             1296
Phe Ile Leu Pro Ser Gln Pro Gly Leu Val His Pro Lys Gly Asp Glu
                420                 425                 430 gca gag ctc tac gtg gac atc ggg gca tac ggg gag cca cgt gtg aag             1344
Ala Glu Leu Tyr Val Asp Ile Gly Ala Tyr Gly Glu Pro Arg Val Lys
                435                 440                 445 cac ttc gag gcc agg tcc tgc atg agg cag ctg gag aag ttt gtg cgg             1392
His Phe Glu Ala Arg Ser Cys Met Arg Gln Leu Glu Lys Phe Val Arg
            450                 455                 460 agt gtg cac ggg ttc caa atg tta tac gcc gat tgc tat atg aac cgc             1440
Ser Val His Gly Phe Gln Met Leu Tyr Ala Asp Cys Tyr Met Asn Arg
465                 470                 475                 480 gag gaa ttc tgg gag atg ttc gat ggc tcc ttg tac cac aag ctg cgc             1488
Glu Glu Phe Trp Glu Met Phe Asp Gly Ser Leu Tyr His Lys Leu Arg
                485                 490                 495 aag cag ctg ggc tgc cag gac gcc ttc cct gag gtg tac gac aag atc             1536
Lys Gln Leu Gly Cys Gln Asp Ala Phe Pro Glu Val Tyr Asp Lys Ile
                500                 505                 510 tgc aag gcg gca agg cac tga                                                  1557
Cys Lys Ala Ala Arg His
            515

<210> SEQ ID NO 14
<211> LENGTH: 518
<212> TYPE: PRT
```

<213> ORGANISM: Mus musculus

<400> SEQUENCE: 14

Met Glu Pro Ala Val Ser Leu Ala Val Cys Ala Leu Leu Phe Leu Leu
 1               5                  10                  15

Trp Val Arg Val Lys Gly Leu Glu Phe Val Leu Ile His Gln Arg Trp
             20                  25                  30

Val Phe Val Cys Leu Phe Leu Leu Pro Leu Ser Leu Ile Phe Asp Ile
         35                  40                  45

Tyr Tyr Tyr Val Arg Ala Trp Val Val Phe Lys Leu Ser Ser Ala Pro
     50                  55                  60

Arg Leu His Glu Gln Arg Val Arg Asp Ile Gln Lys Gln Val Arg Glu
 65                  70                  75                  80

Trp Lys Glu Gln Gly Ser Lys Thr Phe Met Cys Thr Gly Arg Pro Gly
                 85                  90                  95

Trp Leu Thr Val Ser Leu Arg Val Gly Lys Tyr Lys Lys Thr His Lys
            100                 105                 110

Asn Ile Met Ile Asn Leu Met Asp Ile Leu Glu Val Asp Thr Lys Lys
        115                 120                 125

Gln Ile Val Arg Val Glu Pro Leu Val Ser Met Gly Gln Val Thr Ala
    130                 135                 140

Leu Leu Asn Ser Ile Gly Trp Thr Leu Pro Val Leu Pro Glu Leu Asp
145                 150                 155                 160

Asp Leu Thr Val Gly Gly Leu Ile Met Gly Thr Gly Ile Glu Ser Ser
                165                 170                 175

Ser His Lys Tyr Gly Leu Phe Gln His Ile Cys Thr Ala Tyr Glu Leu
            180                 185                 190

Ile Leu Ala Asp Gly Ser Phe Val Arg Cys Thr Pro Ser Glu Asn Ser
        195                 200                 205

Asp Leu Phe Tyr Ala Val Pro Trp Ser Cys Gly Thr Leu Gly Phe Leu
    210                 215                 220

Val Ala Ala Glu Ile Arg Ile Ile Pro Ala Lys Lys Tyr Val Lys Leu
225                 230                 235                 240

Arg Phe Glu Pro Val Arg Gly Leu Glu Ala Ile Cys Glu Lys Phe Thr
                245                 250                 255

Arg Glu Ser Gln Arg Leu Glu Asn His Phe Val Glu Gly Leu Leu Tyr
            260                 265                 270

Ser Leu Asp Glu Ala Val Ala Val Ile Met Thr Gly Val Met Thr Asp
        275                 280                 285

Asp Val Glu Ser Ser Lys Leu Asn Ser Ile Gly Ser Tyr Tyr Lys Pro
    290                 295                 300

Trp Phe Phe Lys His Val Glu Asn Tyr Leu Lys Thr Asn Arg Glu Gly
305                 310                 315                 320

Leu Glu Tyr Ile Pro Leu Arg His Tyr Tyr His Arg His Thr Arg Ser
                325                 330                 335

Ile Phe Trp Glu Leu Gln Asp Ile Ile Pro Phe Gly Asn Asn Pro Ile
            340                 345                 350

Phe Arg Tyr Leu Phe Gly Trp Met Val Pro Pro Lys Ile Ser Leu Leu
        355                 360                 365

Lys Leu Thr Gln Gly Glu Thr Leu Arg Lys Leu Tyr Glu Gln His His
    370                 375                 380

Val Val Gln Asp Met Leu Val Pro Met Lys Cys Met Ser Gln Ala Leu
385                 390                 395                 400

```
His Thr Phe Gln Asn Asp Ile His Val Tyr Pro Ile Trp Leu Cys Pro
            405                 410                 415

Phe Ile Leu Pro Ser Gln Pro Gly Leu Val His Pro Lys Gly Asp Glu
        420                 425                 430

Ala Glu Leu Tyr Val Asp Ile Gly Ala Tyr Gly Glu Pro Arg Val Lys
                435                 440                 445

His Phe Glu Ala Arg Ser Cys Met Arg Gln Leu Glu Lys Phe Val Arg
    450                 455                 460

Ser Val His Gly Phe Gln Met Leu Tyr Ala Asp Cys Tyr Met Asn Arg
465                 470                 475                 480

Glu Glu Phe Trp Glu Met Phe Asp Gly Ser Leu Tyr His Lys Leu Arg
                485                 490                 495

Lys Gln Leu Gly Cys Gln Asp Ala Phe Pro Glu Val Tyr Asp Lys Ile
            500                 505                 510

Cys Lys Ala Ala Arg His
        515

<210> SEQ ID NO 15
<211> LENGTH: 1551
<212> TYPE: DNA
<213> ORGANISM: Homo sapiens
<220> FEATURE:
<221> NAME/KEY: CDS
<222> LOCATION: (1)..(1551)

<400> SEQUENCE: 15 atg gag ccc gcc gtg tcg ctg gcc gtg tgc gcg ctg ctc ttc ctg ctg      48
Met Glu Pro Ala Val Ser Leu Ala Val Cys Ala Leu Leu Phe Leu Leu
 1               5                  10                  15 tgg gtg cgc ctg aag ggg ctg gag ttc gtg ctc atc cac cag cgc tgg      96
Trp Val Arg Leu Lys Gly Leu Glu Phe Val Leu Ile His Gln Arg Trp
             20                  25                  30 gtg ttc gtg tgc ctc ttc ctc ctg ccg ctc tcg ctt atc ttc gat atc     144
Val Phe Val Cys Leu Phe Leu Leu Pro Leu Ser Leu Ile Phe Asp Ile
         35                  40                  45 tac tac tac gtg cgc gcc tgg gtg gtg ttc aag ctc agc agc gct ccg     192
Tyr Tyr Tyr Val Arg Ala Trp Val Val Phe Lys Leu Ser Ser Ala Pro
     50                  55                  60 cgc ctg cac gag cag cgc gtg cgg gac atc cag aag cag gtg cgg gaa     240
Arg Leu His Glu Gln Arg Val Arg Asp Ile Gln Lys Gln Val Arg Glu
 65                  70                  75                  80 tgg aag gag cag ggt agc aag acc ttc atg tgc acg ggg cgc cct ggc     288
Trp Lys Glu Gln Gly Ser Lys Thr Phe Met Cys Thr Gly Arg Pro Gly
                 85                  90                  95 tgg ctc act gtc tca cta cgt gtc ggg aag tac aag aag aca cac aaa     336
Trp Leu Thr Val Ser Leu Arg Val Gly Lys Tyr Lys Lys Thr His Lys
            100                 105                 110 aac atc atg atc aac ctg atg gac att ctg gaa gtg gac acc aag aaa     384
Asn Ile Met Ile Asn Leu Met Asp Ile Leu Glu Val Asp Thr Lys Lys
        115                 120                 125 cag att gtc cgt gtg gag ccc ttg gtg acc atg ggc cag gtg act gcc     432
Gln Ile Val Arg Val Glu Pro Leu Val Thr Met Gly Gln Val Thr Ala
    130                 135                 140 ctg ctg acc tcc att ggc tgg act ctc ccc gtg ttg cct gag ctt gat     480
Leu Leu Thr Ser Ile Gly Trp Thr Leu Pro Val Leu Pro Glu Leu Asp
145                 150                 155                 160 gac ctc aca gtg ggg ggc ttg atc atg ggc aca ggc atc gag tca tca     528
Asp Leu Thr Val Gly Gly Leu Ile Met Gly Thr Gly Ile Glu Ser Ser
                165                 170                 175
```

```
tcc cac aag tac ggc ctg ttc caa cac atc tgc act gct tac gag ctg      576
Ser His Lys Tyr Gly Leu Phe Gln His Ile Cys Thr Ala Tyr Glu Leu
        180                 185                 190 gtc ctg gct gat ggc agc ttt gtg cga tgc act ccg tcc gaa aac tca      624
Val Leu Ala Asp Gly Ser Phe Val Arg Cys Thr Pro Ser Glu Asn Ser
            195                 200                 205 gac ctg ttc tat gcc gta ccc tgg tcc tgt ggg acg ctg ggt ttc ctg      672
Asp Leu Phe Tyr Ala Val Pro Trp Ser Cys Gly Thr Leu Gly Phe Leu
    210                 215                 220 gtg gcc gct gag atc cgc atc atc cct gcc aag aag tac gtc aag ctg      720
Val Ala Ala Glu Ile Arg Ile Ile Pro Ala Lys Lys Tyr Val Lys Leu
225                 230                 235                 240 cgt ttc gag cca gtg cgg ggc ctg gag gct atc tgt gcc aag ttc acc      768
Arg Phe Glu Pro Val Arg Gly Leu Glu Ala Ile Cys Ala Lys Phe Thr
                245                 250                 255 cac gag tcc cag cgg cag gag aac cac ttc gtg gaa ggg ctg ctc tac      816
His Glu Ser Gln Arg Gln Glu Asn His Phe Val Glu Gly Leu Leu Tyr
            260                 265                 270 tcc ctg gat gag gct gtc att atg aca ggg gtc atg aca gat gag gca      864
Ser Leu Asp Glu Ala Val Ile Met Thr Gly Val Met Thr Asp Glu Ala
    275                 280                 285 gag ccc agc aag ctg aat agc att ggc aat tac tac aag ccg tgg ttc      912
Glu Pro Ser Lys Leu Asn Ser Ile Gly Asn Tyr Tyr Lys Pro Trp Phe
290                 295                 300 ttt aag cat gtg gag aac tat ctg aag aca aac cga gag ggc ctg gag      960
Phe Lys His Val Glu Asn Tyr Leu Lys Thr Asn Arg Glu Gly Leu Glu
305                 310                 315                 320 tac att ccc ttg aga cac tac tac cac cgc cac acg cgc agc atc ttc     1008
Tyr Ile Pro Leu Arg His Tyr Tyr His Arg His Thr Arg Ser Ile Phe
                325                 330                 335 tgg gag ctc cag gac atc atc ccc ttt ggc aac aac ccc atc ttc cgc     1056
Trp Glu Leu Gln Asp Ile Ile Pro Phe Gly Asn Asn Pro Ile Phe Arg
            340                 345                 350 tac ctc ttt ggc tgg atg gtg cct ccc aag atc tcc ctc ctg aag ctg     1104
Tyr Leu Phe Gly Trp Met Val Pro Pro Lys Ile Ser Leu Leu Lys Leu
    355                 360                 365 acc cag ggt gag acc ctg cgc aag ctg tac gag cag cac cac gtg gtg     1152
Thr Gln Gly Glu Thr Leu Arg Lys Leu Tyr Glu Gln His His Val Val
370                 375                 380 cag gac atg ctg gtg ccc atg aag tgc ctg cag cag gcc ctg cac acc     1200
Gln Asp Met Leu Val Pro Met Lys Cys Leu Gln Gln Ala Leu His Thr
385                 390                 395                 400 ttc caa aac gac atc cac gtc tac ccc atc tgg ctg tgt ccg ttc atc     1248
Phe Gln Asn Asp Ile His Val Tyr Pro Ile Trp Leu Cys Pro Phe Ile
                405                 410                 415 ctg ccc agc cag cca ggc tta gtg cac ccc aaa gga aat gag gca gag     1296
Leu Pro Ser Gln Pro Gly Leu Val His Pro Lys Gly Asn Glu Ala Glu
            420                 425                 430 ctc tac atc gac att gga gca tat ggg gag ccg cgt gtg aaa cac ttt     1344
Leu Tyr Ile Asp Ile Gly Ala Tyr Gly Glu Pro Arg Val Lys His Phe
    435                 440                 445 gaa gcc agg tcc tgc atg agg cag ctg gag aag ttt gtc cgc agc gtg     1392
Glu Ala Arg Ser Cys Met Arg Gln Leu Glu Lys Phe Val Arg Ser Val
450                 455                 460 cat ggc ttc cag atg ctg tat gcc gac tgc tac atg aac cgg gag gag     1440
His Gly Phe Gln Met Leu Tyr Ala Asp Cys Tyr Met Asn Arg Glu Glu
465                 470                 475                 480 ttc tgg gag atg ttt gat ggc tcc ttg tac cac aag ctg cga gag aag     1488
Phe Trp Glu Met Phe Asp Gly Ser Leu Tyr His Lys Leu Arg Glu Lys
                485                 490                 495
```

```
ctg ggt tgc cag gac gcc ttc ccc gag gtg tac gac aag atc tgc aag    1536
Leu Gly Cys Gln Asp Ala Phe Pro Glu Val Tyr Asp Lys Ile Cys Lys
        500                 505                 510 gcc gcc agg cac tga                                                1551
Ala Ala Arg His
        515
```

<210> SEQ ID NO 16
<211> LENGTH: 516
<212> TYPE: PRT
<213> ORGANISM: Homo sapiens

<400> SEQUENCE: 16

```
Met Glu Pro Ala Val Ser Leu Ala Val Cys Ala Leu Leu Phe Leu Leu
 1               5                  10                  15

Trp Val Arg Leu Lys Gly Leu Glu Phe Val Leu Ile His Gln Arg Trp
            20                  25                  30

Val Phe Val Cys Leu Phe Leu Leu Pro Leu Ser Leu Ile Phe Asp Ile
        35                  40                  45

Tyr Tyr Tyr Val Arg Ala Trp Val Val Phe Lys Leu Ser Ser Ala Pro
    50                  55                  60

Arg Leu His Glu Gln Arg Val Arg Asp Ile Gln Lys Gln Val Arg Glu
65                  70                  75                  80

Trp Lys Glu Gln Gly Ser Lys Thr Phe Met Cys Thr Gly Arg Pro Gly
                85                  90                  95

Trp Leu Thr Val Ser Leu Arg Val Gly Lys Tyr Lys Lys Thr His Lys
            100                 105                 110

Asn Ile Met Ile Asn Leu Met Asp Ile Leu Glu Val Asp Thr Lys Lys
        115                 120                 125

Gln Ile Val Arg Val Glu Pro Leu Val Thr Met Gly Gln Val Thr Ala
    130                 135                 140

Leu Leu Thr Ser Ile Gly Trp Thr Leu Pro Val Leu Pro Glu Leu Asp
145                 150                 155                 160

Asp Leu Thr Val Gly Gly Leu Ile Met Gly Thr Gly Ile Glu Ser Ser
                165                 170                 175

Ser His Lys Tyr Gly Leu Phe Gln His Ile Cys Thr Ala Tyr Glu Leu
            180                 185                 190

Val Leu Ala Asp Gly Ser Phe Val Arg Cys Thr Pro Ser Glu Asn Ser
        195                 200                 205

Asp Leu Phe Tyr Ala Val Pro Trp Ser Cys Gly Thr Leu Gly Phe Leu
    210                 215                 220

Val Ala Ala Glu Ile Arg Ile Ile Pro Ala Lys Lys Tyr Val Lys Leu
225                 230                 235                 240

Arg Phe Glu Pro Val Arg Gly Leu Glu Ala Ile Cys Ala Lys Phe Thr
                245                 250                 255

His Glu Ser Gln Arg Gln Glu Asn His Phe Val Glu Gly Leu Leu Tyr
            260                 265                 270

Ser Leu Asp Glu Ala Val Ile Met Thr Gly Val Met Thr Asp Glu Ala
        275                 280                 285

Glu Pro Ser Lys Leu Asn Ser Ile Gly Asn Tyr Tyr Lys Pro Trp Phe
    290                 295                 300

Phe Lys His Val Glu Asn Tyr Leu Lys Thr Asn Arg Glu Gly Leu Glu
305                 310                 315                 320

Tyr Ile Pro Leu Arg His Tyr Tyr His Arg His Thr Arg Ser Ile Phe
                325                 330                 335
```

-continued

```
Trp Glu Leu Gln Asp Ile Ile Pro Phe Gly Asn Asn Pro Ile Phe Arg
            340                 345                 350

Tyr Leu Phe Gly Trp Met Val Pro Pro Lys Ile Ser Leu Leu Lys Leu
        355                 360                 365

Thr Gln Gly Glu Thr Leu Arg Lys Leu Tyr Glu Gln His His Val Val
    370                 375                 380

Gln Asp Met Leu Val Pro Met Lys Cys Leu Gln Gln Ala Leu His Thr
385                 390                 395                 400

Phe Gln Asn Asp Ile His Val Tyr Pro Ile Trp Leu Cys Pro Phe Ile
                405                 410                 415

Leu Pro Ser Gln Pro Gly Leu Val His Pro Lys Gly Asn Glu Ala Glu
            420                 425                 430

Leu Tyr Ile Asp Ile Gly Ala Tyr Gly Glu Pro Arg Val Lys His Phe
        435                 440                 445

Glu Ala Arg Ser Cys Met Arg Gln Leu Glu Lys Phe Val Arg Ser Val
    450                 455                 460

His Gly Phe Gln Met Leu Tyr Ala Asp Cys Tyr Met Asn Arg Glu Glu
465                 470                 475                 480

Phe Trp Glu Met Phe Asp Gly Ser Leu Tyr His Lys Leu Arg Glu Lys
                485                 490                 495

Leu Gly Cys Gln Asp Ala Phe Pro Glu Val Tyr Asp Lys Ile Cys Lys
            500                 505                 510

Ala Ala Arg His
        515
```

<210> SEQ ID NO 17
<211> LENGTH: 1422
<212> TYPE: DNA
<213> ORGANISM: Saccharomyces cerevisiae
<220> FEATURE:
<221> NAME/KEY: CDS
<222> LOCATION: (1)..(1422)

<400> SEQUENCE: 17

```
atg gca aag gat aat agt gag aag ctg cag gtg cag gga gag gag aaa      48
Met Ala Lys Asp Asn Ser Glu Lys Leu Gln Val Gln Gly Glu Glu Lys
 1               5                  10                  15 aag tcc aag caa ccg gtt aat ttc ctg cct cag ggt aaa tgg ctg aag      96
Lys Ser Lys Gln Pro Val Asn Phe Leu Pro Gln Gly Lys Trp Leu Lys
             20                  25                  30 cca aat gaa atc gaa tat gag ttt ggt ggg act act ggt gtt att ggt     144
Pro Asn Glu Ile Glu Tyr Glu Phe Gly Gly Thr Thr Gly Val Ile Gly
         35                  40                  45 atg ctg atc ggg ttt cca ctg cta atg tac tat atg tgg att tgt gcg     192
Met Leu Ile Gly Phe Pro Leu Leu Met Tyr Tyr Met Trp Ile Cys Ala
     50                  55                  60 gaa ttt tat cac ggt aag gtt gcc cta ccc aag gct ggt gaa tcg tgg     240
Glu Phe Tyr His Gly Lys Val Ala Leu Pro Lys Ala Gly Glu Ser Trp
 65                  70                  75                  80 atg cac ttt atc aag cac cta tac cag tta gtc ttg gag aac ggt atc     288
Met His Phe Ile Lys His Leu Tyr Gln Leu Val Leu Glu Asn Gly Ile
                 85                  90                  95 cca gaa aag tat gac tgg act att ttc tta aca ttt tgg gtg ttt cag     336
Pro Glu Lys Tyr Asp Trp Thr Ile Phe Leu Thr Phe Trp Val Phe Gln
            100                 105                 110 atc att ttc tac tat acg ttg ccc ggg att tgg aca aaa ggt caa cca     384
Ile Ile Phe Tyr Tyr Thr Leu Pro Gly Ile Trp Thr Lys Gly Gln Pro
        115                 120                 125
```

| | | |
|---|---|---|
| ttg tct cat ttg aag gga aaa caa ttg cct tac ttt tgt aat gcc atg<br>Leu Ser His Leu Lys Gly Lys Gln Leu Pro Tyr Phe Cys Asn Ala Met<br>130                       135                   140 | | 432 |
| tgg acc ttg tat gta act acc act ttg gtc ttg gtt ttg cac ttt acc<br>Trp Thr Leu Tyr Val Thr Thr Thr Leu Val Leu Val Leu His Phe Thr<br>145                     150                   155                   160 | | 480 |
| aat ctt ttt aga ttg tat gtc att att gac cgt ttt ggg agg atc atg<br>Asn Leu Phe Arg Leu Tyr Val Ile Ile Asp Arg Phe Gly Arg Ile Met<br>                 165                   170                   175 | | 528 |
| aca tgt gcc att att tca ggg ttt gcc ttc tcc atc ata ttg tac tta<br>Thr Cys Ala Ile Ile Ser Gly Phe Ala Phe Ser Ile Ile Leu Tyr Leu<br>                 180                   185                   190 | | 576 |
| tgg act tta ttt atc tca cat gac tat cat aga atg aca gga aac cat<br>Trp Thr Leu Phe Ile Ser His Asp Tyr His Arg Met Thr Gly Asn His<br>               195                   200                   205 | | 624 |
| cta tat gat ttc ttc atg gga gct cca cta aac cct agg tgg ggg att<br>Leu Tyr Asp Phe Phe Met Gly Ala Pro Leu Asn Pro Arg Trp Gly Ile<br>210                       215                   220 | | 672 |
| ttg gac ttg aag atg ttt ttc gag gtt aga tta cct tgg ttc acc ctt<br>Leu Asp Leu Lys Met Phe Phe Glu Val Arg Leu Pro Trp Phe Thr Leu<br>225                       230                   235                   240 | | 720 |
| tac ttt atc act ttg ggt gcc tgt ttg aag cag tgg gag act tac ggc<br>Tyr Phe Ile Thr Leu Gly Ala Cys Leu Lys Gln Trp Glu Thr Tyr Gly<br>                 245                   250                   255 | | 768 |
| tat gtg aca cca caa ttg ggg gtt gtc atg tta gct cat tgg ttg tac<br>Tyr Val Thr Pro Gln Leu Gly Val Val Met Leu Ala His Trp Leu Tyr<br>                 260                   265                   270 | | 816 |
| gcg aac gca tgt gct aaa ggt gaa gaa ttg att gtt cca acc tgg gac<br>Ala Asn Ala Cys Ala Lys Gly Glu Glu Leu Ile Val Pro Thr Trp Asp<br>                 275                   280                   285 | | 864 |
| atg gct tac gaa aag ttt gga ttt atg ctg atc ttc tgg aat att gcc<br>Met Ala Tyr Glu Lys Phe Gly Phe Met Leu Ile Phe Trp Asn Ile Ala<br>290                       295                   300 | | 912 |
| ggt gtc cca tac act tac tgt cat tgt acg ttg tat ttg tac tac cat<br>Gly Val Pro Tyr Thr Tyr Cys His Cys Thr Leu Tyr Leu Tyr Tyr His<br>305                       310                   315                   320 | | 960 |
| gac cca tct gaa tat cac tgg tct aca ctg tac aat gtt tcg ctg tac<br>Asp Pro Ser Glu Tyr His Trp Ser Thr Leu Tyr Asn Val Ser Leu Tyr<br>                 325                   330                   335 | | 1008 |
| gtt gtt cta tta tgc gcc tac tac ttc ttt gac acg gca aat gct cag<br>Val Val Leu Leu Cys Ala Tyr Tyr Phe Phe Asp Thr Ala Asn Ala Gln<br>                 340                   345                   350 | | 1056 |
| aaa aat gcc ttc aga aag caa atg tct ggt gac aag aca ggt agg aag<br>Lys Asn Ala Phe Arg Lys Gln Met Ser Gly Asp Lys Thr Gly Arg Lys<br>                 355                   360                   365 | | 1104 |
| act ttc cca ttt ttg cca tac caa att ttg aag aat cca aag tat atg<br>Thr Phe Pro Phe Leu Pro Tyr Gln Ile Leu Lys Asn Pro Lys Tyr Met<br>370                       375                   380 | | 1152 |
| gtt acc tcc aat gga tcg tac cta ttg att gat ggt tgg tac act ttg<br>Val Thr Ser Asn Gly Ser Tyr Leu Leu Ile Asp Gly Trp Tyr Thr Leu<br>385                       390                   395                   400 | | 1200 |
| gct aga aaa att cac tac act gcc gat tgg act caa tct ctc gtt tgg<br>Ala Arg Lys Ile His Tyr Thr Ala Asp Trp Thr Gln Ser Leu Val Trp<br>                 405                   410                   415 | | 1248 |
| gcc ttg tct tgc ggg ttc aac tcg gtg ttc cca tgg ttt ttc cca gta<br>Ala Leu Ser Cys Gly Phe Asn Ser Val Phe Pro Trp Phe Phe Pro Val<br>                 420                   425                   430 | | 1296 |
| ttc ttc ctt gtt gtc ctg att cac aga gcc ttc aga gac caa gca aaa<br>Phe Phe Leu Val Val Leu Ile His Arg Ala Phe Arg Asp Gln Ala Lys | | 1344 |

```
                      435                 440                 445
tgt aag aga aag tac gga aaa gat tgg gat gag tat tgt aaa cat tgc        1392
Cys Lys Arg Lys Tyr Gly Lys Asp Trp Asp Glu Tyr Cys Lys His Cys
    450                 455                 460 cct tac gtc ttt att cct tat gtt ttc tag                                1422
Pro Tyr Val Phe Ile Pro Tyr Val Phe
465                 470

<210> SEQ ID NO 18
<211> LENGTH: 473
<212> TYPE: PRT
<213> ORGANISM: Saccharomyces cerevisiae

<400> SEQUENCE: 18

Met Ala Lys Asp Asn Ser Glu Lys Leu Gln Val Gln Gly Glu Lys
 1               5                  10                  15

Lys Ser Lys Gln Pro Val Asn Phe Leu Pro Gln Gly Lys Trp Leu Lys
                20                  25                  30

Pro Asn Glu Ile Glu Tyr Glu Phe Gly Gly Thr Thr Gly Val Ile Gly
            35                  40                  45

Met Leu Ile Gly Phe Pro Leu Leu Met Tyr Tyr Met Trp Ile Cys Ala
         50                  55                  60

Glu Phe Tyr His Gly Lys Val Ala Leu Pro Lys Ala Gly Glu Ser Trp
65                  70                  75                  80

Met His Phe Ile Lys His Leu Tyr Gln Leu Val Leu Glu Asn Gly Ile
                85                  90                  95

Pro Glu Lys Tyr Asp Trp Thr Ile Phe Leu Thr Phe Trp Val Phe Gln
            100                 105                 110

Ile Ile Phe Tyr Tyr Thr Leu Pro Gly Ile Trp Thr Lys Gly Gln Pro
        115                 120                 125

Leu Ser His Leu Lys Gly Lys Gln Leu Pro Tyr Phe Cys Asn Ala Met
    130                 135                 140

Trp Thr Leu Tyr Val Thr Thr Thr Leu Val Leu Val Leu His Phe Thr
145                 150                 155                 160

Asn Leu Phe Arg Leu Tyr Val Ile Ile Asp Arg Phe Gly Arg Ile Met
                165                 170                 175

Thr Cys Ala Ile Ile Ser Gly Phe Ala Phe Ser Ile Ile Leu Tyr Leu
            180                 185                 190

Trp Thr Leu Phe Ile Ser His Asp Tyr His Arg Met Thr Gly Asn His
        195                 200                 205

Leu Tyr Asp Phe Phe Met Gly Ala Pro Leu Asn Pro Arg Trp Gly Ile
    210                 215                 220

Leu Asp Leu Lys Met Phe Phe Glu Val Arg Leu Pro Trp Phe Thr Leu
225                 230                 235                 240

Tyr Phe Ile Thr Leu Gly Ala Cys Leu Lys Gln Trp Glu Thr Tyr Gly
                245                 250                 255

Tyr Val Thr Pro Gln Leu Gly Val Val Met Leu Ala His Trp Leu Tyr
            260                 265                 270

Ala Asn Ala Cys Ala Lys Gly Glu Glu Leu Ile Val Pro Thr Trp Asp
        275                 280                 285

Met Ala Tyr Glu Lys Phe Gly Phe Met Leu Ile Phe Trp Asn Ile Ala
    290                 295                 300

Gly Val Pro Tyr Thr Tyr Cys His Cys Thr Leu Tyr Leu Tyr His
305                 310                 315                 320

Asp Pro Ser Glu Tyr His Trp Ser Thr Leu Tyr Asn Val Ser Leu Tyr
```

-continued

```
                    325                 330                 335
Val Val Leu Leu Cys Ala Tyr Tyr Phe Phe Asp Thr Ala Asn Ala Gln
                340                 345                 350
Lys Asn Ala Phe Arg Lys Gln Met Ser Gly Asp Lys Thr Gly Arg Lys
                355                 360                 365
Thr Phe Pro Phe Leu Pro Tyr Gln Ile Leu Lys Asn Pro Lys Tyr Met
            370                 375                 380
Val Thr Ser Asn Gly Ser Tyr Leu Leu Ile Asp Gly Trp Tyr Thr Leu
385                 390                 395                 400
Ala Arg Lys Ile His Tyr Thr Ala Asp Trp Thr Gln Ser Leu Val Trp
                405                 410                 415
Ala Leu Ser Cys Gly Phe Asn Ser Val Phe Pro Trp Phe Phe Pro Val
                420                 425                 430
Phe Phe Leu Val Val Leu Ile His Arg Ala Phe Arg Asp Gln Ala Lys
                435                 440                 445
Cys Lys Arg Lys Tyr Gly Lys Asp Trp Asp Glu Tyr Cys Lys His Cys
            450                 455                 460
Pro Tyr Val Phe Ile Pro Tyr Val Phe
465                 470
```

<210> SEQ ID NO 19
<211> LENGTH: 1152
<212> TYPE: DNA
<213> ORGANISM: Saccharomyces cerevisiae
<220> FEATURE:
<221> NAME/KEY: CDS
<222> LOCATION: (1)..(1152)

<400> SEQUENCE: 19

```
atg agt gaa aca gaa ttg aga aaa aga cag gcc caa ttc act agg gag      48
Met Ser Glu Thr Glu Leu Arg Lys Arg Gln Ala Gln Phe Thr Arg Glu
1               5                   10                  15 tta cat ggt gat gat att ggt aaa aag aca ggt ttg agt gca ttg atg      96
Leu His Gly Asp Asp Ile Gly Lys Lys Thr Gly Leu Ser Ala Leu Met
                20                  25                  30 tcg aag aac aac tct gcc caa aag gaa gcc gtt cag aag tac ttg aga     144
Ser Lys Asn Asn Ser Ala Gln Lys Glu Ala Val Gln Lys Tyr Leu Arg
            35                  40                  45 aat tgg gat ggt aga acc gat aaa gat gcc gaa gaa cgt cgt ctt gag     192
Asn Trp Asp Gly Arg Thr Asp Lys Asp Ala Glu Glu Arg Arg Leu Glu
        50                  55                  60 gat tat aat gaa gcc aca cat tcc tac tat aac gtc gtt aca gat ttc     240
Asp Tyr Asn Glu Ala Thr His Ser Tyr Tyr Asn Val Val Thr Asp Phe
65                  70                  75                  80 tat gaa tat ggt tgg ggt tcc tct ttc cat ttc agc aga ttt tat aaa     288
Tyr Glu Tyr Gly Trp Gly Ser Ser Phe His Phe Ser Arg Phe Tyr Lys
                85                  90                  95 ggt gag agt ttc gct gcc tcg ata gca aga cat gaa cat tat tta gct     336
Gly Glu Ser Phe Ala Ala Ser Ile Ala Arg His Glu His Tyr Leu Ala
                100                 105                 110 tac aag gct ggt att caa aga ggc gat tta gtt ctc gac gtt ggt tgt     384
Tyr Lys Ala Gly Ile Gln Arg Gly Asp Leu Val Leu Asp Val Gly Cys
            115                 120                 125 ggt gtt ggg ggc cca gca aga gag att gca aga ttt acc ggt tgt aac     432
Gly Val Gly Gly Pro Ala Arg Glu Ile Ala Arg Phe Thr Gly Cys Asn
        130                 135                 140 gtc atc ggt cta aac aat aac gat tac caa att gcc aag gca aaa tat     480
Val Ile Gly Leu Asn Asn Asn Asp Tyr Gln Ile Ala Lys Ala Lys Tyr
145                 150                 155                 160
```

```
tac gct aaa aaa tac aat ttg agt gac caa atg gac ttt gta aag ggt    528
Tyr Ala Lys Lys Tyr Asn Leu Ser Asp Gln Met Asp Phe Val Lys Gly
            165                 170                 175 gat ttc atg aaa atg gat ttc gaa gaa aac act ttc gac aaa gtt tat    576
Asp Phe Met Lys Met Asp Phe Glu Glu Asn Thr Phe Asp Lys Val Tyr
        180                 185                 190 gca att gag gcc aca tgt cac gct cca aaa tta gaa ggt gta tac agc    624
Ala Ile Glu Ala Thr Cys His Ala Pro Lys Leu Glu Gly Val Tyr Ser
    195                 200                 205 gaa atc tac aag gtt ttg aaa ccg ggt ggt acc ttt gct gtt tac gaa    672
Glu Ile Tyr Lys Val Leu Lys Pro Gly Gly Thr Phe Ala Val Tyr Glu
210                 215                 220 tgg gta atg act gat aaa tat gac gaa aac aat cct gaa cat aga aag    720
Trp Val Met Thr Asp Lys Tyr Asp Glu Asn Asn Pro Glu His Arg Lys
225                 230                 235                 240 atc gct tat gaa att gaa cta ggt gat ggt atc cca aag atg ttc cat    768
Ile Ala Tyr Glu Ile Glu Leu Gly Asp Gly Ile Pro Lys Met Phe His
                245                 250                 255 gtc gac gtg gct agg aaa gca ttg aag aac tgt ggt ttc gaa gtc ctc    816
Val Asp Val Ala Arg Lys Ala Leu Lys Asn Cys Gly Phe Glu Val Leu
            260                 265                 270 gtt agc gaa gac ctg gcg gac aat gat gat gaa atc cct tgg tat tac    864
Val Ser Glu Asp Leu Ala Asp Asn Asp Asp Glu Ile Pro Trp Tyr Tyr
        275                 280                 285 cca tta act ggt gag tgg aag tac gtt caa aac tta gct aat ttg gcc    912
Pro Leu Thr Gly Glu Trp Lys Tyr Val Gln Asn Leu Ala Asn Leu Ala
    290                 295                 300 aca ttt ttc aga act tct tac ttg ggt aga caa ttt act aca gca atg    960
Thr Phe Phe Arg Thr Ser Tyr Leu Gly Arg Gln Phe Thr Thr Ala Met
305                 310                 315                 320 gtt act gta atg gaa aaa tta ggt cta gcc cca gaa ggt tcc aag gaa   1008
Val Thr Val Met Glu Lys Leu Gly Leu Ala Pro Glu Gly Ser Lys Glu
                325                 330                 335 gtt act gct gct cta gaa aat gct gcg gtt ggt tta gtt gcc ggt ggt   1056
Val Thr Ala Ala Leu Glu Asn Ala Ala Val Gly Leu Val Ala Gly Gly
            340                 345                 350 aag tcc aag tta ttc act cca atg atg ctt ttc gtc gct agg aag cca   1104
Lys Ser Lys Leu Phe Thr Pro Met Met Leu Phe Val Ala Arg Lys Pro
        355                 360                 365 gaa aac gcc gaa acc ccc tcc caa act tcc caa gaa gca act caa taa   1152
Glu Asn Ala Glu Thr Pro Ser Gln Thr Ser Gln Glu Ala Thr Gln
    370                 375                 380

<210> SEQ ID NO 20
<211> LENGTH: 383
<212> TYPE: PRT
<213> ORGANISM: Saccharomyces cerevisiae

<400> SEQUENCE: 20

Met Ser Glu Thr Glu Leu Arg Lys Arg Gln Ala Gln Phe Thr Arg Glu
1               5                   10                  15

Leu His Gly Asp Asp Ile Gly Lys Lys Thr Gly Leu Ser Ala Leu Met
                20                  25                  30

Ser Lys Asn Asn Ser Ala Gln Lys Glu Ala Val Gln Lys Tyr Leu Arg
            35                  40                  45

Asn Trp Asp Gly Arg Thr Asp Lys Asp Ala Glu Glu Arg Arg Leu Glu
        50                  55                  60

Asp Tyr Asn Glu Ala Thr His Ser Tyr Tyr Asn Val Val Thr Asp Phe
65                  70                  75                  80
```

-continued

Tyr Glu Tyr Gly Trp Gly Ser Ser Phe His Phe Ser Arg Phe Tyr Lys
                85                  90                  95

Gly Glu Ser Phe Ala Ala Ser Ile Ala Arg His Glu His Tyr Leu Ala
            100                 105                 110

Tyr Lys Ala Gly Ile Gln Arg Gly Asp Leu Val Leu Asp Val Gly Cys
        115                 120                 125

Gly Val Gly Gly Pro Ala Arg Glu Ile Ala Arg Phe Thr Gly Cys Asn
    130                 135                 140

Val Ile Gly Leu Asn Asn Asn Asp Tyr Gln Ile Ala Lys Ala Lys Tyr
145                 150                 155                 160

Tyr Ala Lys Lys Tyr Asn Leu Ser Asp Gln Met Asp Phe Val Lys Gly
            165                 170                 175

Asp Phe Met Lys Met Asp Phe Glu Glu Asn Thr Phe Asp Lys Val Tyr
        180                 185                 190

Ala Ile Glu Ala Thr Cys His Ala Pro Lys Leu Glu Gly Val Tyr Ser
    195                 200                 205

Glu Ile Tyr Lys Val Leu Lys Pro Gly Gly Thr Phe Ala Val Tyr Glu
    210                 215                 220

Trp Val Met Thr Asp Lys Tyr Asp Glu Asn Asn Pro Glu His Arg Lys
225                 230                 235                 240

Ile Ala Tyr Glu Ile Glu Leu Gly Asp Gly Ile Pro Lys Met Phe His
            245                 250                 255

Val Asp Val Ala Arg Lys Ala Leu Lys Asn Cys Gly Phe Glu Val Leu
        260                 265                 270

Val Ser Glu Asp Leu Ala Asp Asn Asp Asp Glu Ile Pro Trp Tyr Tyr
    275                 280                 285

Pro Leu Thr Gly Glu Trp Lys Tyr Val Gln Asn Leu Ala Asn Leu Ala
    290                 295                 300

Thr Phe Phe Arg Thr Ser Tyr Leu Gly Arg Gln Phe Thr Thr Ala Met
305                 310                 315                 320

Val Thr Val Met Glu Lys Leu Gly Leu Ala Pro Glu Gly Ser Lys Glu
            325                 330                 335

Val Thr Ala Ala Leu Glu Asn Ala Ala Val Gly Leu Val Ala Gly Gly
        340                 345                 350

Lys Ser Lys Leu Phe Thr Pro Met Met Leu Phe Val Ala Arg Lys Pro
    355                 360                 365

Glu Asn Ala Glu Thr Pro Ser Gln Thr Ser Gln Glu Ala Thr Gln
    370                 375                 380

<210> SEQ ID NO 21
<211> LENGTH: 1617
<212> TYPE: DNA
<213> ORGANISM: Saccharomyces cerevisiae
<220> FEATURE:
<221> NAME/KEY: CDS
<222> LOCATION: (1)..(1617)

<400> SEQUENCE: 21 atg agt tct gtc gca gaa aat ata ata caa cat gcc act cat aat tct         48
Met Ser Ser Val Ala Glu Asn Ile Ile Gln His Ala Thr His Asn Ser
 1               5                  10                  15 acg cta cac caa ttg gct aaa gac cag ccc tct gta ggc gtc act act         96
Thr Leu His Gln Leu Ala Lys Asp Gln Pro Ser Val Gly Val Thr Thr
            20                  25                  30 gcc ttc agt atc ctg gat aca ctt aag tct atg tca tat ttg aaa ata        144
Ala Phe Ser Ile Leu Asp Thr Leu Lys Ser Met Ser Tyr Leu Lys Ile
        35                  40                  45

```
                  35                  40                    45
ttt gct act tta atc tgt att ctt ttg gtt tgg gac caa gtt gca tat    192
Phe Ala Thr Leu Ile Cys Ile Leu Leu Val Trp Asp Gln Val Ala Tyr
         50                  55                  60 caa atc aag aaa ggt tcc atc gca ggt cca aag ttt aag ttc tgg ccc    240
Gln Ile Lys Lys Gly Ser Ile Ala Gly Pro Lys Phe Lys Phe Trp Pro
65                  70                  75                  80 atc atc ggt cca ttt ttg gaa tcc tta gat cca aag ttt gaa gaa tat    288
Ile Ile Gly Pro Phe Leu Glu Ser Leu Asp Pro Lys Phe Glu Glu Tyr
                 85                  90                  95 aag gct aag tgg gca tcc ggt cca ctt tca tgt gtt tct att ttc cat    336
Lys Ala Lys Trp Ala Ser Gly Pro Leu Ser Cys Val Ser Ile Phe His
            100                 105                 110 aaa ttt gtt gtt atc gca tct act aga gac ttg gca aga aag atc ttg    384
Lys Phe Val Val Ile Ala Ser Thr Arg Asp Leu Ala Arg Lys Ile Leu
        115                 120                 125 caa tct tcc aaa ttc gtc aaa cct tgc gtt gtc gat gtt gct gtg aag    432
Gln Ser Ser Lys Phe Val Lys Pro Cys Val Val Asp Val Ala Val Lys
    130                 135                 140 atc tta aga cct tgc aat tgg gtt ttt ttg gac ggt aaa gct cat act    480
Ile Leu Arg Pro Cys Asn Trp Val Phe Leu Asp Gly Lys Ala His Thr
145                 150                 155                 160 gat tac aga aaa tca tta aac ggt ctt ttc act aaa caa gct ttg gct    528
Asp Tyr Arg Lys Ser Leu Asn Gly Leu Phe Thr Lys Gln Ala Leu Ala
                165                 170                 175 caa tac tta cct tca ttg gaa caa atc atg gat aag tac atg gat aag    576
Gln Tyr Leu Pro Ser Leu Glu Gln Ile Met Asp Lys Tyr Met Asp Lys
            180                 185                 190 ttt gtt cgt tta tct aag gag aat aac tac gag ccc cag gtc ttt ttc    624
Phe Val Arg Leu Ser Lys Glu Asn Asn Tyr Glu Pro Gln Val Phe Phe
        195                 200                 205 cat gaa atg aga gaa att ctt tgc gcc tta tca ttg aac tct ttc tgt    672
His Glu Met Arg Glu Ile Leu Cys Ala Leu Ser Leu Asn Ser Phe Cys
    210                 215                 220 ggt aac tat att acc gaa gat caa gtc aga aag att gct gat gat tac    720
Gly Asn Tyr Ile Thr Glu Asp Gln Val Arg Lys Ile Ala Asp Asp Tyr
225                 230                 235                 240 tat ttg gtt aca gca gca ttg gaa tta gtc aac ttc cca att att atc    768
Tyr Leu Val Thr Ala Ala Leu Glu Leu Val Asn Phe Pro Ile Ile Ile
                245                 250                 255 cct tac act aaa aca tgg tat ggt aag aaa act gca gac atg gcc atg    816
Pro Tyr Thr Lys Thr Trp Tyr Gly Lys Lys Thr Ala Asp Met Ala Met
            260                 265                 270 aag att ttc gaa aac tgt gct caa atg gct aag gat cat att gct gca    864
Lys Ile Phe Glu Asn Cys Ala Gln Met Ala Lys Asp His Ile Ala Ala
        275                 280                 285 ggt ggt aag cca gtt tgt gtt atg gat gct tgg tgt aag ttg atg cac    912
Gly Gly Lys Pro Val Cys Val Met Asp Ala Trp Cys Lys Leu Met His
    290                 295                 300 gat gca aag aat agt aac gat gat gat tct aga atc tac cac aga gag    960
Asp Ala Lys Asn Ser Asn Asp Asp Asp Ser Arg Ile Tyr His Arg Glu
305                 310                 315                 320 ttt act aac aag gaa atc tcc gaa gct gtt ttc act ttc tta ttt gct   1008
Phe Thr Asn Lys Glu Ile Ser Glu Ala Val Phe Thr Phe Leu Phe Ala
                325                 330                 335 tct caa gat gcc tct tct tct tta gct tgt tgg ttg ttc caa att gtt   1056
Ser Gln Asp Ala Ser Ser Ser Leu Ala Cys Trp Leu Phe Gln Ile Val
            340                 345                 350 gct gac cgt cca gat gtc tta gct aag atc aga gaa gaa caa ttg gct   1104
```

```
            Ala Asp Arg Pro Asp Val Leu Ala Lys Ile Arg Glu Glu Gln Leu Ala
                355                 360                 365 gtt cgt aac aat gac atg tct acc gaa ttg aac ttg gat ttg att gag        1152
Val Arg Asn Asn Asp Met Ser Thr Glu Leu Asn Leu Asp Leu Ile Glu
    370                 375                 380 aaa atg aag tac acc aat atg gtc ata aaa gaa act ttg cgt tac aga        1200
Lys Met Lys Tyr Thr Asn Met Val Ile Lys Glu Thr Leu Arg Tyr Arg
385                 390                 395                 400 cct cct gtc ttg atg gtt cca tat gtt gtt aag aag aat ttc cca gtt        1248
Pro Pro Val Leu Met Val Pro Tyr Val Val Lys Lys Asn Phe Pro Val
                405                 410                 415 tcc cct aac tat acc gca cca aag ggc gct atg tta att cca acc tta        1296
Ser Pro Asn Tyr Thr Ala Pro Lys Gly Ala Met Leu Ile Pro Thr Leu
                420                 425                 430 tac cca gct tta cat gat cct gaa gtt tac gaa aat cct gat gag ttc        1344
Tyr Pro Ala Leu His Asp Pro Glu Val Tyr Glu Asn Pro Asp Glu Phe
                435                 440                 445 atc cct gaa aga tgg gta gaa ggc tct aag gct agt gaa gca aag aag        1392
Ile Pro Glu Arg Trp Val Glu Gly Ser Lys Ala Ser Glu Ala Lys Lys
            450                 455                 460 aat tgg ttg gtt ttt ggt tgt ggt cca cac gtt tgc tta ggt caa aca        1440
Asn Trp Leu Val Phe Gly Cys Gly Pro His Val Cys Leu Gly Gln Thr
465                 470                 475                 480 tat gtc atg att acc ttc gcc gct ttg ttg ggt aaa ttt gca cta tat        1488
Tyr Val Met Ile Thr Phe Ala Ala Leu Leu Gly Lys Phe Ala Leu Tyr
                485                 490                 495 act gat ttc cat cat aca gtg act cca tta agt gaa aaa atc aag gtt        1536
Thr Asp Phe His His Thr Val Thr Pro Leu Ser Glu Lys Ile Lys Val
                500                 505                 510 ttc gct aca att ttc cca aaa gat gat ttg tta ctg act ttc aaa aag        1584
Phe Ala Thr Ile Phe Pro Lys Asp Asp Leu Leu Leu Thr Phe Lys Lys
                515                 520                 525 aga gac cca att act gga gaa gtc ttc gaa taa                            1617
Arg Asp Pro Ile Thr Gly Glu Val Phe Glu
                530                 535

<210> SEQ ID NO 22
<211> LENGTH: 538
<212> TYPE: PRT
<213> ORGANISM: Saccharomyces cerevisiae

<400> SEQUENCE: 22

Met Ser Ser Val Ala Glu Asn Ile Ile Gln His Ala Thr His Asn Ser
1               5                   10                  15

Thr Leu His Gln Leu Ala Lys Asp Gln Pro Ser Val Gly Val Thr Thr
                20                  25                  30

Ala Phe Ser Ile Leu Asp Thr Leu Lys Ser Met Ser Tyr Leu Lys Ile
            35                  40                  45

Phe Ala Thr Leu Ile Cys Ile Leu Leu Val Trp Asp Gln Val Ala Tyr
        50                  55                  60

Gln Ile Lys Lys Gly Ser Ile Ala Gly Pro Lys Phe Lys Phe Trp Pro
65              70                  75                  80

Ile Ile Gly Pro Phe Leu Glu Ser Leu Asp Pro Lys Phe Glu Glu Tyr
                85                  90                  95

Lys Ala Lys Trp Ala Ser Gly Pro Leu Ser Cys Val Ser Ile Phe His
                100                 105                 110

Lys Phe Val Val Ile Ala Ser Thr Arg Asp Leu Ala Arg Lys Ile Leu
            115                 120                 125
```

-continued

```
Gln Ser Ser Lys Phe Val Lys Pro Cys Val Val Asp Val Ala Val Lys
    130                 135                 140

Ile Leu Arg Pro Cys Asn Trp Val Phe Leu Asp Gly Lys Ala His Thr
145                 150                 155                 160

Asp Tyr Arg Lys Ser Leu Asn Gly Leu Phe Thr Lys Gln Ala Leu Ala
                165                 170                 175

Gln Tyr Leu Pro Ser Leu Glu Gln Ile Met Asp Lys Tyr Met Asp Lys
            180                 185                 190

Phe Val Arg Leu Ser Lys Glu Asn Asn Tyr Glu Pro Gln Val Phe Phe
        195                 200                 205

His Glu Met Arg Glu Ile Leu Cys Ala Leu Ser Leu Asn Ser Phe Cys
    210                 215                 220

Gly Asn Tyr Ile Thr Glu Asp Gln Val Arg Lys Ile Ala Asp Asp Tyr
225                 230                 235                 240

Tyr Leu Val Thr Ala Ala Leu Glu Leu Val Asn Phe Pro Ile Ile Ile
                245                 250                 255

Pro Tyr Thr Lys Thr Trp Tyr Gly Lys Lys Thr Ala Asp Met Ala Met
            260                 265                 270

Lys Ile Phe Glu Asn Cys Ala Gln Met Ala Lys Asp His Ile Ala Ala
        275                 280                 285

Gly Gly Lys Pro Val Cys Val Met Asp Ala Trp Cys Lys Leu Met His
    290                 295                 300

Asp Ala Lys Asn Ser Asn Asp Asp Ser Arg Ile Tyr His Arg Glu
305                 310                 315                 320

Phe Thr Asn Lys Glu Ile Ser Glu Ala Val Phe Thr Phe Leu Phe Ala
                325                 330                 335

Ser Gln Asp Ala Ser Ser Ser Leu Ala Cys Trp Leu Phe Gln Ile Val
            340                 345                 350

Ala Asp Arg Pro Asp Val Leu Ala Lys Ile Arg Glu Glu Gln Leu Ala
        355                 360                 365

Val Arg Asn Asn Asp Met Ser Thr Glu Leu Asn Leu Asp Leu Ile Glu
    370                 375                 380

Lys Met Lys Tyr Thr Asn Met Val Ile Lys Glu Thr Leu Arg Tyr Arg
385                 390                 395                 400

Pro Pro Val Leu Met Val Pro Tyr Val Val Lys Lys Asn Phe Pro Val
                405                 410                 415

Ser Pro Asn Tyr Thr Ala Pro Lys Gly Ala Met Leu Ile Pro Thr Leu
            420                 425                 430

Tyr Pro Ala Leu His Asp Pro Glu Val Tyr Glu Asn Pro Asp Glu Phe
        435                 440                 445

Ile Pro Glu Arg Trp Val Glu Gly Ser Lys Ala Ser Glu Ala Lys Lys
    450                 455                 460

Asn Trp Leu Val Phe Gly Cys Gly Pro His Val Cys Leu Gly Gln Thr
465                 470                 475                 480

Tyr Val Met Ile Thr Phe Ala Ala Leu Leu Gly Lys Phe Ala Leu Tyr
                485                 490                 495

Thr Asp Phe His His Thr Val Thr Pro Leu Ser Glu Lys Ile Lys Val
            500                 505                 510

Phe Ala Thr Ile Phe Pro Lys Asp Asp Leu Leu Leu Thr Phe Lys Lys
        515                 520                 525

Arg Asp Pro Ile Thr Gly Glu Val Phe Glu
    530                 535
```

<210> SEQ ID NO 23
<211> LENGTH: 1578
<212> TYPE: DNA
<213> ORGANISM: Artificial Sequence
<220> FEATURE:
<223> OTHER INFORMATION: Description of Artificial Sequence: Truncated HMG construct
<220> FEATURE:
<221> NAME/KEY: CDS
<222> LOCATION: (1)..(1578)

<400> SEQUENCE: 23

```
atg gac caa ttg gtg aaa act gaa gtc acc aag aag tct ttt act gct      48
Met Asp Gln Leu Val Lys Thr Glu Val Thr Lys Lys Ser Phe Thr Ala
1               5                   10                  15 cct gta caa aag gct tct aca cca gtt tta acc aat aaa aca gtc att      96
Pro Val Gln Lys Ala Ser Thr Pro Val Leu Thr Asn Lys Thr Val Ile
            20                  25                  30 tct gga tcg aaa gtc aaa agt tta tca tct gcg caa tcg agc tca tca     144
Ser Gly Ser Lys Val Lys Ser Leu Ser Ser Ala Gln Ser Ser Ser Ser
        35                  40                  45 gga cct tca tca tct agt gag gaa gat gat tcc cgc gat att gaa agc     192
Gly Pro Ser Ser Ser Ser Glu Glu Asp Asp Ser Arg Asp Ile Glu Ser
    50                  55                  60 ttg gat aag aaa ata cgt cct tta gaa gaa tta gaa gca tta tta agt     240
Leu Asp Lys Lys Ile Arg Pro Leu Glu Glu Leu Glu Ala Leu Leu Ser
65                  70                  75                  80 agt gga aat aca aaa caa ttg aag aac aaa gag gtc gct gcc ttg gtt     288
Ser Gly Asn Thr Lys Gln Leu Lys Asn Lys Glu Val Ala Ala Leu Val
                85                  90                  95 att cac ggt aag tta cct ttg tac gct ttg gag aaa aaa tta ggt gat     336
Ile His Gly Lys Leu Pro Leu Tyr Ala Leu Glu Lys Lys Leu Gly Asp
            100                 105                 110 act acg aga gcg gtt gcg gta cgt agg aag gct ctt tca att ttg gca     384
Thr Thr Arg Ala Val Ala Val Arg Arg Lys Ala Leu Ser Ile Leu Ala
        115                 120                 125 gaa gct cct gta tta gca tct gat cgt tta cca tat aaa aat tat gac     432
Glu Ala Pro Val Leu Ala Ser Asp Arg Leu Pro Tyr Lys Asn Tyr Asp
    130                 135                 140 tac gac cgc gta ttt ggc gct tgt tgt gaa aat gtt ata ggt tac atg     480
Tyr Asp Arg Val Phe Gly Ala Cys Cys Glu Asn Val Ile Gly Tyr Met
145                 150                 155                 160 cct ttg ccc gtt ggt gtt ata ggc ccc ttg gtt atc gat ggt aca tct     528
Pro Leu Pro Val Gly Val Ile Gly Pro Leu Val Ile Asp Gly Thr Ser
                165                 170                 175 tat cat ata cca atg gca act aca gag ggt tgt ttg gta gct tct gcc     576
Tyr His Ile Pro Met Ala Thr Thr Glu Gly Cys Leu Val Ala Ser Ala
            180                 185                 190 atg cgt ggc tgt aag gca atc aat gct ggc ggt ggt gca aca act gtt     624
Met Arg Gly Cys Lys Ala Ile Asn Ala Gly Gly Gly Ala Thr Thr Val
        195                 200                 205 tta act aag gat ggt atg aca aga ggc cca gta gtc cgt ttc cca act     672
Leu Thr Lys Asp Gly Met Thr Arg Gly Pro Val Val Arg Phe Pro Thr
    210                 215                 220 ttg aaa aga tct ggt gcc tgt aag ata tgg tta gac tca gaa gag gga     720
Leu Lys Arg Ser Gly Ala Cys Lys Ile Trp Leu Asp Ser Glu Glu Gly
225                 230                 235                 240 caa aac gca att aaa aaa gct ttt aac tct aca tca aga ttt gca cgt     768
Gln Asn Ala Ile Lys Lys Ala Phe Asn Ser Thr Ser Arg Phe Ala Arg
                245                 250                 255 ctg caa cat att caa act tgt cta gca gga gat tta ctc ttc atg aga     816
Leu Gln His Ile Gln Thr Cys Leu Ala Gly Asp Leu Leu Phe Met Arg
```

```
                260                 265                 270
ttt aga aca act act ggt gac gca atg ggt atg aat atg att tct aaa      864
Phe Arg Thr Thr Thr Gly Asp Ala Met Gly Met Asn Met Ile Ser Lys
        275                 280                 285 ggt gtc gaa tac tca tta aag caa atg gta gaa gag tat ggc tgg gaa      912
Gly Val Glu Tyr Ser Leu Lys Gln Met Val Glu Glu Tyr Gly Trp Glu
    290                 295                 300 gat atg gag gtt gtc tcc gtt tct ggt aac tac tgt acc gac aaa aaa      960
Asp Met Glu Val Val Ser Val Ser Gly Asn Tyr Cys Thr Asp Lys Lys
305                 310                 315                 320 cca gct gcc atc aac tgg atc gaa ggt cgt ggt aag agt gtc gtc gca     1008
Pro Ala Ala Ile Asn Trp Ile Glu Gly Arg Gly Lys Ser Val Val Ala
                325                 330                 335 gaa gct act att cct ggt gat gtt gtc aga aaa gtg tta aaa agt gat     1056
Glu Ala Thr Ile Pro Gly Asp Val Val Arg Lys Val Leu Lys Ser Asp
            340                 345                 350 gtt tcc gca ttg gtt gag ttg aac att gct aag aat ttg gtt gga tct     1104
Val Ser Ala Leu Val Glu Leu Asn Ile Ala Lys Asn Leu Val Gly Ser
        355                 360                 365 gca atg gct ggg tct gtt ggt gga ttt aac gca cat gca gct aat tta     1152
Ala Met Ala Gly Ser Val Gly Gly Phe Asn Ala His Ala Ala Asn Leu
    370                 375                 380 gtg aca gct gtt ttc ttg gca tta gga caa gat cct gca caa aat gtt     1200
Val Thr Ala Val Phe Leu Ala Leu Gly Gln Asp Pro Ala Gln Asn Val
385                 390                 395                 400 gaa agt tcc aac tgt ata aca ttg atg aaa gaa gtg gac ggt gat ttg     1248
Glu Ser Ser Asn Cys Ile Thr Leu Met Lys Glu Val Asp Gly Asp Leu
                405                 410                 415 aga att tcc gta tcc atg cca tcc atc gaa gta ggt acc atc ggt ggt     1296
Arg Ile Ser Val Ser Met Pro Ser Ile Glu Val Gly Thr Ile Gly Gly
            420                 425                 430 ggt act gtt cta gaa cca caa ggt gcc atg ttg gac tta tta ggt gta     1344
Gly Thr Val Leu Glu Pro Gln Gly Ala Met Leu Asp Leu Leu Gly Val
        435                 440                 445 aga ggc ccg cat gct acc gct cct ggt acc aac gca cgt caa tta gca     1392
Arg Gly Pro His Ala Thr Ala Pro Gly Thr Asn Ala Arg Gln Leu Ala
    450                 455                 460 aga ata gtt gcc tgt gcc gtc ttg gca ggt gaa tta tcc tta tgt gct     1440
Arg Ile Val Ala Cys Ala Val Leu Ala Gly Glu Leu Ser Leu Cys Ala
465                 470                 475                 480 gcc cta gca gcc ggc cat ttg gtt caa agt cat atg acc cac aac agg     1488
Ala Leu Ala Ala Gly His Leu Val Gln Ser His Met Thr His Asn Arg
                485                 490                 495 aaa cct gct gaa cca aca aaa cct aac aat ttg gac gcc act gat ata     1536
Lys Pro Ala Glu Pro Thr Lys Pro Asn Asn Leu Asp Ala Thr Asp Ile
            500                 505                 510 aat cgt ttg aaa gat ggg tcc gtc acc tgc att aaa tcc taa             1578
Asn Arg Leu Lys Asp Gly Ser Val Thr Cys Ile Lys Ser
        515                 520                 525

<210> SEQ ID NO 24
<211> LENGTH: 525
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 24

Met Asp Gln Leu Val Lys Thr Glu Val Thr Lys Lys Ser Phe Thr Ala
1               5                   10                  15
```

-continued

```
Pro Val Gln Lys Ala Ser Thr Pro Val Leu Thr Asn Lys Thr Val Ile
             20                  25                  30

Ser Gly Ser Lys Val Lys Ser Leu Ser Ser Ala Gln Ser Ser Ser Ser
         35                  40                  45

Gly Pro Ser Ser Ser Ser Glu Glu Asp Asp Ser Arg Asp Ile Glu Ser
         50                  55                  60

Leu Asp Lys Lys Ile Arg Pro Leu Glu Glu Leu Glu Ala Leu Leu Ser
 65                  70                  75                  80

Ser Gly Asn Thr Lys Gln Leu Lys Asn Lys Glu Val Ala Ala Leu Val
             85                  90                  95

Ile His Gly Lys Leu Pro Leu Tyr Ala Leu Glu Lys Lys Leu Gly Asp
             100                 105                 110

Thr Thr Arg Ala Val Ala Val Arg Lys Ala Leu Ser Ile Leu Ala
             115                 120                 125

Glu Ala Pro Val Leu Ala Ser Asp Arg Leu Pro Tyr Lys Asn Tyr Asp
             130                 135                 140

Tyr Asp Arg Val Phe Gly Ala Cys Cys Glu Asn Val Ile Gly Tyr Met
145                 150                 155                 160

Pro Leu Pro Val Gly Val Ile Gly Pro Leu Val Ile Asp Gly Thr Ser
             165                 170                 175

Tyr His Ile Pro Met Ala Thr Thr Glu Gly Cys Leu Val Ala Ser Ala
             180                 185                 190

Met Arg Gly Cys Lys Ala Ile Asn Ala Gly Gly Gly Ala Thr Thr Val
             195                 200                 205

Leu Thr Lys Asp Gly Met Thr Arg Gly Pro Val Val Arg Phe Pro Thr
             210                 215                 220

Leu Lys Arg Ser Gly Ala Cys Lys Ile Trp Leu Asp Ser Glu Glu Gly
225                 230                 235                 240

Gln Asn Ala Ile Lys Lys Ala Phe Asn Ser Thr Ser Arg Phe Ala Arg
             245                 250                 255

Leu Gln His Ile Gln Thr Cys Leu Ala Gly Asp Leu Leu Phe Met Arg
             260                 265                 270

Phe Arg Thr Thr Thr Gly Asp Ala Met Gly Met Asn Met Ile Ser Lys
             275                 280                 285

Gly Val Glu Tyr Ser Leu Lys Gln Met Val Glu Glu Tyr Gly Trp Glu
             290                 295                 300

Asp Met Glu Val Val Ser Val Ser Gly Asn Tyr Cys Thr Asp Lys Lys
305                 310                 315                 320

Pro Ala Ala Ile Asn Trp Ile Glu Gly Arg Gly Lys Ser Val Val Ala
             325                 330                 335

Glu Ala Thr Ile Pro Gly Asp Val Val Arg Lys Val Leu Lys Ser Asp
             340                 345                 350

Val Ser Ala Leu Val Glu Leu Asn Ile Ala Lys Asn Leu Val Gly Ser
             355                 360                 365

Ala Met Ala Gly Ser Val Gly Gly Phe Asn Ala His Ala Ala Asn Leu
             370                 375                 380

Val Thr Ala Val Phe Leu Ala Leu Gly Gln Asp Pro Ala Gln Asn Val
385                 390                 395                 400

Glu Ser Ser Asn Cys Ile Thr Leu Met Lys Glu Val Asp Gly Asp Leu
             405                 410                 415

Arg Ile Ser Val Ser Met Pro Ser Ile Glu Val Gly Thr Ile Gly Gly
             420                 425                 430
```

```
Gly Thr Val Leu Glu Pro Gln Gly Ala Met Leu Asp Leu Leu Gly Val
            435                 440                 445

Arg Gly Pro His Ala Thr Ala Pro Gly Thr Asn Ala Arg Gln Leu Ala
    450                 455                 460

Arg Ile Val Ala Cys Ala Val Leu Ala Gly Glu Leu Ser Leu Cys Ala
465                 470                 475                 480

Ala Leu Ala Ala Gly His Leu Val Gln Ser His Met Thr His Asn Arg
                485                 490                 495

Lys Pro Ala Glu Pro Thr Lys Pro Asn Asn Leu Asp Ala Thr Asp Ile
            500                 505                 510

Asn Arg Leu Lys Asp Gly Ser Val Thr Cys Ile Lys Ser
        515                 520                 525

<210> SEQ ID NO 25
<211> LENGTH: 1593
<212> TYPE: DNA
<213> ORGANISM: Saccharomyces cerevisiae
<220> FEATURE:
<221> NAME/KEY: CDS
<222> LOCATION: (1)..(1593)

<400> SEQUENCE: 25
```

| | | | | | | | | | | | | | | | | |
|---|---|---|---|---|---|---|---|---|---|---|---|---|---|---|---|---|
| atg | tct | gct | acc | aag | tca | atc | gtt | gga | gag | gca | ttg | gaa | tac | gta | aac | 48 |
| Met | Ser | Ala | Thr | Lys | Ser | Ile | Val | Gly | Glu | Ala | Leu | Glu | Tyr | Val | Asn | |
| 1 | | | | 5 | | | | | 10 | | | | | 15 | | |
| att | ggt | tta | agt | cat | ttc | ttg | gct | tta | cca | ttg | gcc | caa | aga | atc | tct | 96 |
| Ile | Gly | Leu | Ser | His | Phe | Leu | Ala | Leu | Pro | Leu | Ala | Gln | Arg | Ile | Ser | |
| | | | | 20 | | | | | 25 | | | | | 30 | | |
| ttg | atc | ata | ata | att | cct | ttc | att | tac | aat | att | gta | tgg | caa | tta | cta | 144 |
| Leu | Ile | Ile | Ile | Ile | Pro | Phe | Ile | Tyr | Asn | Ile | Val | Trp | Gln | Leu | Leu | |
| | | | 35 | | | | | 40 | | | | | 45 | | | |
| tat | tct | ttg | aga | aag | gac | cgt | cca | cct | cta | gtg | ttt | tac | tgg | att | cca | 192 |
| Tyr | Ser | Leu | Arg | Lys | Asp | Arg | Pro | Pro | Leu | Val | Phe | Tyr | Trp | Ile | Pro | |
| | 50 | | | | | 55 | | | | | 60 | | | | | |
| tgg | gtc | ggt | agt | gct | gtt | gtg | tac | ggt | atg | aag | cca | tac | gag | ttt | ttc | 240 |
| Trp | Val | Gly | Ser | Ala | Val | Val | Tyr | Gly | Met | Lys | Pro | Tyr | Glu | Phe | Phe | |
| 65 | | | | | 70 | | | | | 75 | | | | | 80 | |
| gaa | gaa | tgt | caa | aag | aaa | tac | ggt | gat | att | ttt | tca | ttc | gtt | ttg | tta | 288 |
| Glu | Glu | Cys | Gln | Lys | Lys | Tyr | Gly | Asp | Ile | Phe | Ser | Phe | Val | Leu | Leu | |
| | | | | 85 | | | | | 90 | | | | | 95 | | |
| gga | aga | gtc | atg | act | gtg | tat | tta | gga | cca | aag | ggt | cac | gaa | ttt | gtc | 336 |
| Gly | Arg | Val | Met | Thr | Val | Tyr | Leu | Gly | Pro | Lys | Gly | His | Glu | Phe | Val | |
| | | | | 100 | | | | | 105 | | | | | 110 | | |
| ttc | aac | gct | aag | ttg | gca | gat | gtt | tca | gca | gaa | gct | gct | tac | gct | cat | 384 |
| Phe | Asn | Ala | Lys | Leu | Ala | Asp | Val | Ser | Ala | Glu | Ala | Ala | Tyr | Ala | His | |
| | | | 115 | | | | | 120 | | | | | 125 | | | |
| ttg | act | act | cca | gtt | ttc | ggt | aaa | ggt | gtt | att | tac | gat | tgt | cca | aat | 432 |
| Leu | Thr | Thr | Pro | Val | Phe | Gly | Lys | Gly | Val | Ile | Tyr | Asp | Cys | Pro | Asn | |
| | 130 | | | | | 135 | | | | | 140 | | | | | |
| tct | aga | ttg | atg | gag | caa | aag | aag | ttt | gtt | aag | ggt | gct | cta | acc | aaa | 480 |
| Ser | Arg | Leu | Met | Glu | Gln | Lys | Lys | Phe | Val | Lys | Gly | Ala | Leu | Thr | Lys | |
| 145 | | | | | 150 | | | | | 155 | | | | | 160 | |
| gaa | gcc | ttc | aag | agc | tac | gtt | cca | ttg | att | gct | gaa | gaa | gtg | tac | aag | 528 |
| Glu | Ala | Phe | Lys | Ser | Tyr | Val | Pro | Leu | Ile | Ala | Glu | Glu | Val | Tyr | Lys | |
| | | | | 165 | | | | | 170 | | | | | 175 | | |
| tac | ttc | aga | gac | tcc | aaa | aac | ttc | cgt | ttg | aat | gaa | aga | act | act | ggt | 576 |
| Tyr | Phe | Arg | Asp | Ser | Lys | Asn | Phe | Arg | Leu | Asn | Glu | Arg | Thr | Thr | Gly | |
| | | | | 180 | | | | | 185 | | | | | 190 | | |
| act | att | gac | gtg | atg | gtt | act | caa | cct | gaa | atg | act | att | ttc | acc | gct | 624 |
| Thr | Ile | Asp | Val | Met | Val | Thr | Gln | Pro | Glu | Met | Thr | Ile | Phe | Thr | Ala | |

```
                195                 200                 205
tca aga tca tta ttg ggt aag gaa atg aga gca aaa ttg gat acc gat      672
Ser Arg Ser Leu Leu Gly Lys Glu Met Arg Ala Lys Leu Asp Thr Asp
    210             215                 220 ttt gct tac ttg tac agt gat ttg gat aag ggt ttc act cca atc aac      720
Phe Ala Tyr Leu Tyr Ser Asp Leu Asp Lys Gly Phe Thr Pro Ile Asn
225             230                 235                 240 ttc gtc ttc cct aac tta cca ttg gaa cac tat aga aag aga gat cac      768
Phe Val Phe Pro Asn Leu Pro Leu Glu His Tyr Arg Lys Arg Asp His
                245                 250                 255 gct caa aag gct atc tcc ggt act tac atg tct ttg att aag gaa aga      816
Ala Gln Lys Ala Ile Ser Gly Thr Tyr Met Ser Leu Ile Lys Glu Arg
            260                 265                 270 aga aag aac aac gac att caa gac aga gat ttg atc gat tcc ttg atg      864
Arg Lys Asn Asn Asp Ile Gln Asp Arg Asp Leu Ile Asp Ser Leu Met
        275                 280                 285 aag aac tct acc tac aag gat ggt gtg aag atg act gat caa gaa atc      912
Lys Asn Ser Thr Tyr Lys Asp Gly Val Lys Met Thr Asp Gln Glu Ile
    290                 295                 300 gct aac ttg tta att ggt gtc tta atg ggt ggt caa cat act tct gct      960
Ala Asn Leu Leu Ile Gly Val Leu Met Gly Gly Gln His Thr Ser Ala
305             310                 315                 320 gcc act tct gct tgg att ttg ttg cac ttg gct gaa aga cca gat gtc     1008
Ala Thr Ser Ala Trp Ile Leu Leu His Leu Ala Glu Arg Pro Asp Val
                325                 330                 335 caa caa gaa ttg tac gaa gaa caa atg cgt gtt ttg gat ggt ggt aag     1056
Gln Gln Glu Leu Tyr Glu Glu Gln Met Arg Val Leu Asp Gly Gly Lys
            340                 345                 350 aag gaa ttg acc tac gat tta tta caa gaa atg cca ttg ttg aac caa     1104
Lys Glu Leu Thr Tyr Asp Leu Leu Gln Glu Met Pro Leu Leu Asn Gln
        355                 360                 365 act att aag gaa act cta aga atg cac cat cca ttg cac tct ttg ttc     1152
Thr Ile Lys Glu Thr Leu Arg Met His His Pro Leu His Ser Leu Phe
    370                 375                 380 cgt aag gtt atg aaa gat atg cac gtt cca aac act tct tat gtc atc     1200
Arg Lys Val Met Lys Asp Met His Val Pro Asn Thr Ser Tyr Val Ile
385             390                 395                 400 cca gca ggt tat cac gtt ttg gtt tct cca ggt tac act cat tta aga     1248
Pro Ala Gly Tyr His Val Leu Val Ser Pro Gly Tyr Thr His Leu Arg
                405                 410                 415 gac gaa tac ttc cct aat gct cac caa ttc aac att cac cgt tgg aac     1296
Asp Glu Tyr Phe Pro Asn Ala His Gln Phe Asn Ile His Arg Trp Asn
            420                 425                 430 aaa gat tct gcc tcc tct tat tcc gtc ggt gaa gaa gtc gat tac ggt     1344
Lys Asp Ser Ala Ser Ser Tyr Ser Val Gly Glu Glu Val Asp Tyr Gly
        435                 440                 445 ttc ggt gcc att tct aag ggt gtc agc tct cca tac tta cct ttc ggt     1392
Phe Gly Ala Ile Ser Lys Gly Val Ser Ser Pro Tyr Leu Pro Phe Gly
    450                 455                 460 ggt ggt aga cac aga tgt atc ggt gaa cac ttt gct tac tgt cag cta     1440
Gly Gly Arg His Arg Cys Ile Gly Glu His Phe Ala Tyr Cys Gln Leu
465             470                 475                 480 ggt gtt cta atg tcc att ttt atc aga aca tta aaa tgg cat tac cca     1488
Gly Val Leu Met Ser Ile Phe Ile Arg Thr Leu Lys Trp His Tyr Pro
                485                 490                 495 gag ggt aag acc gtt cca cct cct gac ttt aca tct atg gtt act ctt     1536
Glu Gly Lys Thr Val Pro Pro Pro Asp Phe Thr Ser Met Val Thr Leu
            500                 505                 510 cca acc ggt cca gcc aag atc atc tgg gaa aag aga aat cca gaa caa     1584
```

```
Pro Thr Gly Pro Ala Lys Ile Ile Trp Glu Lys Arg Asn Pro Glu Gln
        515                 520                 525 aag atc taa                                                              1593
Lys Ile
    530

<210> SEQ ID NO 26
<211> LENGTH: 530
<212> TYPE: PRT
<213> ORGANISM: Saccharomyces cerevisiae

<400> SEQUENCE: 26

Met Ser Ala Thr Lys Ser Ile Val Gly Glu Ala Leu Glu Tyr Val Asn
  1               5                  10                  15

Ile Gly Leu Ser His Phe Leu Ala Leu Pro Leu Ala Gln Arg Ile Ser
                 20                  25                  30

Leu Ile Ile Ile Ile Pro Phe Ile Tyr Asn Ile Val Trp Gln Leu Leu
             35                  40                  45

Tyr Ser Leu Arg Lys Asp Arg Pro Pro Leu Val Phe Tyr Trp Ile Pro
     50                  55                  60

Trp Val Gly Ser Ala Val Val Tyr Gly Met Lys Pro Tyr Glu Phe Phe
 65                  70                  75                  80

Glu Glu Cys Gln Lys Lys Tyr Gly Asp Ile Phe Ser Phe Val Leu Leu
                 85                  90                  95

Gly Arg Val Met Thr Val Tyr Leu Gly Pro Lys Gly His Glu Phe Val
                100                 105                 110

Phe Asn Ala Lys Leu Ala Asp Val Ser Ala Glu Ala Ala Tyr Ala His
            115                 120                 125

Leu Thr Thr Pro Val Phe Gly Lys Gly Val Ile Tyr Asp Cys Pro Asn
    130                 135                 140

Ser Arg Leu Met Glu Gln Lys Lys Phe Val Lys Gly Ala Leu Thr Lys
145                 150                 155                 160

Glu Ala Phe Lys Ser Tyr Val Pro Leu Ile Ala Glu Glu Val Tyr Lys
                165                 170                 175

Tyr Phe Arg Asp Ser Lys Asn Phe Arg Leu Asn Glu Arg Thr Thr Gly
            180                 185                 190

Thr Ile Asp Val Met Val Thr Gln Pro Glu Met Thr Ile Phe Thr Ala
        195                 200                 205

Ser Arg Ser Leu Leu Gly Lys Glu Met Arg Ala Lys Leu Asp Thr Asp
    210                 215                 220

Phe Ala Tyr Leu Tyr Ser Asp Leu Asp Lys Gly Phe Thr Pro Ile Asn
225                 230                 235                 240

Phe Val Phe Pro Asn Leu Pro Leu Glu His Tyr Arg Lys Arg Asp His
                245                 250                 255

Ala Gln Lys Ala Ile Ser Gly Thr Tyr Met Ser Leu Ile Lys Glu Arg
            260                 265                 270

Arg Lys Asn Asn Asp Ile Gln Asp Arg Asp Leu Ile Asp Ser Leu Met
        275                 280                 285

Lys Asn Ser Thr Tyr Lys Asp Gly Val Lys Met Thr Asp Gln Glu Ile
    290                 295                 300

Ala Asn Leu Leu Ile Gly Val Leu Met Gly Gly Gln His Thr Ser Ala
305                 310                 315                 320

Ala Thr Ser Ala Trp Ile Leu Leu His Leu Ala Glu Arg Pro Asp Val
                325                 330                 335

Gln Gln Glu Leu Tyr Glu Glu Gln Met Arg Val Leu Asp Gly Gly Lys
```

```
                340                 345                 350
Lys Glu Leu Thr Tyr Asp Leu Leu Gln Glu Met Pro Leu Leu Asn Gln
                355                 360                 365

Thr Ile Lys Glu Thr Leu Arg Met His His Pro Leu His Ser Leu Phe
        370                 375                 380

Arg Lys Val Met Lys Asp Met His Val Pro Asn Thr Ser Tyr Val Ile
385                 390                 395                 400

Pro Ala Gly Tyr His Val Leu Val Ser Pro Gly Tyr Thr His Leu Arg
                405                 410                 415

Asp Glu Tyr Phe Pro Asn Ala His Gln Phe Asn Ile His Arg Trp Asn
            420                 425                 430

Lys Asp Ser Ala Ser Ser Tyr Ser Val Gly Glu Val Asp Tyr Gly
                435                 440                 445

Phe Gly Ala Ile Ser Lys Gly Val Ser Ser Pro Tyr Leu Pro Phe Gly
            450                 455                 460

Gly Gly Arg His Arg Cys Ile Gly Glu His Phe Ala Tyr Cys Gln Leu
465                 470                 475                 480

Gly Val Leu Met Ser Ile Phe Ile Arg Thr Leu Lys Trp His Tyr Pro
                485                 490                 495

Glu Gly Lys Thr Val Pro Pro Asp Phe Thr Ser Met Val Thr Leu
            500                 505                 510

Pro Thr Gly Pro Ala Lys Ile Ile Trp Glu Lys Arg Asn Pro Glu Gln
                515                 520                 525

Lys Ile
    530
```

<210> SEQ ID NO 27
<211> LENGTH: 1491
<212> TYPE: DNA
<213> ORGANISM: Saccharomyces cerevisiae
<220> FEATURE:
<221> NAME/KEY: CDS
<222> LOCATION: (1)..(1491)

<400> SEQUENCE: 27

```
atg tct gct gtt aac gtt gca cct gaa ttg att aat gcc gac aac aca      48
Met Ser Ala Val Asn Val Ala Pro Glu Leu Ile Asn Ala Asp Asn Thr
 1               5                  10                  15 att acc tac gat gcg att gtc atc ggt gct ggt gtt atc ggt cca tgt      96
Ile Thr Tyr Asp Ala Ile Val Ile Gly Ala Gly Val Ile Gly Pro Cys
             20                  25                  30 gtt gct act ggt cta gca aga aag ggt aag aaa gtt ctt atc gta gaa     144
Val Ala Thr Gly Leu Ala Arg Lys Gly Lys Lys Val Leu Ile Val Glu
         35                  40                  45 cgt gac tgg gct atg cct gat aga att gtt ggt gaa ttg atg caa cca     192
Arg Asp Trp Ala Met Pro Asp Arg Ile Val Gly Glu Leu Met Gln Pro
     50                  55                  60 ggt ggt gtt aga gca ttg aga agt ctg ggt atg att caa tct atc aac     240
Gly Gly Val Arg Ala Leu Arg Ser Leu Gly Met Ile Gln Ser Ile Asn
 65                  70                  75                  80 aac atc gaa gca tat cct gtt acc ggt tat acc gtc ttt ttc aac ggc     288
Asn Ile Glu Ala Tyr Pro Val Thr Gly Tyr Thr Val Phe Phe Asn Gly
                 85                  90                  95 gaa caa gtt gat att cca tac cct tac aag gcc gat atc cct aaa gtt     336
Glu Gln Val Asp Ile Pro Tyr Pro Tyr Lys Ala Asp Ile Pro Lys Val
            100                 105                 110 gaa aaa ttg aag gac ttg gtc aaa gat ggt aat gac aag gtc ttg gaa     384
Glu Lys Leu Lys Asp Leu Val Lys Asp Gly Asn Asp Lys Val Leu Glu
```

-continued

```
             115                 120                 125
gac agc act att cac atc aag gat tac gaa gat gat gaa aga gaa agg     432
Asp Ser Thr Ile His Ile Lys Asp Tyr Glu Asp Asp Glu Arg Glu Arg
        130                 135                 140 ggt gtt gct ttt gtt cat ggt aga ttc ttg aac aac ttg aga aac att     480
Gly Val Ala Phe Val His Gly Arg Phe Leu Asn Asn Leu Arg Asn Ile
145                 150                 155                 160 act gct caa gag cca aat gtt act aga gtg caa ggt aac tgt att gag     528
Thr Ala Gln Glu Pro Asn Val Thr Arg Val Gln Gly Asn Cys Ile Glu
                165                 170                 175 ata ttg aag gat gaa aag aat gag gtt gtt ggt gcc aag gtt gac att     576
Ile Leu Lys Asp Glu Lys Asn Glu Val Val Gly Ala Lys Val Asp Ile
            180                 185                 190 gat ggc cgt ggc aag gtg gaa ttc aaa gcc cac ttg aca ttt atc tgt     624
Asp Gly Arg Gly Lys Val Glu Phe Lys Ala His Leu Thr Phe Ile Cys
                195                 200                 205 gac ggt atc ttt tca cgt ttc aga aag gaa ttg cac cca gac cat gtt     672
Asp Gly Ile Phe Ser Arg Phe Arg Lys Glu Leu His Pro Asp His Val
        210                 215                 220 cca act gtc ggt tct tcg ttt gtc ggt atg tct ttg ttc aat gct aag     720
Pro Thr Val Gly Ser Ser Phe Val Gly Met Ser Leu Phe Asn Ala Lys
225                 230                 235                 240 aat cct gct cct atg cac ggt cac gtt att ctt ggt agt gat cat atg     768
Asn Pro Ala Pro Met His Gly His Val Ile Leu Gly Ser Asp His Met
                245                 250                 255 cca atc ttg gtt tac caa atc agt cca gaa gaa aca aga atc ctt tgt     816
Pro Ile Leu Val Tyr Gln Ile Ser Pro Glu Glu Thr Arg Ile Leu Cys
            260                 265                 270 gct tac aac tct cca aag gtc cca gct gat atc aag agt tgg atg att     864
Ala Tyr Asn Ser Pro Lys Val Pro Ala Asp Ile Lys Ser Trp Met Ile
        275                 280                 285 aag gat gtc caa cct ttc att cca aag agt cta cgt cct tca ttt gat     912
Lys Asp Val Gln Pro Phe Ile Pro Lys Ser Leu Arg Pro Ser Phe Asp
290                 295                 300 gaa gcc gtc agc caa ggt aaa ttt aga gct atg cca aac tcc tac ttg     960
Glu Ala Val Ser Gln Gly Lys Phe Arg Ala Met Pro Asn Ser Tyr Leu
305                 310                 315                 320 cca gct aga caa aac gac gtc act ggt atg tgt gtt atc ggt gac gct    1008
Pro Ala Arg Gln Asn Asp Val Thr Gly Met Cys Val Ile Gly Asp Ala
                325                 330                 335 cta aat atg aga cat cca ttg act ggt ggt ggt atg act gtc ggt ttg    1056
Leu Asn Met Arg His Pro Leu Thr Gly Gly Gly Met Thr Val Gly Leu
            340                 345                 350 cat gat gtt gtc ttg ttg att aag aaa ata ggt gac cta gac ttc agc    1104
His Asp Val Val Leu Leu Ile Lys Lys Ile Gly Asp Leu Asp Phe Ser
        355                 360                 365 gac cgt gaa aag gtt ttg gat gaa tta cta gac tac cat ttc gaa aga    1152
Asp Arg Glu Lys Val Leu Asp Glu Leu Leu Asp Tyr His Phe Glu Arg
370                 375                 380 aag agt tac gat tcc gtt att aac gtt ttg tca gtg gct ttg tat tct    1200
Lys Ser Tyr Asp Ser Val Ile Asn Val Leu Ser Val Ala Leu Tyr Ser
385                 390                 395                 400 ttg ttc gct gct gac agc gat aac ttg aag gca tta caa aaa ggt tgt    1248
Leu Phe Ala Ala Asp Ser Asp Asn Leu Lys Ala Leu Gln Lys Gly Cys
                405                 410                 415 ttc aaa tat ttc caa aga ggt ggc gat tgt gtc aac aaa ccc gtt gaa    1296
Phe Lys Tyr Phe Gln Arg Gly Gly Asp Cys Val Asn Lys Pro Val Glu
            420                 425                 430 ttt ctg tct ggt gtc ttg cca aag cct ttg caa ttg acc agg gtt ttc    1344
```

```
                                         -continued

Phe Leu Ser Gly Val Leu Pro Lys Pro Leu Gln Leu Thr Arg Val Phe
        435                 440                 445 ttc gct gtc gct ttt tac acc att tac ttg aac atg gaa gaa cgt ggt      1392
Phe Ala Val Ala Phe Tyr Thr Ile Tyr Leu Asn Met Glu Glu Arg Gly
450                 455                 460 ttc ttg gga tta cca atg gct tta ttg gaa ggt att atg att ttg atc      1440
Phe Leu Gly Leu Pro Met Ala Leu Leu Glu Gly Ile Met Ile Leu Ile
465                 470                 475                 480 aca gct att aga gta ttc acc cca ttt ttg ttt ggt gag ttg att ggt      1488
Thr Ala Ile Arg Val Phe Thr Pro Phe Leu Phe Gly Glu Leu Ile Gly
                485                 490                 495 taa                                                                  1491

<210> SEQ ID NO 28
<211> LENGTH: 496
<212> TYPE: PRT
<213> ORGANISM: Saccharomyces cerevisiae

<400> SEQUENCE: 28

Met Ser Ala Val Asn Val Ala Pro Glu Leu Ile Asn Ala Asp Asn Thr
  1               5                  10                  15

Ile Thr Tyr Asp Ala Ile Val Ile Gly Ala Gly Val Ile Gly Pro Cys
             20                  25                  30

Val Ala Thr Gly Leu Ala Arg Lys Gly Lys Lys Val Leu Ile Val Glu
         35                  40                  45

Arg Asp Trp Ala Met Pro Asp Arg Ile Val Gly Glu Leu Met Gln Pro
     50                  55                  60

Gly Gly Val Arg Ala Leu Arg Ser Leu Gly Met Ile Gln Ser Ile Asn
 65                  70                  75                  80

Asn Ile Glu Ala Tyr Pro Val Thr Gly Tyr Thr Val Phe Phe Asn Gly
                 85                  90                  95

Glu Gln Val Asp Ile Pro Tyr Pro Tyr Lys Ala Asp Ile Pro Lys Val
            100                 105                 110

Glu Lys Leu Lys Asp Leu Val Lys Asp Gly Asn Asp Lys Val Leu Glu
        115                 120                 125

Asp Ser Thr Ile His Ile Lys Asp Tyr Glu Asp Asp Glu Arg Glu Arg
    130                 135                 140

Gly Val Ala Phe Val His Gly Arg Phe Leu Asn Asn Leu Arg Asn Ile
145                 150                 155                 160

Thr Ala Gln Glu Pro Asn Val Thr Arg Val Gln Gly Asn Cys Ile Glu
                165                 170                 175

Ile Leu Lys Asp Glu Lys Asn Glu Val Val Gly Ala Lys Val Asp Ile
            180                 185                 190

Asp Gly Arg Gly Lys Val Glu Phe Lys Ala His Leu Thr Phe Ile Cys
        195                 200                 205

Asp Gly Ile Phe Ser Arg Phe Arg Lys Glu Leu His Pro Asp His Val
    210                 215                 220

Pro Thr Val Gly Ser Ser Phe Val Gly Met Ser Leu Phe Asn Ala Lys
225                 230                 235                 240

Asn Pro Ala Pro Met His Gly His Val Ile Leu Gly Ser Asp His Met
                245                 250                 255

Pro Ile Leu Val Tyr Gln Ile Ser Pro Glu Glu Thr Arg Ile Leu Cys
            260                 265                 270

Ala Tyr Asn Ser Pro Lys Val Pro Ala Asp Ile Lys Ser Trp Met Ile
        275                 280                 285
```

-continued

```
Lys Asp Val Gln Pro Phe Ile Pro Lys Ser Leu Arg Pro Ser Phe Asp
    290                 295                 300
Glu Ala Val Ser Gln Gly Lys Phe Arg Ala Met Pro Asn Ser Tyr Leu
305                 310                 315                 320
Pro Ala Arg Gln Asn Asp Val Thr Gly Met Cys Val Ile Gly Asp Ala
                325                 330                 335
Leu Asn Met Arg His Pro Leu Thr Gly Gly Met Thr Val Gly Leu
            340                 345                 350
His Asp Val Val Leu Leu Ile Lys Lys Ile Gly Asp Leu Asp Phe Ser
        355                 360                 365
Asp Arg Glu Lys Val Leu Asp Glu Leu Leu Asp Tyr His Phe Glu Arg
    370                 375                 380
Lys Ser Tyr Asp Ser Val Ile Asn Val Leu Ser Val Ala Leu Tyr Ser
385                 390                 395                 400
Leu Phe Ala Ala Asp Ser Asp Asn Leu Lys Ala Leu Gln Lys Gly Cys
                405                 410                 415
Phe Lys Tyr Phe Gln Arg Gly Gly Asp Cys Val Asn Lys Pro Val Glu
            420                 425                 430
Phe Leu Ser Gly Val Leu Pro Lys Pro Leu Gln Leu Thr Arg Val Phe
        435                 440                 445
Phe Ala Val Ala Phe Tyr Thr Ile Tyr Leu Asn Met Glu Glu Arg Gly
    450                 455                 460
Phe Leu Gly Leu Pro Met Ala Leu Leu Glu Gly Ile Met Ile Leu Ile
465                 470                 475                 480
Thr Ala Ile Arg Val Phe Thr Pro Phe Leu Phe Gly Glu Leu Ile Gly
                485                 490                 495

<210> SEQ ID NO 29
<211> LENGTH: 1335
<212> TYPE: DNA
<213> ORGANISM: Saccharomyces cerevisiae
<220> FEATURE:
<221> NAME/KEY: CDS
<222> LOCATION: (1)..(1335)

<400> SEQUENCE: 29 atg gga aag cta tta caa ttg gca ttg cat ccg gtc gag atg aag gca      48
Met Gly Lys Leu Leu Gln Leu Ala Leu His Pro Val Glu Met Lys Ala
 1               5                  10                  15 gct ttg aag ctg aag ttt tgc aga aca ccg cta ttc tcc atc tat gat      96
Ala Leu Lys Leu Lys Phe Cys Arg Thr Pro Leu Phe Ser Ile Tyr Asp
             20                  25                  30 cag tcc acg tct cca tat ctc ttg cac tgt ttc gaa ctg ttg aac ttg     144
Gln Ser Thr Ser Pro Tyr Leu Leu His Cys Phe Glu Leu Leu Asn Leu
         35                  40                  45 acc tcc aga tcg ttt gct gct gtg atc aga gag ctg cat cca gaa ttg     192
Thr Ser Arg Ser Phe Ala Ala Val Ile Arg Glu Leu His Pro Glu Leu
     50                  55                  60 aga aac tgt gtt act ctc ttt tat ttg att tta agg gct ttg gat acc     240
Arg Asn Cys Val Thr Leu Phe Tyr Leu Ile Leu Arg Ala Leu Asp Thr
 65                  70                  75                  80 atc gaa gac gat atg tcc atc gaa cac gat ttg aaa att gac ttg ttg     288
Ile Glu Asp Asp Met Ser Ile Glu His Asp Leu Lys Ile Asp Leu Leu
                 85                  90                  95 cgt cac ttc cac gag aaa ttg ttg tta act aaa tgg agt ttc gac gga     336
Arg His Phe His Glu Lys Leu Leu Leu Thr Lys Trp Ser Phe Asp Gly
            100                 105                 110 aat gcc ccc gat gtg aag gac aga gcc gtt ttg aca gat ttc gaa tcg     384
Asn Ala Pro Asp Val Lys Asp Arg Ala Val Leu Thr Asp Phe Glu Ser
```

```
                Asn Ala Pro Asp Val Lys Asp Arg Ala Val Leu Thr Asp Phe Glu Ser
                    115                 120                 125 att ctt att gaa ttc cac aaa ttg aaa cca gaa tat caa gaa gtc atc            432
Ile Leu Ile Glu Phe His Lys Leu Lys Pro Glu Tyr Gln Glu Val Ile
130                 135                 140 aag gag atc acc gag aaa atg ggt aat ggt atg gcc gac tac atc tta            480
Lys Glu Ile Thr Glu Lys Met Gly Asn Gly Met Ala Asp Tyr Ile Leu
145                 150                 155                 160 gat gaa aat tac aac ttg aat ggg ttg caa acc gtc cac gac tac gac            528
Asp Glu Asn Tyr Asn Leu Asn Gly Leu Gln Thr Val His Asp Tyr Asp
                165                 170                 175 gtg tac tgt cac tac gta gct ggt ttg gtc ggt gat ggt ttg acc cgt            576
Val Tyr Cys His Tyr Val Ala Gly Leu Val Gly Asp Gly Leu Thr Arg
                180                 185                 190 ttg att gtc att gcc aag ttt gcc aac gaa tct ttg tat tct aat gag            624
Leu Ile Val Ile Ala Lys Phe Ala Asn Glu Ser Leu Tyr Ser Asn Glu
            195                 200                 205 caa ttg tat gaa agc atg ggt ctt ttc cta caa aaa acc aac atc atc            672
Gln Leu Tyr Glu Ser Met Gly Leu Phe Leu Gln Lys Thr Asn Ile Ile
210                 215                 220 aga gat tac aat gaa gat ttg gtc gat ggt aga tcc ttc tgg ccc aag            720
Arg Asp Tyr Asn Glu Asp Leu Val Asp Gly Arg Ser Phe Trp Pro Lys
225                 230                 235                 240 gaa atc tgg tca caa tac gct cct cag ttg aag gac ttc atg aaa cct            768
Glu Ile Trp Ser Gln Tyr Ala Pro Gln Leu Lys Asp Phe Met Lys Pro
                245                 250                 255 gaa aac gaa caa ctg ggg ttg gac tgt ata aac cac ctc gtc tta aac            816
Glu Asn Glu Gln Leu Gly Leu Asp Cys Ile Asn His Leu Val Leu Asn
                260                 265                 270 gca ttg agt cat gtt atc gat gtg ttg act tat ttg gcc ggt atc cac            864
Ala Leu Ser His Val Ile Asp Val Leu Thr Tyr Leu Ala Gly Ile His
            275                 280                 285 gag caa tcc act ttc caa ttt tgt gcc att ccc caa gtt atg gcc att            912
Glu Gln Ser Thr Phe Gln Phe Cys Ala Ile Pro Gln Val Met Ala Ile
290                 295                 300 gca acc ttg gct ttg gta ttc aac aac cgt gaa gtg cta cat ggc aat            960
Ala Thr Leu Ala Leu Val Phe Asn Asn Arg Glu Val Leu His Gly Asn
305                 310                 315                 320 gta aag att cgt aag ggt act acc tgc tat tta att ttg aaa tca agg           1008
Val Lys Ile Arg Lys Gly Thr Thr Cys Tyr Leu Ile Leu Lys Ser Arg
                325                 330                 335 act ttg cgt ggc tgt gtc gag att ttt gac tat tac tta cgt gat atc           1056
Thr Leu Arg Gly Cys Val Glu Ile Phe Asp Tyr Tyr Leu Arg Asp Ile
                340                 345                 350 aaa tct aaa ttg gct gtg caa gat cca aat ttc tta aaa ttg aac att           1104
Lys Ser Lys Leu Ala Val Gln Asp Pro Asn Phe Leu Lys Leu Asn Ile
            355                 360                 365 caa atc tcc aag atc gaa cag ttt atg gaa gaa atg tac cag gat aaa           1152
Gln Ile Ser Lys Ile Glu Gln Phe Met Glu Glu Met Tyr Gln Asp Lys
370                 375                 380 tta cct cct aac gtg aag cca aat gaa act cca att ttc ttg aaa gtt           1200
Leu Pro Pro Asn Val Lys Pro Asn Glu Thr Pro Ile Phe Leu Lys Val
385                 390                 395                 400 aaa gaa aga tcc aga tac gat gat gaa ttg gtt cca acc caa caa gaa           1248
Lys Glu Arg Ser Arg Tyr Asp Asp Glu Leu Val Pro Thr Gln Gln Glu
                405                 410                 415 gaa gag tac aag ttc aat atg gtt tta tct atc atc ttg tcc gtt ctt           1296
Glu Glu Tyr Lys Phe Asn Met Val Leu Ser Ile Ile Leu Ser Val Leu
                420                 425                 430
```

```
ctt ggg ttt tat tat ata tac act tta cac aga gcg tga                1335
Leu Gly Phe Tyr Tyr Ile Tyr Thr Leu His Arg Ala
        435                 440
```

<210> SEQ ID NO 30
<211> LENGTH: 444
<212> TYPE: PRT
<213> ORGANISM: Saccharomyces cerevisiae

<400> SEQUENCE: 30

```
Met Gly Lys Leu Leu Gln Leu Ala Leu His Pro Val Glu Met Lys Ala
 1               5                  10                  15

Ala Leu Lys Leu Lys Phe Cys Arg Thr Pro Leu Phe Ser Ile Tyr Asp
            20                  25                  30

Gln Ser Thr Ser Pro Tyr Leu Leu His Cys Phe Glu Leu Leu Asn Leu
        35                  40                  45

Thr Ser Arg Ser Phe Ala Ala Val Ile Arg Glu Leu His Pro Glu Leu
    50                  55                  60

Arg Asn Cys Val Thr Leu Phe Tyr Leu Ile Leu Arg Ala Leu Asp Thr
65                  70                  75                  80

Ile Glu Asp Asp Met Ser Ile Glu His Asp Leu Lys Ile Asp Leu Leu
                85                  90                  95

Arg His Phe His Glu Lys Leu Leu Leu Thr Lys Trp Ser Phe Asp Gly
            100                 105                 110

Asn Ala Pro Asp Val Lys Asp Arg Ala Val Leu Thr Asp Phe Glu Ser
        115                 120                 125

Ile Leu Ile Glu Phe His Lys Leu Lys Pro Glu Tyr Gln Glu Val Ile
    130                 135                 140

Lys Glu Ile Thr Glu Lys Met Gly Asn Gly Met Ala Asp Tyr Ile Leu
145                 150                 155                 160

Asp Glu Asn Tyr Asn Leu Asn Gly Leu Gln Thr Val His Asp Tyr Asp
                165                 170                 175

Val Tyr Cys His Tyr Val Ala Gly Leu Val Gly Asp Gly Leu Thr Arg
            180                 185                 190

Leu Ile Val Ile Ala Lys Phe Ala Asn Glu Ser Leu Tyr Ser Asn Glu
        195                 200                 205

Gln Leu Tyr Glu Ser Met Gly Leu Phe Leu Gln Lys Thr Asn Ile Ile
    210                 215                 220

Arg Asp Tyr Asn Glu Asp Leu Val Asp Gly Arg Ser Phe Trp Pro Lys
225                 230                 235                 240

Glu Ile Trp Ser Gln Tyr Ala Pro Gln Leu Lys Asp Phe Met Lys Pro
                245                 250                 255

Glu Asn Glu Gln Leu Gly Leu Asp Cys Ile Asn His Leu Val Leu Asn
            260                 265                 270

Ala Leu Ser His Val Ile Asp Val Leu Thr Tyr Leu Ala Gly Ile His
        275                 280                 285

Glu Gln Ser Thr Phe Gln Phe Cys Ala Ile Pro Gln Val Met Ala Ile
    290                 295                 300

Ala Thr Leu Ala Leu Val Phe Asn Asn Arg Glu Val Leu His Gly Asn
305                 310                 315                 320

Val Lys Ile Arg Lys Gly Thr Thr Cys Tyr Leu Ile Leu Lys Ser Arg
                325                 330                 335

Thr Leu Arg Gly Cys Val Glu Ile Phe Asp Tyr Tyr Leu Arg Asp Ile
            340                 345                 350

Lys Ser Lys Leu Ala Val Gln Asp Pro Asn Phe Leu Lys Leu Asn Ile
```

```
                  355                 360                 365
Gln Ile Ser Lys Ile Glu Gln Phe Met Glu Met Tyr Gln Asp Lys
            370                 375                 380

Leu Pro Pro Asn Val Lys Pro Asn Glu Thr Pro Ile Phe Leu Lys Val
385                 390                 395                 400

Lys Glu Arg Ser Arg Tyr Asp Asp Glu Leu Val Pro Thr Gln Gln Glu
                405                 410                 415

Glu Glu Tyr Lys Phe Asn Met Val Leu Ser Ile Ile Leu Ser Val Leu
            420                 425                 430

Leu Gly Phe Tyr Tyr Ile Tyr Thr Leu His Arg Ala
            435                 440

<210> SEQ ID NO 31
<211> LENGTH: 1929
<212> TYPE: DNA
<213> ORGANISM: Saccharomyces cerevisiae
<220> FEATURE:
<221> NAME/KEY: CDS
<222> LOCATION: (1)..(1929)

<400> SEQUENCE: 31 atg gac aag aag aag gat cta ctg gag aac gaa caa ttt ctc cgc atc      48
Met Asp Lys Lys Lys Asp Leu Leu Glu Asn Glu Gln Phe Leu Arg Ile
  1               5                  10                  15 caa aag ctc aac gct gcc gat gcg ggc aaa aga caa tct ata aca gtg      96
Gln Lys Leu Asn Ala Ala Asp Ala Gly Lys Arg Gln Ser Ile Thr Val
                 20                  25                  30 gac gac gag ggc gaa cta tat ggg tta gac acc tcc ggc aac tca cca     144
Asp Asp Glu Gly Glu Leu Tyr Gly Leu Asp Thr Ser Gly Asn Ser Pro
             35                  40                  45 gcc aat gaa cac aca gct acc aca att aca cag aat cac agc gtg gtg     192
Ala Asn Glu His Thr Ala Thr Thr Ile Thr Gln Asn His Ser Val Val
         50                  55                  60 gcc tca aac gga gac gtc gca ttc atc cca gga act gct acc gaa ggc     240
Ala Ser Asn Gly Asp Val Ala Phe Ile Pro Gly Thr Ala Thr Glu Gly
 65                  70                  75                  80 aat aca gag att gta act gaa gaa gtg att gag acc gat gat aac atg     288
Asn Thr Glu Ile Val Thr Glu Glu Val Ile Glu Thr Asp Asp Asn Met
                 85                  90                  95 ttc aag acc cat gtg aag act tta agc tcc aaa gag aag gca cgg tat     336
Phe Lys Thr His Val Lys Thr Leu Ser Ser Lys Glu Lys Ala Arg Tyr
            100                 105                 110 agg caa ggg tcc tct aac ttt ata tcg tat ttc gat gat atg tca ttt     384
Arg Gln Gly Ser Ser Asn Phe Ile Ser Tyr Phe Asp Asp Met Ser Phe
        115                 120                 125 gaa cac agg ccc agt ata tta gat ggg tca gtt aac gag ccc ttc aag     432
Glu His Arg Pro Ser Ile Leu Asp Gly Ser Val Asn Glu Pro Phe Lys
    130                 135                 140 acc aaa ttc gtg gga cct act tta gaa aag gag atc aga aga agg gag     480
Thr Lys Phe Val Gly Pro Thr Leu Glu Lys Glu Ile Arg Arg Arg Glu
145                 150                 155                 160 aaa gag cta atg gcc atg cgc aaa aat tta cac cac cgc aag tcc tcc     528
Lys Glu Leu Met Ala Met Arg Lys Asn Leu His His Arg Lys Ser Ser
                165                 170                 175 cca gat gct gtc gac tca gta ggg aaa aat gat ggc gcc gcc cca act     576
Pro Asp Ala Val Asp Ser Val Gly Lys Asn Asp Gly Ala Ala Pro Thr
            180                 185                 190 act gtt cca act gcc gcc acc tca gaa acg gtg gtc acc gtt gaa acc     624
Thr Val Pro Thr Ala Ala Thr Ser Glu Thr Val Val Thr Val Glu Thr
        195                 200                 205
```

```
                                                   -continued acc ata att tca tcc aat ttc tcc ggg ttg tac gtg gcg ttt tgg atg      672
Thr Ile Ile Ser Ser Asn Phe Ser Gly Leu Tyr Val Ala Phe Trp Met
    210                 215                 220 gct att gca ttt ggt gct gtc aag gct tta ata gac tat tat tac cag      720
Ala Ile Ala Phe Gly Ala Val Lys Ala Leu Ile Asp Tyr Tyr Tyr Gln
225                 230                 235                 240 cat aat ggt agc ttc aag gat tcg gag atc ttg aaa ttt atg act acg      768
His Asn Gly Ser Phe Lys Asp Ser Glu Ile Leu Lys Phe Met Thr Thr
            245                 250                 255 aat ttg ttc act gtg gca tcc gta gat ctt ttg atg tat ttg agc act      816
Asn Leu Phe Thr Val Ala Ser Val Asp Leu Leu Met Tyr Leu Ser Thr
        260                 265                 270 tat ttt gtc gtt gga ata caa tac tta tgc aag tgg ggg gtc ttg aaa      864
Tyr Phe Val Val Gly Ile Gln Tyr Leu Cys Lys Trp Gly Val Leu Lys
    275                 280                 285 tgg ggc act acc ggc tgg atc ttc acc tca att tac gag ttt ttg ttt      912
Trp Gly Thr Thr Gly Trp Ile Phe Thr Ser Ile Tyr Glu Phe Leu Phe
290                 295                 300 gtt atc ttc tac atg tat tta aca gaa aac atc cta aaa cta cac tgg      960
Val Ile Phe Tyr Met Tyr Leu Thr Glu Asn Ile Leu Lys Leu His Trp
305                 310                 315                 320 ctg tcc aag atc ttc ctt ttt ttg cat tct tta gtt tta ttg atg aaa     1008
Leu Ser Lys Ile Phe Leu Phe Leu His Ser Leu Val Leu Leu Met Lys
            325                 330                 335 atg cat tct ttc gcc ttc tac aat ggc tat cta tgg ggt ata aag gaa     1056
Met His Ser Phe Ala Phe Tyr Asn Gly Tyr Leu Trp Gly Ile Lys Glu
        340                 345                 350 gaa cta caa ttt tcc aaa agc gct ctt gcc aaa tac aag gat tct ata     1104
Glu Leu Gln Phe Ser Lys Ser Ala Leu Ala Lys Tyr Lys Asp Ser Ile
    355                 360                 365 aat gat cca aaa gtt att ggt gct ctt gag aaa agc tgt gag ttt tgt     1152
Asn Asp Pro Lys Val Ile Gly Ala Leu Glu Lys Ser Cys Glu Phe Cys
370                 375                 380 agt ttt gaa ttg agc tct cag tct tta agc gac caa act caa aaa ttc     1200
Ser Phe Glu Leu Ser Ser Gln Ser Leu Ser Asp Gln Thr Gln Lys Phe
385                 390                 395                 400 ccc aac aat atc agt gca aaa agc ttt ttt tgg ttc acc atg ttt cca     1248
Pro Asn Asn Ile Ser Ala Lys Ser Phe Phe Trp Phe Thr Met Phe Pro
            405                 410                 415 acc cta att tac caa att gaa tat cca aga act aag gaa atc aga tgg     1296
Thr Leu Ile Tyr Gln Ile Glu Tyr Pro Arg Thr Lys Glu Ile Arg Trp
        420                 425                 430 agc tac gta tta gaa aag atc tgc gcc atc ttc ggt acc att ttc tta     1344
Ser Tyr Val Leu Glu Lys Ile Cys Ala Ile Phe Gly Thr Ile Phe Leu
    435                 440                 445 atg atg ata gat gct caa atc ttg atg tat cct gta gca atg aga gca     1392
Met Met Ile Asp Ala Gln Ile Leu Met Tyr Pro Val Ala Met Arg Ala
450                 455                 460 ttg gct gtg cgc aat tct gaa tgg act ggt ata ttg gat aga tta ttg     1440
Leu Ala Val Arg Asn Ser Glu Trp Thr Gly Ile Leu Asp Arg Leu Leu
465                 470                 475                 480 aaa tgg gtt gga ttg ctc gtt gat atc gtc cca ggg ttt atc gtg atg     1488
Lys Trp Val Gly Leu Leu Val Asp Ile Val Pro Gly Phe Ile Val Met
            485                 490                 495 tac atc ttg gac ttc tat ttg att tgg gat gcc att ttg aac tgt gtg     1536
Tyr Ile Leu Asp Phe Tyr Leu Ile Trp Asp Ala Ile Leu Asn Cys Val
        500                 505                 510 gct gaa ttg aca aga ttt ggc gac aga tat ttc tac ggt gac tgg tgg     1584
Ala Glu Leu Thr Arg Phe Gly Asp Arg Tyr Phe Tyr Gly Asp Trp Trp
```

```
                515                 520                 525
aat tgt gtt agt tgg gca gac ttc agt aga att tgg aac atc cca gtg      1632
Asn Cys Val Ser Trp Ala Asp Phe Ser Arg Ile Trp Asn Ile Pro Val
530                 535                 540 cat aag ttt ttg tta aga cat gtt tac cat agt tca atg agt tca ttc      1680
His Lys Phe Leu Leu Arg His Val Tyr His Ser Ser Met Ser Ser Phe
545                 550                 555                 560 aaa ttg aac aag agt caa gca act ttg atg acc ttt ttc tta agt tcc      1728
Lys Leu Asn Lys Ser Gln Ala Thr Leu Met Thr Phe Phe Leu Ser Ser
                565                 570                 575 gtc gtt cat gaa tta gca atg tac gtt atc ttc aag aaa ttg agg ttt      1776
Val Val His Glu Leu Ala Met Tyr Val Ile Phe Lys Lys Leu Arg Phe
            580                 585                 590 tac ttg ttc ttc ttc caa atg ctg caa atg cca tta gta gct tta aca      1824
Tyr Leu Phe Phe Phe Gln Met Leu Gln Met Pro Leu Val Ala Leu Thr
        595                 600                 605 aat act aaa ttc atg agg aac aga acc ata atc gga aat gtt att ttc      1872
Asn Thr Lys Phe Met Arg Asn Arg Thr Ile Ile Gly Asn Val Ile Phe
    610                 615                 620 tgg ctc ggt atc tgc atg gga cca agt gtc atg tgt acg ttg tac ttg      1920
Trp Leu Gly Ile Cys Met Gly Pro Ser Val Met Cys Thr Leu Tyr Leu
625                 630                 635                 640 aca ttc taa                                                          1929
Thr Phe <210> SEQ ID NO 32
<211> LENGTH: 642
<212> TYPE: PRT
<213> ORGANISM: Saccharomyces cerevisiae

<400> SEQUENCE: 32

Met Asp Lys Lys Lys Asp Leu Leu Glu Asn Glu Gln Phe Leu Arg Ile
  1               5                  10                  15

Gln Lys Leu Asn Ala Ala Asp Ala Gly Lys Arg Gln Ser Ile Thr Val
                 20                  25                  30

Asp Asp Glu Gly Glu Leu Tyr Gly Leu Asp Thr Ser Gly Asn Ser Pro
             35                  40                  45

Ala Asn Glu His Thr Ala Thr Thr Ile Thr Gln Asn His Ser Val Val
         50                  55                  60

Ala Ser Asn Gly Asp Val Ala Phe Ile Pro Gly Thr Ala Thr Glu Gly
 65                  70                  75                  80

Asn Thr Glu Ile Val Thr Glu Glu Val Ile Glu Thr Asp Asp Asn Met
                 85                  90                  95

Phe Lys Thr His Val Lys Thr Leu Ser Ser Lys Glu Lys Ala Arg Tyr
            100                 105                 110

Arg Gln Gly Ser Ser Asn Phe Ile Ser Tyr Phe Asp Asp Met Ser Phe
        115                 120                 125

Glu His Arg Pro Ser Ile Leu Asp Gly Ser Val Asn Glu Pro Phe Lys
    130                 135                 140

Thr Lys Phe Val Gly Pro Thr Leu Glu Lys Glu Ile Arg Arg Arg Glu
145                 150                 155                 160

Lys Glu Leu Met Ala Met Arg Lys Asn Leu His His Arg Lys Ser Ser
                165                 170                 175

Pro Asp Ala Val Asp Ser Val Gly Lys Asn Asp Gly Ala Ala Pro Thr
            180                 185                 190

Thr Val Pro Thr Ala Ala Thr Ser Glu Thr Val Val Thr Val Glu Thr
        195                 200                 205
```

```
Thr Ile Ile Ser Ser Asn Phe Ser Gly Leu Tyr Val Ala Phe Trp Met
    210                 215                 220

Ala Ile Ala Phe Gly Ala Val Lys Ala Leu Ile Asp Tyr Tyr Gln
225                 230                 235                 240

His Asn Gly Ser Phe Lys Asp Ser Glu Ile Leu Lys Phe Met Thr Thr
                245                 250                 255

Asn Leu Phe Thr Val Ala Ser Val Asp Leu Leu Met Tyr Leu Ser Thr
                260                 265                 270

Tyr Phe Val Val Gly Ile Gln Tyr Leu Cys Lys Trp Gly Val Leu Lys
            275                 280                 285

Trp Gly Thr Thr Gly Trp Ile Phe Thr Ser Ile Tyr Glu Phe Leu Phe
    290                 295                 300

Val Ile Phe Tyr Met Tyr Leu Thr Glu Asn Ile Leu Lys Leu His Trp
305                 310                 315                 320

Leu Ser Lys Ile Phe Leu Phe Leu His Ser Leu Val Leu Leu Met Lys
                325                 330                 335

Met His Ser Phe Ala Phe Tyr Asn Gly Tyr Leu Trp Gly Ile Lys Glu
                340                 345                 350

Glu Leu Gln Phe Ser Lys Ser Ala Leu Ala Lys Tyr Lys Asp Ser Ile
            355                 360                 365

Asn Asp Pro Lys Val Ile Gly Ala Leu Glu Lys Ser Cys Glu Phe Cys
    370                 375                 380

Ser Phe Glu Leu Ser Ser Gln Ser Leu Ser Asp Gln Thr Gln Lys Phe
385                 390                 395                 400

Pro Asn Asn Ile Ser Ala Lys Ser Phe Phe Trp Phe Thr Met Phe Pro
                405                 410                 415

Thr Leu Ile Tyr Gln Ile Glu Tyr Pro Arg Thr Lys Glu Ile Arg Trp
                420                 425                 430

Ser Tyr Val Leu Glu Lys Ile Cys Ala Ile Phe Gly Thr Ile Phe Leu
            435                 440                 445

Met Met Ile Asp Ala Gln Ile Leu Met Tyr Pro Val Ala Met Arg Ala
    450                 455                 460

Leu Ala Val Arg Asn Ser Glu Trp Thr Gly Ile Leu Asp Arg Leu Leu
465                 470                 475                 480

Lys Trp Val Gly Leu Leu Val Asp Ile Val Pro Gly Phe Ile Val Met
                485                 490                 495

Tyr Ile Leu Asp Phe Tyr Leu Ile Trp Asp Ala Ile Leu Asn Cys Val
                500                 505                 510

Ala Glu Leu Thr Arg Phe Gly Asp Arg Tyr Phe Tyr Gly Asp Trp Trp
            515                 520                 525

Asn Cys Val Ser Trp Ala Asp Phe Ser Arg Ile Trp Asn Ile Pro Val
    530                 535                 540

His Lys Phe Leu Leu Arg His Val Tyr His Ser Ser Met Ser Ser Phe
545                 550                 555                 560

Lys Leu Asn Lys Ser Gln Ala Thr Leu Met Thr Phe Phe Leu Ser Ser
                565                 570                 575

Val Val His Glu Leu Ala Met Tyr Val Ile Phe Lys Lys Leu Arg Phe
                580                 585                 590

Tyr Leu Phe Phe Phe Gln Met Leu Gln Met Pro Leu Val Ala Leu Thr
            595                 600                 605

Asn Thr Lys Phe Met Arg Asn Arg Thr Ile Ile Gly Asn Val Ile Phe
    610                 615                 620
```

```
Trp Leu Gly Ile Cys Met Gly Pro Ser Val Met Cys Thr Leu Tyr Leu
625                 630                 635                 640

Thr Phe

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atgtcgaaag ctacatataa ggaacgtgct gcatctcatc ccagctgaag cttcgtacgc    60

<210> SEQ ID NO 34
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttagttttgc tggccgcatc ttctcaaata tgcttcccag gcataggcca ctagtggatc    60
tg                                                                  62

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaatactcag gtatcgtaag atgcaagagt tcgaatctct ccagctgaag cttcgtacgc    60

<210> SEQ ID NO 36
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tctaccctat gaacatattc cattttgtaa tttcgtgtcg gcataggcca ctagtggatc    60
tg                                                                  62

<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atgacagagc agaaagccct agtaaagcgt attacaaatg ccagctgaag cttcgtacgc    60

<210> SEQ ID NO 38
<211> LENGTH: 62
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 38
ctacataaga acacctttgg tggagggaac atcgttggta gcataggcca ctagtggatc    60
tg                                                                  62

<210> SEQ ID NO 39
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atgagtgaaa cagaattgag aaaaagacag gcccaattca ccagctgaag cttcgtacgc    60

<210> SEQ ID NO 40
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ttattgagtt gcttcttggg aagtttggga gggggtttcg gcataggcca ctagtggatc    60
tg                                                                  62

<210> SEQ ID NO 41
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atgagttctg tcgcagaaaa tataatacaa catgccactc ccagctgaag cttcgtacgc    60

<210> SEQ ID NO 42
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ttattcgaag acttctccag taattgggtc tctcttttg gcataggcca ctagtggatc     60
tg                                                                  62

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctgcggccgc aacatgacca ccaatacggt ccc                                33
```

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
ttctcgagtc tttagttatg cttgctc                                    27

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
ctgcggccgc aagatggacc tggttctcag tgc                             33

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
ttctcgagct acttattctt tgtaaactc                                  29

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
ctgcggccgc aagatggagc ccgccgtgtc gc                              32

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
aactcgagtc agtgccttgc cgccttgc                                   28

<210> SEQ ID NO 49
<211> LENGTH: 1833
<212> TYPE: DNA
<213> ORGANISM: Saccharomyces cerevisiae
<220> FEATURE:
<221> NAME/KEY: CDS
<222> LOCATION: (1)..(1833)

<400> SEQUENCE: 49 atg acg gag act aag gat ttg ttg caa gac gaa gag ttt ctt aag atc    48
Met Thr Glu Thr Lys Asp Leu Leu Gln Asp Glu Glu Phe Leu Lys Ile
 1               5                  10                  15

```
cgc aga ctc aat tcc gca gaa gcc aac aaa cgg cat tcg gtc acg tac         96
Arg Arg Leu Asn Ser Ala Glu Ala Asn Lys Arg His Ser Val Thr Tyr
             20                  25                  30 gat aac gtg atc ctg cca cag gag tcc atg gag gtt tcg cca cgg tcg        144
Asp Asn Val Ile Leu Pro Gln Glu Ser Met Glu Val Ser Pro Arg Ser
             35                  40                  45 tct acc acg tcg ctg gtg gag cca gtg gag tcg act gaa gga gtg gag        192
Ser Thr Thr Ser Leu Val Glu Pro Val Glu Ser Thr Glu Gly Val Glu
 50                  55                  60 tcg act gag gcg gaa cgt gtg gca ggg aag cag gag cag gag gag gag        240
Ser Thr Glu Ala Glu Arg Val Ala Gly Lys Gln Glu Gln Glu Glu Glu
 65                  70                  75                  80 tac cct gtg gac gcc cac atg caa aag tac ctt tca cac ctg aag agc        288
Tyr Pro Val Asp Ala His Met Gln Lys Tyr Leu Ser His Leu Lys Ser
                 85                  90                  95 aag tct cgg tcg agg ttc cac cga aag gat gct agc aag tat gtg tcg        336
Lys Ser Arg Ser Arg Phe His Arg Lys Asp Ala Ser Lys Tyr Val Ser
            100                 105                 110 ttt ttt ggg gac gtg agt ttt gat cct cgc ccc acg ctc ctg gac agc        384
Phe Phe Gly Asp Val Ser Phe Asp Pro Arg Pro Thr Leu Leu Asp Ser
            115                 120                 125 gcc atc aac gtg ccc ttc cag acg act ttc aaa ggt ccg gtg ctg gag        432
Ala Ile Asn Val Pro Phe Gln Thr Thr Phe Lys Gly Pro Val Leu Glu
130                 135                 140 aaa cag ctc aaa aat tta cag ttg aca aag acc aag acc aag gcc acg        480
Lys Gln Leu Lys Asn Leu Gln Leu Thr Lys Thr Lys Thr Lys Ala Thr
145                 150                 155                 160 gtg aag act acg gtg aag act acg gag aaa acg gac aag gca gat gcc        528
Val Lys Thr Thr Val Lys Thr Thr Glu Lys Thr Asp Lys Ala Asp Ala
                165                 170                 175 ccc cca gga gaa aaa ctg gag tcg aac ttt tca ggg atc tac gtg ttc        576
Pro Pro Gly Glu Lys Leu Glu Ser Asn Phe Ser Gly Ile Tyr Val Phe
            180                 185                 190 gca tgg atg ttc ttg ggc tgg ata gcc atc agg tgc tgc aca gat tac        624
Ala Trp Met Phe Leu Gly Trp Ile Ala Ile Arg Cys Cys Thr Asp Tyr
            195                 200                 205 tat gcg tcg tac ggc agt gca tgg aat aag ctg gaa atc gtg cag tac        672
Tyr Ala Ser Tyr Gly Ser Ala Trp Asn Lys Leu Glu Ile Val Gln Tyr
            210                 215                 220 atg aca acg gac ttg ttc acg atc gca atg ttg gac ttg gca atg ttc        720
Met Thr Thr Asp Leu Phe Thr Ile Ala Met Leu Asp Leu Ala Met Phe
225                 230                 235                 240 ctg tgc act ttc ttc gtg gtt ttc gtg cac tgg ctg gtg aaa aag cgg        768
Leu Cys Thr Phe Phe Val Val Phe Val His Trp Leu Val Lys Lys Arg
                245                 250                 255 atc atc aac tgg aag tgg act ggg ttc gtt gca gtg agc atc ttc gag        816
Ile Ile Asn Trp Lys Trp Thr Gly Phe Val Ala Val Ser Ile Phe Glu
            260                 265                 270 ttg gct ttc atc ccc gtg acg ttc ccc att tac gtc tac tac ttt gat        864
Leu Ala Phe Ile Pro Val Thr Phe Pro Ile Tyr Val Tyr Tyr Phe Asp
            275                 280                 285 ttc aac tgg gtc acg aga atc ttc ctg ttc ctg cac tcc gtg gtg ttt        912
Phe Asn Trp Val Thr Arg Ile Phe Leu Phe Leu His Ser Val Val Phe
            290                 295                 300 gtt atg aag agc cac tcg ttt gcc ttt tac aac ggg tat ctt tgg gac        960
Val Met Lys Ser His Ser Phe Ala Phe Tyr Asn Gly Tyr Leu Trp Asp
305                 310                 315                 320 ata aag cag gaa ctc gag tac tct tcc aaa cag ttg caa aaa tac aag       1008
Ile Lys Gln Glu Leu Glu Tyr Ser Ser Lys Gln Leu Gln Lys Tyr Lys
```

```
                  325                 330                 335
gaa tct ttg tcc cca gag acc cgc gag att ctg caa aaa agt tgc gac    1056
Glu Ser Leu Ser Pro Glu Thr Arg Glu Ile Leu Gln Lys Ser Cys Asp
        340                 345                 350 ttt tgc ctt ttc gaa ttg aac tac cag acc aag gat aac gac ttc ccc    1104
Phe Cys Leu Phe Glu Leu Asn Tyr Gln Thr Lys Asp Asn Asp Phe Pro
            355                 360                 365 aac aac atc agt tgc agc aat ttc ttc atg ttc tgt ttg ttc ccc gtc    1152
Asn Asn Ile Ser Cys Ser Asn Phe Phe Met Phe Cys Leu Phe Pro Val
        370                 375                 380 ctc gtg tac cag atc aac tac cca aga acg tcg cgc atc aga tgg agg    1200
Leu Val Tyr Gln Ile Asn Tyr Pro Arg Thr Ser Arg Ile Arg Trp Arg
385                 390                 395                 400 tat gtg ttg gag aag gtg tgc gcc atc att ggc acc atc ttc ctc atg    1248
Tyr Val Leu Glu Lys Val Cys Ala Ile Ile Gly Thr Ile Phe Leu Met
                405                 410                 415 atg gtc acg gca cag ttc ttc atg cac ccg gtg gcc atg cgc tgt atc    1296
Met Val Thr Ala Gln Phe Phe Met His Pro Val Ala Met Arg Cys Ile
            420                 425                 430 cag ttc cac aac acg ccc acc ttc ggc ggc tgg atc ccc gcc acg caa    1344
Gln Phe His Asn Thr Pro Thr Phe Gly Gly Trp Ile Pro Ala Thr Gln
        435                 440                 445 gag tgg ttc cac ctg ctc ttc gac atg att ccg ggc ttc act gtt ctg    1392
Glu Trp Phe His Leu Leu Phe Asp Met Ile Pro Gly Phe Thr Val Leu
    450                 455                 460 tac atg ctc acg ttt tac atg ata tgg gac gct tta ttg aat tgc gtg    1440
Tyr Met Leu Thr Phe Tyr Met Ile Trp Asp Ala Leu Leu Asn Cys Val
465                 470                 475                 480 gcg gag ttg acc agg ttt gcg gac aga tat ttc tac ggc gac tgg tgg    1488
Ala Glu Leu Thr Arg Phe Ala Asp Arg Tyr Phe Tyr Gly Asp Trp Trp
                485                 490                 495 aat tgc gtt tcg ttt gaa gag ttt agc aga atc tgg aac gtc ccc gtt    1536
Asn Cys Val Ser Phe Glu Glu Phe Ser Arg Ile Trp Asn Val Pro Val
            500                 505                 510 cac aaa ttt tta cta aga cac gtg tac cac agc tcc atg ggc gca ttg    1584
His Lys Phe Leu Leu Arg His Val Tyr His Ser Ser Met Gly Ala Leu
        515                 520                 525 cat ttg agc aag agc caa gct aca tta ttt act ttt ttc ttg agt gcc    1632
His Leu Ser Lys Ser Gln Ala Thr Leu Phe Thr Phe Phe Leu Ser Ala
    530                 535                 540 gtg ttc cac gaa atg gcc atg ttc gcc att ttc aga agg gtt aga gga    1680
Val Phe His Glu Met Ala Met Phe Ala Ile Phe Arg Arg Val Arg Gly
545                 550                 555                 560 tat ctg ttc atg ttc caa ctg tcg cag ttt gtg tgg act gct ttg agc    1728
Tyr Leu Phe Met Phe Gln Leu Ser Gln Phe Val Trp Thr Ala Leu Ser
                565                 570                 575 aac acc aag ttt cta cgg gca aga ccg cag ttg tcc aac gtt gtc ttt    1776
Asn Thr Lys Phe Leu Arg Ala Arg Pro Gln Leu Ser Asn Val Val Phe
            580                 585                 590 tcg ttt ggt gtc tgt tca ggg ccc agt atc att atg acg ttg tac ctg    1824
Ser Phe Gly Val Cys Ser Gly Pro Ser Ile Ile Met Thr Leu Tyr Leu
        595                 600                 605 acc tta tga                                                        1833
Thr Leu
    610

<210> SEQ ID NO 50
<211> LENGTH: 610
<212> TYPE: PRT
<213> ORGANISM: Saccharomyces cerevisiae
```

<400> SEQUENCE: 50

```
Met Thr Glu Thr Lys Asp Leu Leu Gln Asp Glu Phe Leu Lys Ile
1               5                   10                  15

Arg Arg Leu Asn Ser Ala Glu Ala Asn Lys Arg His Ser Val Thr Tyr
            20                  25                  30

Asp Asn Val Ile Leu Pro Gln Glu Ser Met Glu Val Ser Pro Arg Ser
            35                  40                  45

Ser Thr Thr Ser Leu Val Glu Pro Val Glu Ser Thr Glu Gly Val Glu
    50                  55                  60

Ser Thr Glu Ala Glu Arg Val Ala Gly Lys Gln Glu Gln Glu Glu Glu
65              70                  75                  80

Tyr Pro Val Asp Ala His Met Gln Lys Tyr Leu Ser His Leu Lys Ser
                85                  90                  95

Lys Ser Arg Ser Arg Phe His Arg Lys Asp Ala Ser Lys Tyr Val Ser
            100                 105                 110

Phe Phe Gly Asp Val Ser Phe Asp Pro Arg Pro Thr Leu Leu Asp Ser
            115                 120                 125

Ala Ile Asn Val Pro Phe Gln Thr Thr Phe Lys Gly Pro Val Leu Glu
    130                 135                 140

Lys Gln Leu Lys Asn Leu Gln Leu Thr Lys Thr Lys Thr Lys Ala Thr
145                 150                 155                 160

Val Lys Thr Thr Val Lys Thr Thr Glu Lys Thr Asp Lys Ala Asp Ala
                165                 170                 175

Pro Pro Gly Glu Lys Leu Glu Ser Asn Phe Ser Gly Ile Tyr Val Phe
            180                 185                 190

Ala Trp Met Phe Leu Gly Trp Ile Ala Ile Arg Cys Cys Thr Asp Tyr
            195                 200                 205

Tyr Ala Ser Tyr Gly Ser Ala Trp Asn Lys Leu Glu Ile Val Gln Tyr
    210                 215                 220

Met Thr Thr Asp Leu Phe Thr Ile Ala Met Leu Asp Leu Ala Met Phe
225                 230                 235                 240

Leu Cys Thr Phe Phe Val Val Phe Val His Trp Leu Val Lys Lys Arg
                245                 250                 255

Ile Ile Asn Trp Lys Trp Thr Gly Phe Val Ala Val Ser Ile Phe Glu
            260                 265                 270

Leu Ala Phe Ile Pro Val Thr Phe Pro Ile Tyr Val Tyr Tyr Phe Asp
            275                 280                 285

Phe Asn Trp Val Thr Arg Ile Phe Leu Phe Leu His Ser Val Val Phe
    290                 295                 300

Val Met Lys Ser His Ser Phe Ala Phe Tyr Asn Gly Tyr Leu Trp Asp
305                 310                 315                 320

Ile Lys Gln Glu Leu Glu Tyr Ser Ser Lys Gln Leu Gln Lys Tyr Lys
                325                 330                 335

Glu Ser Leu Ser Pro Glu Thr Arg Glu Ile Leu Gln Lys Ser Cys Asp
            340                 345                 350

Phe Cys Leu Phe Glu Leu Asn Tyr Gln Thr Lys Asp Asn Asp Phe Pro
            355                 360                 365

Asn Asn Ile Ser Cys Ser Asn Phe Phe Met Phe Cys Leu Phe Pro Val
    370                 375                 380

Leu Val Tyr Gln Ile Asn Tyr Pro Arg Thr Ser Arg Ile Arg Trp Arg
385                 390                 395                 400

Tyr Val Leu Glu Lys Val Cys Ala Ile Ile Gly Thr Ile Phe Leu Met
```

-continued

```
                405                 410                 415
Met Val Thr Ala Gln Phe Phe Met His Pro Val Ala Met Arg Cys Ile
            420                 425                 430

Gln Phe His Asn Thr Pro Thr Phe Gly Gly Trp Ile Pro Ala Thr Gln
            435                 440                 445

Glu Trp Phe His Leu Leu Phe Asp Met Ile Pro Gly Phe Thr Val Leu
            450                 455                 460

Tyr Met Leu Thr Phe Tyr Met Ile Trp Asp Ala Leu Leu Asn Cys Val
465                 470                 475                 480

Ala Glu Leu Thr Arg Phe Ala Asp Arg Tyr Phe Tyr Gly Asp Trp Trp
            485                 490                 495

Asn Cys Val Ser Phe Glu Glu Phe Ser Arg Ile Trp Asn Val Pro Val
            500                 505                 510

His Lys Phe Leu Leu Arg His Val Tyr His Ser Ser Met Gly Ala Leu
            515                 520                 525

His Leu Ser Lys Ser Gln Ala Thr Leu Phe Thr Phe Phe Leu Ser Ala
            530                 535                 540

Val Phe His Glu Met Ala Met Phe Ala Ile Phe Arg Arg Val Arg Gly
545                 550                 555                 560

Tyr Leu Phe Met Phe Gln Leu Ser Gln Phe Val Trp Thr Ala Leu Ser
            565                 570                 575

Asn Thr Lys Phe Leu Arg Ala Arg Pro Gln Leu Ser Asn Val Val Phe
            580                 585                 590

Ser Phe Gly Val Cys Ser Gly Pro Ser Ile Ile Met Thr Leu Tyr Leu
            595                 600                 605

Thr Leu
    610

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctgcggccgc atcatgtctg ctgttaacgt tgc                                33

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttctcgagtt aaccaatcaa ctcaccaaac                                    30

<210> SEQ ID NO 53
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctgcggccgc aggatgtctg ctaccaagtc aatcg                              35
```

<210> SEQ ID NO 54
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
atctcgagct tagatctttt gttctggatt tctc         34

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
ctgcggccgc accatgaagt ttttcccact cc           32

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
ttctcgagtt agaactttt gttttgcaac aag           33

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
ctgcggccgc aatatggatt tggtcttaga agtcg        35

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
aactcgagtc agttgttctt cttggtattt g             31

<210> SEQ ID NO 59
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
ctgcggccgc actatggcaa aggataatag tgag          34

```
<210> SEQ ID NO 60
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttctcgagct agaaaacata aggaataaag ac                                         32
```